United States Patent
Faucher et al.

(10) Patent No.: US 8,501,229 B2
(45) Date of Patent: *Aug. 6, 2013

(54) HYDROPHOBIC CROSS-LINKED GELS FOR BIOABSORBABLE DRUG CARRIER COATINGS

(75) Inventors: Keith M. Faucher, Nashua, NH (US); Hui Tang, Acton, MA (US); Lisa Rogers, Londonderry, NH (US); Joseph Ferraro, Londonderry, NH (US); Paul Martakos, Pelham, NH (US); Steve A. Herweck, Nashua, NH (US); Theodore Karwoski, Hollis, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/404,487

(22) Filed: Feb. 24, 2012

(65) Prior Publication Data
US 2012/0213839 A1    Aug. 23, 2012

Related U.S. Application Data

(63) Continuation of application No. 11/582,135, filed on Oct. 16, 2006, now Pat. No. 8,124,127.

(60) Provisional application No. 60/727,312, filed on Oct. 15, 2005.

(51) Int. Cl.
*A61K 9/00* (2006.01)
*A61F 2/00* (2006.01)

(52) U.S. Cl.
USPC .................. 424/484; 424/425; 424/426

(58) Field of Classification Search
None
See application file for complete search history.

(56) References Cited

U.S. PATENT DOCUMENTS

| | | | |
|---|---|---|---|
| 2,368,306 A | 1/1945 | Kiefer et al. | |
| 2,986,540 A | 5/1961 | Posnansky | |
| 3,464,413 A | 9/1969 | Goldfarb et al. | |
| 3,556,294 A | 1/1971 | Walck et al. | |
| 3,567,820 A | 3/1971 | Sperti | |
| 3,967,728 A | 7/1976 | Gordon | |
| 4,308,120 A | 12/1981 | Pennewiss et al. | |
| 4,323,547 A | 4/1982 | Knust et al. | |
| 4,557,925 A | 12/1985 | Lindahl et al. | |
| 4,664,114 A | 5/1987 | Ghodstain | |
| 4,813,210 A | 3/1989 | Masuda et al. | |
| 4,814,329 A | 3/1989 | Harsanyi et al. | |
| 4,847,301 A | 7/1989 | Murray | |
| 4,880,455 A | 11/1989 | Blank | |
| 4,883,667 A | 11/1989 | Eckenhoff | |
| 4,886,787 A | 12/1989 | De Belder et al. | |
| 4,894,231 A | 1/1990 | Moreau et al. | |
| 4,895,724 A | 1/1990 | Cardinal et al. | |
| 4,911,707 A | 3/1990 | Heiber et al. | |
| 4,941,308 A | 7/1990 | Grabenkort et al. | |
| 4,952,419 A | 8/1990 | De Leon et al. | |
| 4,968,302 A | 11/1990 | Schluter et al. | |
| 5,017,229 A | 5/1991 | Burns et al. | |
| 5,132,115 A | 7/1992 | Wolter et al. | |
| 5,147,374 A | 9/1992 | Fernandez | |
| 5,151,272 A | 9/1992 | Engstrom et al. | |
| 5,171,148 A | 12/1992 | Wasserman et al. | |
| 5,176,956 A | 1/1993 | Jevne et al. | |
| 5,179,174 A | 1/1993 | Elton | |
| 5,254,105 A | 10/1993 | Haaga | |
| 5,356,432 A | 10/1994 | Rutkow et al. | |
| 5,368,602 A | 11/1994 | de la Torre | |
| 5,371,109 A | 12/1994 | Engstrom et al. | |
| 5,380,328 A | 1/1995 | Morgan | |
| 5,387,658 A * | 2/1995 | Schroder et al. | 525/530 |
| 5,403,283 A | 4/1995 | Luther | |
| 5,447,940 A | 9/1995 | Harvey et al. | |
| 5,464,650 A | 11/1995 | Berg et al. | |
| 5,480,653 A | 1/1996 | Aguadisch et al. | |
| 5,509,899 A | 4/1996 | Fan et al. | |
| 5,579,149 A | 11/1996 | Moret et al. | |
| 5,580,923 A | 12/1996 | Yeung et al. | |
| 5,591,230 A | 1/1997 | Horn et al. | |
| 5,593,441 A | 1/1997 | Lichtenstein et al. | |
| 5,612,074 A | 3/1997 | Leach | |
| 5,614,284 A | 3/1997 | Kranzler et al. | |
| 5,627,077 A | 5/1997 | Dyllick-Brenzinger et al. | |
| 5,637,113 A | 6/1997 | Tartaglia et al. | |
| 5,665,115 A | 9/1997 | Cragg | |
| 5,695,525 A | 12/1997 | Mulhauser et al. | |
| 5,700,286 A | 12/1997 | Tartaglia et al. | |

(Continued)

FOREIGN PATENT DOCUMENTS

EP    0 471 566    2/1992
EP    0610731    8/1994

(Continued)

OTHER PUBLICATIONS

Final Office Action for U.S. Appl. No. 12/182,261 (listed on SB-08 as US-2009-0047414) mailed Apr. 30, 2012.
Notice of Allowance for U.S. Appl. No. 11/236,908 (listed on SB-08 as US-2006-0067974) mailed May 11, 2012.
"Cure" in Academic Press Dictionary of Science and Technology (1992).
"Polymerization" Merriam-Webster Online Dictionary, retrieved from <www.merriam-webster.com> on Dec. 13, 2009; Merriam-Webster's Inc. 2009; pp. 1.
A paper entitled "Evaluation of the Biocompatibility and Drug Delivery Capabilities of Biological Oil Based Stent Coatings" by Shengqio Li of the Katholieke Universiteit Leuven.
Ahuja, et al. Journal of Indian Pediatric Surgery 2002 7:15-20.
Autosuture, "ParietexTM Composite OS Series Mesh," retrieved online at http://www.autosuture.com/AutoSuture/pagebuilder.aspx?topicID=135734&breadcrumbs=135 601:0 (2007).

(Continued)

*Primary Examiner* — James H Alstrum Acevedo
*Assistant Examiner* — Jessica Kassa
(74) *Attorney, Agent, or Firm* — Sean D. Detweiler, Esq.; Morse, Barnes-Brown & Pendleton, P.C.

(57) ABSTRACT

Coatings for medical devices, methods of making the coatings, and methods of using them are described.

25 Claims, 26 Drawing Sheets

U.S. PATENT DOCUMENTS

| | | | |
|---|---|---|---|
| 5,736,152 A | 4/1998 | Dunn | |
| 5,753,259 A | 5/1998 | Engstrom et al. | |
| 5,760,081 A | 6/1998 | Leaf et al. | |
| 5,766,246 A | 6/1998 | Mulhauser et al. | |
| 5,766,710 A | 6/1998 | Turnlund et al. | |
| 5,817,343 A | 10/1998 | Burke | |
| 5,824,082 A | 10/1998 | Brown | |
| 5,837,313 A | 11/1998 | Ding et al. | |
| 5,843,919 A | 12/1998 | Burger | |
| 5,874,470 A | 2/1999 | Nehne et al. | |
| 5,879,359 A | 3/1999 | Dorigatti et al. | |
| 5,898,040 A | 4/1999 | Shalaby et al. | |
| 5,906,831 A | 5/1999 | Larsson et al. | |
| 5,931,165 A | 8/1999 | Reich et al. | |
| 5,955,502 A | 9/1999 | Hansen et al. | |
| 5,986,043 A | 11/1999 | Hubbell et al. | |
| 6,005,004 A | 12/1999 | Katz et al. | |
| 6,010,766 A | 1/2000 | Braun et al. | |
| 6,010,776 A | 1/2000 | Exsted et al. | |
| 6,015,844 A | 1/2000 | Harvey et al. | |
| 6,028,164 A | 2/2000 | Loomis | |
| 6,040,330 A | 3/2000 | Hausheer et al. | |
| 6,056,970 A | 5/2000 | Greenwalt et al. | |
| 6,077,698 A | 6/2000 | Swan et al. | |
| 6,083,950 A | 7/2000 | Anand et al. | |
| 6,090,809 A | 7/2000 | Anand et al. | |
| 6,093,792 A | 7/2000 | Gross et al. | |
| 6,117,911 A | 9/2000 | Grainger et al. | |
| 6,120,789 A | 9/2000 | Dunn | |
| 6,132,765 A | 10/2000 | DiCosmo et al. | |
| 6,146,358 A | 11/2000 | Rowe | |
| 6,152,944 A | 11/2000 | Holman et al. | |
| 6,176,863 B1 | 1/2001 | Kugel et al. | |
| 6,193,746 B1 | 2/2001 | Strecker | |
| 6,197,357 B1 | 3/2001 | Lawton et al. | |
| 6,203,551 B1 | 3/2001 | Wu | |
| 6,206,916 B1 | 3/2001 | Furst | |
| 6,211,315 B1 | 4/2001 | Larock et al. | |
| 6,228,383 B1 | 5/2001 | Hansen et al. | |
| 6,229,032 B1 | 5/2001 | Jacobs et al. | |
| 6,245,811 B1 | 6/2001 | Horrobin et al. | |
| 6,254,634 B1 | 7/2001 | Anderson et al. | |
| 6,262,109 B1 | 7/2001 | Clark et al. | |
| 6,273,913 B1 | 8/2001 | Wright et al. | |
| 6,284,268 B1 | 9/2001 | Mishra et al. | |
| 6,299,604 B1 | 10/2001 | Ragheb et al. | |
| 6,326,360 B1 | 12/2001 | Kanazawa et al. | |
| 6,331,568 B1 | 12/2001 | Horrobin | |
| 6,346,110 B2 | 2/2002 | Wu | |
| 6,358,556 B1 | 3/2002 | Ding et al. | |
| 6,364,893 B1 | 4/2002 | Sahatjian et al. | |
| 6,368,658 B1 | 4/2002 | Schwarz et al. | |
| 6,369,039 B1 | 4/2002 | Palasis et al. | |
| 6,387,379 B1 | 5/2002 | Goldberg et al. | |
| 6,410,587 B1 | 6/2002 | Grainger et al. | |
| 6,444,318 B1 | 9/2002 | Guire et al. | |
| 6,451,373 B1 | 9/2002 | Hossainy et al. | |
| 6,465,525 B1 | 10/2002 | Guire et al. | |
| 6,471,980 B2 | 10/2002 | Sirhan et al. | |
| 6,479,683 B1 | 11/2002 | Abney et al. | |
| 6,491,938 B2 | 12/2002 | Kunz | |
| 6,500,453 B2 | 12/2002 | Brey et al. | |
| 6,503,556 B2 | 1/2003 | Harish et al. | |
| 6,525,145 B2 | 2/2003 | Gevaert et al. | |
| 6,527,801 B1 | 3/2003 | Dutta | |
| 6,534,693 B2 | 3/2003 | Fischell et al. | |
| 6,548,081 B2 | 4/2003 | Sadozai et al. | |
| 6,565,659 B1 | 5/2003 | Pacetti et al. | |
| 6,569,441 B2 | 5/2003 | Kunz et al. | |
| 6,599,323 B2 | 7/2003 | Melican et al. | |
| 6,610,035 B2 | 8/2003 | Yang et al. | |
| 6,610,068 B2 | 8/2003 | Yang et al. | |
| 6,630,151 B1 | 10/2003 | Tarletsky et al. | |
| 6,630,167 B2 | 10/2003 | Zhang | |
| 6,632,822 B1 | 10/2003 | Rickards et al. | |
| 6,641,611 B2 | 11/2003 | Jayaraman | |
| 6,645,547 B1 | 11/2003 | Shekalim | |
| 6,663,880 B1 | 12/2003 | Roorda et al. | |
| 6,669,735 B1 | 12/2003 | Pelissier | |
| 6,670,355 B2 | 12/2003 | Azrolan et al. | |
| 6,677,342 B2 | 1/2004 | Wolff et al. | |
| 6,677,386 B1 | 1/2004 | Giezen et al. | |
| 6,685,956 B2 | 2/2004 | Chu et al. | |
| 6,730,064 B2 | 5/2004 | Ragheb et al. | |
| 6,753,071 B1 | 6/2004 | Pacetti | |
| 6,761,903 B2 | 7/2004 | Chen et al. | |
| 6,764,509 B2 | 7/2004 | Chinn et al. | |
| 6,776,796 B2 | 8/2004 | Falotico et al. | |
| 6,794,485 B2 | 9/2004 | Shalaby et al. | |
| 6,833,004 B2 | 12/2004 | Ishii et al. | |
| 6,852,330 B2 | 2/2005 | Bowman et al. | |
| 6,875,230 B1 | 4/2005 | Morita et al. | |
| 6,884,428 B2 | 4/2005 | Binette et al. | |
| 6,887,270 B2 | 5/2005 | Miller et al. | |
| 6,899,729 B1 | 5/2005 | Cox et al. | |
| 6,918,927 B2 | 7/2005 | Bates et al. | |
| 6,996,952 B2 | 2/2006 | Gupta et al. | |
| 7,070,858 B2 | 7/2006 | Shalaby et al. | |
| 7,101,381 B2 | 9/2006 | Ford et al. | |
| 7,152,611 B2 | 12/2006 | Brown et al. | |
| 7,323,189 B2 | 1/2008 | Pathak | |
| 7,415,811 B2 | 8/2008 | Gottlieb et al. | |
| 8,124,127 B2 | 2/2012 | Faucher et al. | |
| 8,263,102 B2 | 9/2012 | Labrecque et al. | |
| 8,312,836 B2 | 11/2012 | Corbeil et al. | |
| 8,367,099 B2 | 2/2013 | Swanick et al. | |
| 2001/0025196 A1 | 9/2001 | Chinn et al. | |
| 2001/0051595 A1 | 12/2001 | Lyons et al. | |
| 2002/0002154 A1 | 1/2002 | Guivarc'h et al. | |
| 2002/0007209 A1 | 1/2002 | Scheerder et al. | |
| 2002/0012741 A1 | 1/2002 | Heinz et al. | |
| 2002/0026899 A1 | 3/2002 | McLaughlin et al. | |
| 2002/0026900 A1 | 3/2002 | Huang et al. | |
| 2002/0032414 A1 | 3/2002 | Ragheb et al. | |
| 2002/0098278 A1 | 7/2002 | Bates et al. | |
| 2002/0116045 A1 | 8/2002 | Eidenschink | |
| 2002/0120333 A1 | 8/2002 | Keogh et al. | |
| 2002/0122877 A1 | 9/2002 | Harish et al. | |
| 2002/0142089 A1 | 10/2002 | Koike et al. | |
| 2002/0193829 A1 | 12/2002 | Kennedy et al. | |
| 2003/0003125 A1 | 1/2003 | Nathan et al. | |
| 2003/0004564 A1 | 1/2003 | Elkins et al. | |
| 2003/0055403 A1 | 3/2003 | Nestenborg et al. | |
| 2003/0065292 A1 | 4/2003 | Darouiche et al. | |
| 2003/0065345 A1 | 4/2003 | Weadock | |
| 2003/0069632 A1 | 4/2003 | De Scheerder et al. | |
| 2003/0072784 A1 | 4/2003 | Williams | |
| 2003/0077272 A1 | 4/2003 | Pathak | |
| 2003/0077310 A1 | 4/2003 | Pathak et al. | |
| 2003/0077452 A1 | 4/2003 | Guire et al. | |
| 2003/0083740 A1 | 5/2003 | Pathak | |
| 2003/0086958 A1 | 5/2003 | Arnold et al. | |
| 2003/0094728 A1 | 5/2003 | Tayebi | |
| 2003/0130206 A1 | 7/2003 | Koziak et al. | |
| 2003/0152609 A1 | 8/2003 | Fischell et al. | |
| 2003/0175408 A1 | 9/2003 | Timm et al. | |
| 2003/0176915 A1 | 9/2003 | Wright et al. | |
| 2003/0181975 A1 | 9/2003 | Ishii et al. | |
| 2003/0191179 A1 | 10/2003 | Joshi-Hangal et al. | |
| 2003/0204168 A1 | 10/2003 | Bosma et al. | |
| 2003/0204618 A1 | 10/2003 | Foster et al. | |
| 2003/0207019 A1 | 11/2003 | Shekalim et al. | |
| 2003/0220297 A1 | 11/2003 | Berstein et al. | |
| 2004/0006296 A1 | 1/2004 | Fischell et al. | |
| 2004/0014810 A1 | 1/2004 | Horrobin | |
| 2004/0018228 A1 | 1/2004 | Fischell et al. | |
| 2004/0039441 A1 | 2/2004 | Rowland et al. | |
| 2004/0071756 A1 | 4/2004 | Fischell et al. | |
| 2004/0072849 A1 | 4/2004 | Schreiber et al. | |
| 2004/0073284 A1 | 4/2004 | Bates et al. | |
| 2004/0133275 A1 | 7/2004 | Mansmann | |
| 2004/0137066 A1 | 7/2004 | Jayaraman | |
| 2004/0137179 A1 | 7/2004 | Matsuda et al. | |
| 2004/0142094 A1 | 7/2004 | Narayanan | |
| 2004/0146546 A1 | 7/2004 | Gravett et al. | |
| 2004/0156879 A1 | 8/2004 | Muratoglu et al. | |
| 2004/0161464 A1 | 8/2004 | Domb | |

| | | |
|---|---|---|
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shanahan et al. |
| 2004/0234574 A9 | 11/2004 | Sawhney et al. |
| 2004/0241211 A9 | 12/2004 | Fischell et al. |
| 2004/0256264 A1 | 12/2004 | Israelsson et al. |
| 2005/0010078 A1 | 1/2005 | Jamiolkowski et al. |
| 2005/0084514 A1 | 4/2005 | Shebuski et al. |
| 2005/0095267 A1 | 5/2005 | Campbell et al. |
| 2005/0106209 A1 | 5/2005 | Ameri et al. |
| 2005/0112170 A1 | 5/2005 | Hossainy et al. |
| 2005/0113849 A1 | 5/2005 | Popadiuk et al. |
| 2005/0129787 A1 | 6/2005 | Murad |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0182485 A1 | 8/2005 | Falotico et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0036311 A1 | 2/2006 | Nakayama et al. |
| 2006/0058881 A1 | 3/2006 | Trieu |
| 2006/0067974 A1 | 3/2006 | Labrecque et al. |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2007/0015893 A1 | 1/2007 | Hakuta et al. |
| 2007/0071798 A1 | 3/2007 | Herweck et al. |
| 2007/0084144 A1 | 4/2007 | Labrecque et al. |
| 2007/0093894 A1 | 4/2007 | Darouiche |
| 2007/0202149 A1 | 8/2007 | Faucher et al. |
| 2007/0212411 A1 | 9/2007 | Fawzy et al. |
| 2007/0264460 A1 | 11/2007 | Del Tredici |
| 2007/0275074 A1 | 11/2007 | Holm et al. |
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0044481 A1 | 2/2008 | Harel |
| 2008/0045557 A1 | 2/2008 | Grainger et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0206305 A1 | 8/2008 | Herweck et al. |
| 2008/0279929 A1 | 11/2008 | Devane et al. |
| 2008/0286440 A1 | 11/2008 | Scheer |
| 2009/0011116 A1 | 1/2009 | Herweck |
| 2009/0047414 A1 | 2/2009 | Corbeil et al. |
| 2009/0181937 A1 | 7/2009 | Faucher et al. |
| 2009/0208552 A1 | 8/2009 | Faucher et al. |
| 2010/0183697 A1 | 7/2010 | Faucher et al. |
| 2010/0209473 A1 | 8/2010 | Dhont et al. |
| 2010/0233232 A1 | 9/2010 | Swanick et al. |
| 2012/0016038 A1 | 1/2012 | Faucher et al. |

FOREIGN PATENT DOCUMENTS

| | | |
|---|---|---|
| EP | 0623354 | 11/1994 |
| EP | 0730864 | 9/1996 |
| EP | 0790822 | 8/1997 |
| EP | 0873133 | 10/1998 |
| EP | 0917561 | 5/1999 |
| EP | 1140243 | 10/2001 |
| EP | 1181943 | 2/2002 |
| EP | 1270024 | 1/2003 |
| EP | 1273314 | 1/2003 |
| EP | 1364628 | 11/2003 |
| EP | 1520795 | 4/2005 |
| EP | 1557183 | 7/2005 |
| EP | 2083875 | 8/2009 |
| EP | 1 402 906 | 6/2011 |
| WO | WO 86/00912 | 7/1984 |
| WO | WO 90/01969 | 3/1990 |
| WO | WO 95/26715 | 10/1995 |
| WO | WO 97/02042 | 1/1997 |
| WO | WO 97/09367 | 3/1997 |
| WO | WO 97/13528 | 4/1997 |
| WO | WO 98/30206 | 7/1998 |
| WO | WO 98/54275 | 12/1998 |
| WO | WO 99/25336 | 5/1999 |
| WO | WO 00/40278 | 7/2000 |
| WO | WO 00/62830 | 10/2000 |
| WO | WO 01/24866 | 4/2001 |
| WO | WO 01/26585 | 4/2001 |
| WO | WO 01/37808 | 5/2001 |
| WO | WO 01/60586 | 8/2001 |
| WO | WO 01/66036 | 9/2001 |
| WO | WO 01/76649 | 10/2001 |
| WO | WO 02/49535 | 6/2002 |
| WO | WO 02/100455 | 12/2002 |
| WO | WO 03/000308 | 1/2003 |
| WO | WO 03/015748 | 2/2003 |
| WO | WO 03/028622 | 4/2003 |
| WO | WO 03/037397 | 5/2003 |
| WO | WO 03/037398 | 5/2003 |
| WO | WO 03/039612 | 5/2003 |
| WO | WO 03/041756 | 5/2003 |
| WO | WO 03/070125 | 8/2003 |
| WO | WO 03/092741 | 11/2003 |
| WO | WO 03/092779 | 11/2003 |
| WO | WO 2004/004598 | 1/2004 |
| WO | WO 2004/006976 | 1/2004 |
| WO | WO 2004/006978 | 1/2004 |
| WO | WO 2004/028583 | 4/2004 |
| WO | WO 2004/091684 | 10/2004 |
| WO | WO 2005/000165 | 1/2005 |
| WO | WO 2005/016400 | 2/2005 |
| WO | WO 2005/053767 | 6/2005 |
| WO | WO 2005/073091 | 8/2005 |
| WO | WO 2005/116118 | 12/2005 |
| WO | WO 2006/024488 | 3/2006 |
| WO | WO 2006/036967 | 4/2006 |
| WO | WO 2006/102374 | 9/2006 |
| WO | WO 2007/047028 | 4/2007 |
| WO | WO 2008/057328 | 5/2008 |
| WO | WO 2012/009707 | 1/2012 |

OTHER PUBLICATIONS

Binder et al., "Chromatographic Analysis of Seed Oils. Fatty Acid Composition of Castor Oil," The Journal of the American Oil Chemists' Society, vol. 39:513-517 (1962).

Camurus, "In our endeavors to create the unique, we start with the best. Your product."

CECW-EE, "Ch. 4: Coating Types and Characteristics," Engineering and Design—Painting: New Construction and Maintenance, pp. 4-1 to 4-24 (1995).

De Scheerder, Ivan K., et al. "Biocompatibility of polymer-coated oversized metallic stents implanted in normal porcine coronary arteries," Atherosclerosis, vol. 114:105-114.

Drummond, Calum J., et al., "Surfactant self-assembly objects as novel drug delivery vehicles," Current Opinion in Colliod & Interface Science, vol. 4:449-456 (2000).

Engstrom, Sven, "Drug Delivery from Cubic and Other Lipid-water Phases," Lipid Technology, vol. 2(2):42-45 (1990).

Guler, et al. "Some empirical equations for oxopolymerization of linseed oil," Progress in Organic Coatings, vol. 51:365-371 (2004).

Hwang, Chao-Wei, et al, "Physiological Transport Forces Govern Drug Distribution for Stent-Based Delivery," Circulation, vol. 104:600-605 (2001).

Jonasson, Lena, et al., "Cyclosporon A inhibits smooth muscle proliferation in the vascular response to injury," Proc. Natl. Acad. Sci. USA, vol. 85: 2303-2306 (1988).

Mallegol, et al., "Drier Influence on the Curing of Linseed Oil," Progress in Organic Coatings 39:107-113 (2000).

Morse, Richard "Molecular Distillation of Polymerized Drying Oils," Industrial and Engineering Chemisry 33:1039-1043 (1941).

Oberhoff, Martin, et al, "Local and Systemic Delivery of Low Molecular Weight Heparin Following PTCA: Acute Results and 6-Month Follow-Up of the Initial Clinical Experience With the Porous Balloon (PILOT-Study)," Catheterization and Cardiovascular Diagnosis, vol. 44:267-274 (1998).

Ogunniyi, D.S., "Castor oil: A vital industrial raw material," Biosource Technology, vol. 97: 1086-1091 (2006).

Redman, L.V., et al., "The drying rate of raw paint oils—a comparison," The Journal of Industrial and Engineering Chemistry, vol. 5: 630-636 (1913).

Rutkow, Ira M., et al., "'Tension-free' inguinal herniorrhaphy: A preliminary report on the 'mesh plug' technique," Surgery, vol. 114:3-8 (1993).

Salu, Koen J., et al, "Addition of cytochalasin D to a biocompatible oil stent coating inhibits intimal hyperplasia in a porcine coronary model," Coronary Artery Disease, vol. 14(8):545-555 (2003).

Scheller, Bruno, et al, "Addition of Paclitaxel to Contrast Media Prevents Restenosis After Coronary Stent Implantation," Journal of the American College of Cardiology, vol. 42(8):1415-1420 (2003).

Shahidi, Fereidoon ed.; "Bailey's Industrial Oil and Fats Products" 2005; John Wiley and Sons; vol. 5, Edible Oil and Fat Products: Processing Technologies, pp. 1-15.

Van der Giessen, Willem J., et al, "Marked Inflammatory Sequelae to Implantation of Biodegradable and Nonbiodegradable Polymers in Porcine Coronary Arteries," Circulation, vol. 94:1690-1697 (1996).

Wikipedia, "Sirolimus," pp. 1-13, available online at http://en.wikipedia.org/wiki/Sirolimus, date accessed May 11, 2011.

Encyclopedia Britannica Online, "Surface Coating", available online at http://www.britannica.com/EBchecked/topic/575029/surface-coating>, date accessed Jun. 17, 2011.

Crivello et al., "Epoxidized triglycerides as renewable monomers in photoinitiated cationic polymerization," Chem. Mater, 1992:692-699.

Timir-Balizsy et al., "Chemical Principals of Textile Conservation," Oxford: Elsevier Science Ltd., 1998:117-119.

International Search Report for International Application PCT/US05/034601, dated Apr. 10, 2006.

International Search Report for International Application PCT/US05/034610, dated Mar. 16, 2006.

International Search Report for International Application PCT/US05/034614, dated Aug. 29, 2006.

International Search Report for International Application PCT/US05/034615, dated May 16, 2006.

International Search Report for International Application PCT/US05/034678, dated Aug. 28, 2006.

International Search Report for International Application PCT/US05/034681, dated Jul. 26, 2006.

International Search Report for International Application PCT/US05/034682, dated Jul. 20, 2006.

International Search Report for International Application PCT/US05/034836, dated Jul. 6, 2006.

International Search Report for International Application PCT/US05/034941, dated May 4, 2006.

International Search Report for International Application PCT/US06/037184, dated Feb. 22, 2007.

International Preliminary Report on Patentability for International Application PCT/US06/040753, dated Oct. 3, 2008.

International Search Report for International Application PCT/US06/040753, dated Sep. 24, 2007.

International Search Report for International Application PCT/US07/019978, dated May 7, 2009.

International Search Report for International Application PCT/US07/022860, dated Apr. 22, 2009.

International Search Report for International Application PCT/US07/022944, dated Apr. 8, 2009.

International Search Report for International Application PCT/US08/000565, dated May 4, 2009.

International Preliminary Examination Report for International Application PCT/US08/071547, dated Aug. 26, 2010.

International Search Report for International Application PCT/US08/071547, dated Oct. 22, 2008.

International Preliminary Report on Patentability for International Application PCT/US08/071565, dated Aug. 27, 2009.

International Search Report for International Application PCT/US08/071565, dated Nov. 10, 2008.

International Search Report for International Application PCT/US08/085386, dated Feb. 4, 2009.

International Search Report for International Application PCT/US09/037364, dated Aug. 27, 2009.

International Search Report for International Application PCT/US10/026521, dated Jun. 23, 2010.

International Search Report for International Application PCT/US10/052899, dated Jan. 10, 2011.

Supplementary European Search Report in Application No. EP 05 80 4291, dated Jul. 26, 2011.

Supplementary European Search Report for Application No. EP 05 80 2894, dated Jul. 27, 2011.

Supplementary European Search Report in Application No. EP 05 85 8430, dated Aug. 18, 2011.

Supplementary European Search Report in Application No. 05 800 844, dated Aug. 19, 2011.

Non-final Office Action for U.S. Appl. No, 11/236,908 (listed on SB/08 as US 2006/0067974), mailed Mar. 25, 2006.

Final Office Action for U.S. Appl. No. 11/236,908 (listed on SB/08 as US 2006/0067974), mailed May 17, 2011.

Non-final Office Action for U.S. Appl. No. 11/236,908 (listed on SB/08 as US 2006/0067974), mailed Aug. 24, 2009.

Final Office Action for U.S. Appl. No. 11/236,943 (listed on SB/08 as US 2006/0067975), mailed Dec. 23, 2009.

Non-Final Office Action for U.S. Appl. No. 11/236,943 (listed on SB/08 as US 2006/0067975), mailed Mar. 5, 2009.

Non-final Office Action for U.S. Appl. No. 11/236,977 (listed on SB/08 as US 2006/0088596), mailed Aug. 3, 2009.

Final Office Action for U.S. Appl. No. 11/237,263 (listed on SB/08 as US 2006/0110457), mailed Jul. 7, 2010.

Non-final Office Action for U.S. Appl. No. 11/237,263 (listed on SB/08 as US 2006/0110457), mailed Oct. 7, 2009.

Final Office Action for U.S. Appl. No. 11/237,264 (listed on SB/08 as US 2006/0067983), mailed Jun. 2, 2010.

Non-final Office Action for U.S. Appl. No. 11/237,264 (listed on SB/08 as US 2006/0067983), mailed Oct. 5, 2009.

Final Office Action for U.S. Appl. No. 11/701,799 (listed on SB/08 as US 2008/0109017), mailed Nov. 23, 2010.

Non-final Office Action for U.S. Appl. No. 11/237,420 (listed on SB/08 as US 2006/0078586), mailed Mar. 5, 2009.

Final Office Action for U.S. Appl. No. 11/237,420 (listed on SB/08 as US 2006/0078586), mailed Nov. 4, 2009.

Non-final Office Action for U.S. Appl. No. 11/237,420 (listed on SB/08 as US 2006/0078586), mailed Dec. 6, 2010.

Non-final Office Action for U.S. Appl. No. 11/238,532 (listed on SB/08 as US 2006/0067976), mailed Mar. 30, 2009.

Final Office Action for U.S. Appl. No. 11/238,532 (listed on SB/08 as US 2006/0067976), mailed Sep. 9, 2009.

Final Office Action for U.S. Appl. No. 11/238,554 (listed on SB/08 as US 2006/0121081), mailed May 12, 2010.

Non-final Office Action for U.S. Appl. No. 11/238,554 (listed on SB/08 as US 2006/0121081), mailed Oct. 9, 2009.

Final Office Action for U.S. Appl. No. 11/238,554 (listed on SB/08 as US 2006/0121081), mailed May 1, 2009.
Non-final Office Action for U.S. Appl. No. 11/238,554 (listed on SB/08 as US 2006/0121081), mailed Jul. 25, 2008.
Non-final Office Action for U.S. Appl. No. 11/238,564 (listed on SB/08 as US 2006/0083768), mailed Apr. 16, 2008.
Final Office Action for U.S. Appl. No. 11/238,564 (listed on SB/08 as US 2006/0083768), mailed Aug. 6, 2009.
Non-final Office Action for U.S. Appl. No. 11/239,555 (listed on SB/08 as US 2006/0067977), mailed Mar. 30, 2009.
Non-final Office Action for U.S. Appl. No. 11/525,328 (listed on SB/08 as US 2007/0084144), mailed Apr. 30, 2007.
Non-final Office Action for U.S. Appl. No. 11/525,390 (listed on SB/08 as US 2007/0071798), mailed Jul. 14, 2010.
Final Office Action for U.S. Appl. No. 11/525,390 (listed on SB/08 as US 2007/0071798), mailed Feb. 21, 2011.
Final Office Action for U.S. Appl. No. 11/582,135 (listed on SB/08 as US 2007/0202149), mailed May 12, 2011.
Non-final Office Action for U.S. Appl. No. 11/582,135 (listed on SB/08 as US 2007/0202149), mailed Nov. 9, 2010.
Non-final Office Action for U.S. Appl. No. 11/582,135 (listed on SB/08 as US 2007/0202149), mailed Jan. 6, 2010.
Non-final Office Action for U.S. Appl. No. 11/582,135 (listed on SB/08 as US 2007/0202149), mailed May 12, 2009.
Non-final Office Action for U.S. Appl. No. 11/701,799 (listed on SB/08 as US 2008/0109017), mailed Apr. 12, 2010.
Non-final Office Action for U.S. Appl. No. 11/978,840 (listed on SB/08 as US 2008/0118550), mailed Dec. 3, 2010.
Non-final Office Action for U.S. Appl. No. 11/980,155 (listed on SB/08 as US 2008/0113001), mailed Mar. 24, 2011.
Non-final Office Action for U.S. Appl. No. 12/075,223 (listed on SB/08 as US 2008/0206305), mailed Dec. 8, 2010.
Non-final Office Action for U.S. Appl. No. 12/325,546 (listed on SB/08 as US 2009/0181937.), mailed Feb. 25, 2010.
Final Office Action for U.S. Appl. No. 12/325,546 (listed on SB/08 as US 2009/0181937.), mailed Aug. 31, 2010.
Non-final Office Action for U.S. Appl. No. 12/364,763 (listed on SB/08 as US 2009/0208552.), mailed Dec. 11, 2009.
Final Office Action for U.S. Appl. No. 12/364,763 (listed on SB/08 as US 2009/0208552.), mailed Sep. 21, 2010.
Interview summary for U.S. Appl. No. 11/236,908 (listed on SB/08 as US 2006/0067974) mailed May 5, 2009.
Interview summary for U.S. Appl. No. 11/236,908 (listed on SB/08 as US 2006/0067974) mailed Dec. 2, 2010.
Interview summary for U.S. Appl. No. 11/237,420 (listed on SB/08 as US 2006/0078586) mailed May 5, 2009.
Interview summary for U.S. Appl. No. 11/582,135 (listed on SB/08 as US 2007/0202149) mailed Dec. 7, 2010.
Interview summary for U.S. Appl. No. 12/325,546 (listed on SB/08 as US 2009/0181937) mailed Dec. 2, 2010.
Interview summary for U.S. Appl. No. 12/364,763 (listed on SB/08 as US 2009/0208552) mailed Dec. 2, 2010.
Final Office Action for U.S. Appl. No. 11/978,840 (listed on SB/08 as US 2008/0118550.), mailed Jun. 22, 2011.
Non-final Office Action for U.S. Appl. No. 11/525,390 (listed on SB/08 as US 2007/0071798) mailed Jul. 11, 2011.
Final Office Action for U.S. Appl. No. 11/237,420 (listed on SB/08 as US 2006/0078586), mailed Jul. 13, 2011.
Final Office Action for U.S. Appl. No. 12/075,223 (listed on SB/08 as US 2008/0206305.), mailed Aug. 11, 2011.
Non-Final Office Action for U.S. Appl. No. 11/701,799 (listed on SB/08 as US 2008/0109017), mailed Aug. 17, 2011.
Non-Final Office Action for U.S. Appl. No. 11/582,135 (listed on SB/08 as US 2007/0202149), mailed Oct. 14, 2011.
Final Office Action for U.S. Appl. No. 11/980,155 (listed on SB/08 as US 2008/0113001), mailed Oct. 21, 2011.
Non-Final Office Action for U.S. Appl. No. 11/236,908 (listed on SB/08 as US 2006/0067974), mailed Dec. 2, 2011.
Non-Final Office Action for U.S Appl. No. 12/182,261 (listed on SB/08 as US 2009/0047414), mailed Dec. 21, 2011.
Non-Final Office Action for U.S. Appl. No. 12/401,243 (listed on SB/08) as US 2010/0233232, mailed Jan. 5, 2012.
Notice of Allowance for U.S. Appl. No. 11/582,135 (listed on SB/08 as US 2007/0202149), mailed Jan. 9, 2012.
Non-Final Office Action for U.S. Appl. No. 12/182,165 (listed on SB/08 as US 2009/0011116), mailed Jan. 5, 2012.
Final Office Action for U.S. Appl. No. 11/701,799 (listed on SB/08 as US 2008/0109017), mailed Feb. 13, 2012.
Non-Final Office Action for U.S. Appl. No. 12/581,582 (listed on SB-08 as US 2010-0183697) mailed Mar. 14, 2012.
Final Office Action for U.S. Appl. No. 12/185,165 (listed on SB-08 as US 2009-0011116) mailed Apr. 6, 2012.
Ahuja et al. Journal of Indian Pediatric Surgery 2002 7:15-20.
Websters Dictionary Online, Accessed on Feb. 13, 2009, entry for "polymer" p. 1 of 1.
International Search Report for International Application No. PCT/US05/34941, dated May 4, 2006.
International Search Report for PCT/US2011/44292, dated Dec. 6, 2011.
Final Office Action for U.S. Appl. No. 12/401,243 (listed on SB/08 as US- 2010-0233232), mailed Jun. 11, 2012.
Notice of Allowance for U.S. Appl. 12/182,261 (listed on SB/08 as US US-2009-0047414), mailed Jul. 23, 2012.
Supplementary European Search Report for Application No. EP 08877338.7, dated Aug. 16, 2012.
Supplementary European Search Report for Application No. EP09819594.4, dated Aug. 14, 2012.
Advisory Action for U.S. Appl. No. 12/401,243 (listed on SB/08 as US 2010-0233232), mailed Aug. 27, 2012.
Final Office Action for U.S. Appl. No. 12/581,582 (listed on SB-08 as US 2010/0183697) mailed Aug. 29, 2012.
Notice of Allowance for U.S. Appl. No. 11/525,390 (listed on SB/08 as US-2007/0071798), mailed Oct. 4, 2012.
Advisory Action for U.S. Appl. No. 12/581,582 (listed on SB/08 as US 2010-0183697), mailed Nov. 14, 2012.
Notice of Allowance for U.S. Appl. No. 11/525,390 (listed on SB/08 as US-2007/0071798), mailed Nov. 20, 2012.
Notice of Allowance for U.S. Appl. No. 11/525,390 (listed on SB/08 as US-2007/0071798), mailed Nov. 30, 2012.
Non-final Office Action for U.S. Appl. No. 13/184,512 (listed on SB/08 as US 2012-0016038), mailed Jan. 31, 2013.
Non-final Office Action for U.S. Appl. No. 11/978,840 (listed on SB/08 as US 2008/0118550), mailed Feb. 19, 2013.
Non-Final Office Action for U.S. Appl. No. 13/682,991, mailed Mar. 18, 2013.

* cited by examiner

Carbon-Carbon (C-C) Cross-linking of Fatty Acid Chains

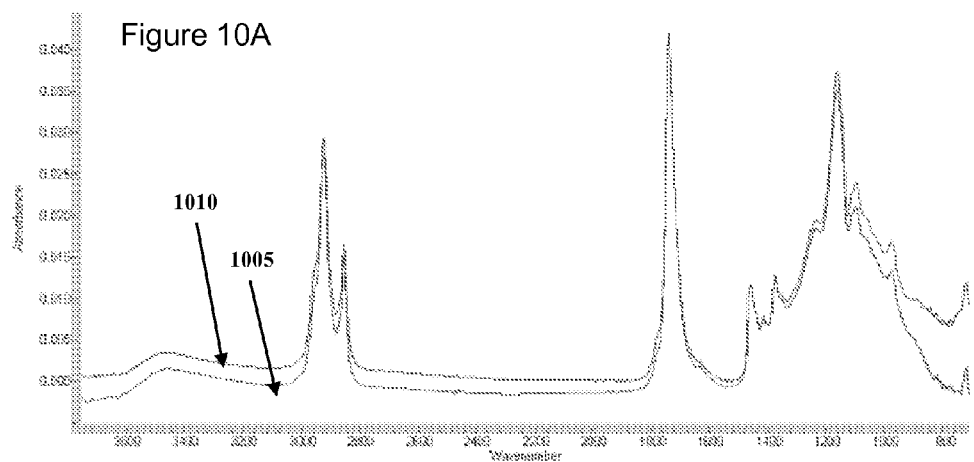
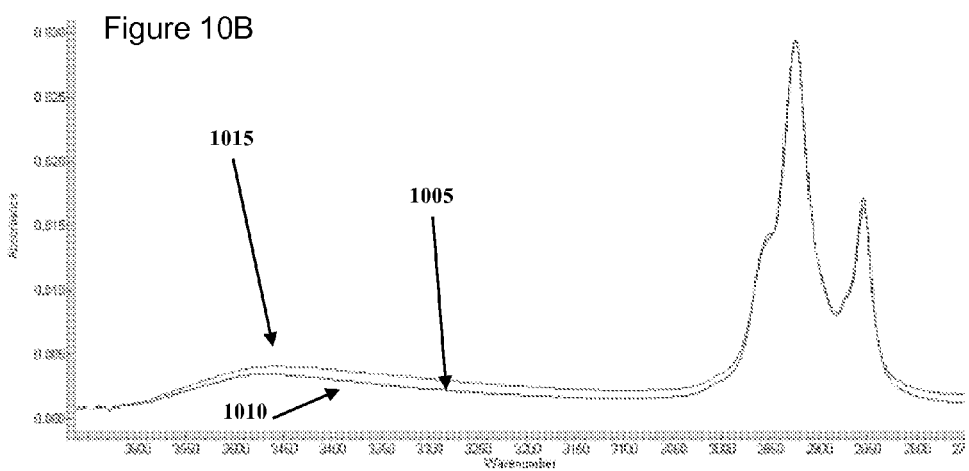
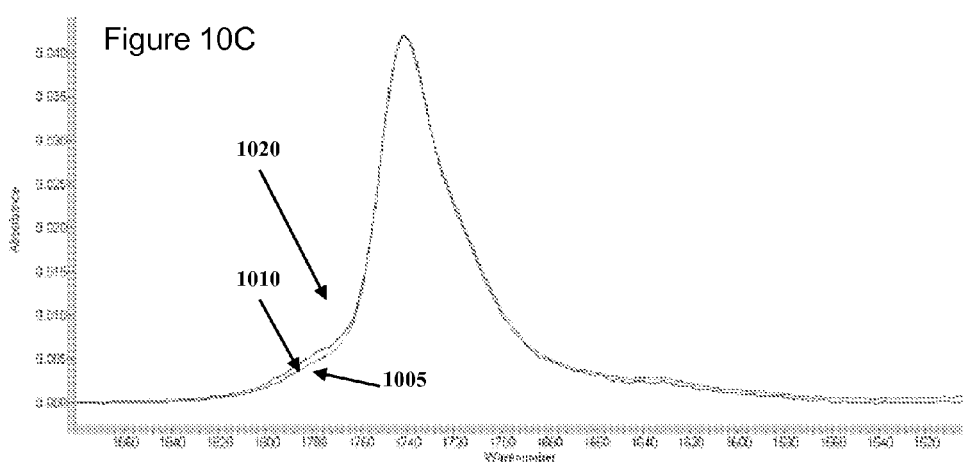

HYDROPHOBIC CROSS-LINKED GELS FOR BIOABSORBABLE DRUG CARRIER COATINGS

RELATED APPLICATIONS

This application is a continuation of U.S. application Ser. No. 11/582,135, filed on Oct. 16, 2006 (issuing as U.S. Pat. No. 8,124,127 on Feb. 28, 2012), which claims priority to U.S. Provisional Patent Application Ser. No. 60/727,312, filed on Oct. 15, 2005, the entire contents of which are hereby incorporated herein by reference.

BACKGROUND OF THE INVENTION

Vascular procedures, such as vascular reperfusion procedures, balloon angioplasty, and mechanical stent deployment, can often result in vascular injury following mechanical dilation and luminal expansion of a narrowed vessel. Often, subsequent to such intravascular procedures, neointimal proliferation and vascular injury remodeling occurs along the luminal surface of the injured blood vessel; more specifically, remodeling occurs in the heart, as well as in vulnerable peripheral blood vessels like the carotid artery, iliac artery, femoral and popliteal arteries. No known mechanical suppression means has been found to prevent or suppress such cellular proliferation from occurring immediately following vascular injury from mechanical reperfusion procedures. Left untreated, restenosis within the vessel lumen within weeks of a vascular injury can occur. Restenosis results in re-narrowing of the vessel lumen, causing massive fibrin and platelet deposition and uncontrolled cellular remodeling, which leads to restricted blood flow and thrombosis of the luminal surface. Restenosis pre-disposes the patient to a totally occluded and/or critical ischemic event with morbidity.

Restenosis initiated by vascular injury cellular remodeling can be a gradual process. Multiple processes, including fibrin and platelet deposition, luminal thrombosis, inflammation, calcineurin activation, growth factor and cytokine release, cell proliferation, cell migration and extracellular matrix synthesis each contribute to the restenotic process. While the exact mechanism of restenosis is not completely understood, several suspected biochemical pathways involved in cell inflammation, growth factor stimulation and fibrin and platelet deposition have been postulated. Cell derived growth factors such as platelet derived growth factor, fibroblast growth factor, epidermal growth factor, thrombin, etc., released from platelets, invading macrophages and/or leukocytes, or directly from the smooth muscle cells, provoke proliferative and migratory responses in medial smooth muscle cells. These cells undergo a change from the contractile phenotype to a synthetic phenotype. Proliferation/migration usually begins within one to two days post-injury and peaks several days thereafter. In the normal arterial wall, smooth muscle cells proliferate at a low rate, approximately less than 0.1 percent per day.

However, daughter cells migrate to the intimal layer of arterial smooth muscle and continue to proliferate and secrete significant amounts of extracellular matrix proteins. Proliferation, migration and extracellular matrix synthesis continue until the damaged endothelial layer is repaired, at which time proliferation slows within the intima, usually within seven to fourteen days post-injury. The newly formed tissue is called neointima. The further vascular narrowing that occurs over the next three to six months is due primarily to negative or constrictive remodeling.

Simultaneous with local proliferation and migration, inflammatory cells derived from the medial layer of the vessel wall continually invade and proliferate at the site of vascular injury as part of the healing process. Within three to seven days post-injury, substantial inflammatory cell formation and migration have begun to accumulate along the vessel wall to obscure and heal over the site of the vascular injury. In animal models, employing either balloon injury or stent implantation, inflammatory cells may persist at the site of vascular injury for at least thirty days. Inflammatory cells may contribute to both the acute and protracted chronic phases of restenosis and thrombosis.

Today, a preferred approach to the local delivery of a drug to the site of vascular injury caused by an intravascular medical device, such as a coronary stent, is to place a drug eluting coating on the device. Clinically, medical devices coated with a drug eluting coating comprised of either a permanent polymer or degradable polymer and an appropriate therapeutic agent, have shown angiographic evidence that vascular wall proliferation following vascular injury and/or vascular reperfusion procedures can be reduced if not eliminated for a certain period of time subsequent to balloon angioplasty and/or mechanical stent deployment. Local delivery of a single sirolimus or taxol compound via a drug eluting medical device has been shown to be effective at minimizing or preventing cellular proliferation and cellular remodeling when applied immediately after vascular injury. Various analogs of these two anti-proliferative compound examples have also been shown experimentally and clinically to exhibit similar anti-proliferative activity with similar drug eluting coatings. However, anti-proliferative compounds such as sirolimus and taxol, together with a polymeric drug eluting coating have also been shown clinically to exhibit a number of toxic side effects, during and after principal drug release from the drug eluting coating. These chronic and or protracted side effects place limits on the amount of drug that can actually be delivered over a given period of time, as well as challenge the compatibility of the polymer coatings used to deliver a therapeutic agent locally to the site of the vascular injury when applied directly to a site of inflammation and or cellular remodeling. In addition, local overdosage of compound like sirolimus and taxol can prevent, limit or even stop cellular remodeling or proliferation in and around the localized tissue area of the medical device. For example, a lack of endothelial cell coverage during the interruption of cell proliferation thought the vascular injury healing process exhibits a high potential for luminal thrombosis whereby fibrin and a constant deposition of platelets blanket the exposed and non-healed medical device and/or damaged vascular injury. Without uninterrupted systemic support or administration of an anti-platelet medication like clopidegrel combined with an anti-clotting agent, such as ASA, prior to and following deployment of a drug eluting medical device, such devices have been shown clinically to thrombose and occlude within days of deployment. In addition, although these commercially available drug eluting polymer coatings employed on medical devices are generally characterized as being biocompatible, the lack of chemical breakdown, degradation and absorption of these polymer-based chemistries into smaller, easier to metabolize chemical components or products have been now been clinically demonstrated to initiate a protracted localized inflammatory response at the site of the vascular injury, which may lead to unexpected thromobotic occlusion within days of stopping anti-platelet medication.

Wound healing or response to in-vivo injury follows the same general biological cascade as in vascular injury. Namely, inflammation of native tissue followed by migration and proliferation of cells to mitigate the inflammatory response; including platelets and macrophages; and subsequent healing phase which includes fibrin deposition and tissue remodeling.

The sustained nature of the thrombotic and inflammatory response to injury makes it desirable to provide localized drug delivery coatings that can release the one or more therapeutic agents over a period of time in order to minimize such cell activated response, and to reduce the potential toxic side effects of many drugs makes it desirable to provide alternative non-polymeric, bioabsorbable carrier that delivers the drug via a bioabsorbable mechanism.

SUMMARY OF THE INVENTION

What is desired is a drug delivery coating that can release and deliver a therapeutic agent in a sustained and preferably controlled fashion to the local tissue, without chronic inflammation due to either the therapeutic agent or break-down products of the coating. The present invention is directed toward various solutions that facilitate addressing this need.

What is also desired is a coating that can be bioabsorbed by cells and that can deliver a drug without inducing chronic localized inflammation to tissues (e.g., vascular tissue) that has been injured mechanically or by reperfusion injury, whereby the coating and the therapeutic agent are ingested and metabolized by the cell, as it consumes the breakdown products of the coating with the drug.

In various aspects, the present inventions provide methods for producing hydrophobic, non-polymeric cross-linked gel coatings comprising one or more therapeutic agents that facilitate the controlled loading of the one or more of therapeutic agent, sustained release of a therapeutic agent, and controlled release of a therapeutic agent the coating is ingested and absorbed. In various embodiments, provided are methods of tailoring the drug release profile of a hydrophobic, non-polymeric cross-linked gel by control of the curing conditions used to produce the cross-linked gel from a natural oil containing starting material; the use of a free radical scavenger in a natural oil containing starting material from which the gel is formed, or combinations thereof. In various embodiments, the methods of the present invention tailor the drug release properties of a hydrophobic, non-polymeric cross-linked gel coating by controlling the degree of cross-linking in the gel. In various embodiments, the methods of the present invention tailor the drug delivery properties of a hydrophobic, non-polymeric cross-linked gel coating by controlling the level of fatty acids, tocopherols and soluble components in the cross-linked gel.

In various aspects, the present inventions provide hydrophobic, non-polymeric cross-linked gel coatings comprising one or more therapeutic agents with a tailored release profile for one or more of the therapeutic agents. In various embodiments, the tailored release profile comprises a sustained release profile. In various embodiments, the tailored release profile properties are controlled by the level of fatty acids, tocopherols and soluble components in the cross-linked gel. In various aspects of the present invention, the bio-absorbable cross-linked gel contains fatty acids, many of which originate as triglycerides. It has previously been demonstrated that triglyceride byproducts, such as partially hydrolyzed triglycerides and fatty acid molecules can integrate into cellular membranes and enhance the solubility of drugs into the cell. Whole triglycerides are known not to enhance cellular uptake as well as partially hydrolyzed triglyceride, because it is difficult for whole triglycerides to cross cell membranes due to their relatively larger molecular size. Vitamin E compounds can also integrate into cellular membranes resulting in decreased membrane fluidity and cellular uptake.

In various aspects, the present inventions provide a hydrophobic cross linked gel containing fatty acids and alpha-tocopherol in differing amounts and ratios to contribute to a cross-linked gel in a manner that provides control over the cellular uptake characteristics of the cross-linked gel and any therapeutic agents mixed therein.

In various aspects, the present inventions provide coated medical devices having a non-polymeric bio-absorbable drug release coating comprising one or more layers of hydrophobic cross-linked gel, wherein at least one of the cross-linked gel layers contains one or more therapeutic agents. In various embodiments, the drug release coating does not substantially decompose, in vivo, into either lactic acids or glycolic acid compounds. In various embodiments, the drug release coating hydrolyzes in vivo, into substantially non-inflammatory compounds. In various embodiments, the coated medical device is implantable in a patient to effect long term local delivery of the therapeutic agent to the patient. In various embodiments the delivery is at least partially characterized by the total and relative amounts of the therapeutic agent released over time. In various embodiments, the tailored delivery profile is controlled by the level of soluble components in the cross-linked gel. In various embodiments, the delivery profile is a function of the solubility and lipophilicity of the coating components and therapeutic agent in-vivo.

In various embodiments, the present inventions provide coatings where the drug release profile of the coating is tailored through the provision of two or more coatings and selection of the location of the therapeutic agent. The drug location can be altered, e.g., by coating a bare portion of a medical device with a first starting material and creating a first cured coating, then coating at least a portion of the first cured-coating with the drug-oil formulation to create a second overlayer coating. The first starting material can comprise one or more therapeutic agents. In various embodiments, the second overlayer coating is also cured. The drug load, drug release profiles and/or drug delivery of the first coating, the overlay coating, or both, can be tailored through the use of different curing conditions and/or addition of free radical scavengers (e.g., vitamin E), as described herein.

It is to be understood that the process of providing two layers, can be extended to provide three or more layers, wherein at least one of the layers comprises a hydrophobic, non-polymeric cross-linked gel. In addition, one or more of the layers can be drug releasing, and the drug release profile of such layers can be tailored using the methods described herein.

In accordance with various embodiments of the present invention, the hydrophobic, non-polymeric, cross-linked gel contains lipids. The hydrophobic cross-linked gel is formed from a naturally occurring oil, such as fish oil, starting material. The hydrophobic cross-linked gel can contain omega-3 fatty acids. The hydrophobic cross-linked gel can also contain alpha-tocopherol or vitamin E.

The coatings of the present invention can be formulated to contain a variety of other chemicals and entities in addition to a therapeutic agent, including, but not limited to, one or more of: a pharmaceutically acceptable carrier, an excipient, a surfactant, a binding agent, an adjuvant agent, and/or a stabilizing agent (including preservatives, buffers and antioxidants).

In one embodiment, alpha-tocopherol TPGS may be added to the coatings of the present invention.

In various aspects, the present inventions provide methods for treating injury in a mammal, such as, e.g., a human. In various embodiments, the injury is a vascular injury. In various embodiments, the methods comprise locally administering one or more therapeutic agents in a therapeutically effective amount by sustained release of the one or more therapeutic agents from a coating comprising a hydrophobic, non-polymeric cross-linked gel.

The teachings herein demonstrate that cured fish oil soft tissue mesh coatings can allow for the ability to regulate the release profile of drug-loaded fish oil-based coatings from implantable devices. In various embodiments, the release profile can be controlled through changes in oil coating chemistry by varying coating composition and cure times. The teachings demonstrate that hydrophobic, non-polymeric cross-linked gels produced by 150° F. curing for 3 days possess less peroxide/ether/carbon-carbon cross-links than those cured at 200° F. curing for 24 hours. The teachings demonstrate that the cross-linking and gelation of the cured fish oil coatings can be directly dependent on the formation of hydroperoxides in the fish oil component, which increases with increasing temperature. Dissolution experiments presented herein have shown that drug release and coating degradation are more rapid for the cross-linked coatings produced using 150° F. curing conditions as compared to those created employing the 200° F. curing conditions.

The teachings herein demonstrate that the use of vitamin E in cured fish oil coatings is another method to alter the cross-linking and drug release properties of the coating. Vitamin E is an antioxidant that can slow down autoxidation in fish oil by reducing, it is believed, hydroperoxide formation during curing. This can result in a decrease in the amount of cross-linking observed in a cured fish oil coating. Increasing the amount of vitamin E in the coating can result in lengthening and slowing the release of a therapeutic agent from the coating. For example, the teachings herein demonstrate a lengthening and slowing of the release of the rapamycin, from a hydrophobic, non-polymeric cross-linked gel coating into a dissolution buffer, due, it is believed, to rapamycin's affinity for the fatty acid and vitamin E components in the cured fish oil coating. The teachings herein further indicate that vitamin E can also results in protecting a drug such as rapamycin and increase the amount of such drug extracted from the coating.

The teachings herein also demonstrate that the positioning of the drug-containing layer on a coated medical device can alter the release profile of the coating.

BRIEF DESCRIPTION OF THE DRAWINGS

The foregoing and other aspects, embodiments, objects, features and advantages of the invention can be more fully understood from the following description in conjunction with the accompanying drawings. In the drawings, like reference characters generally refer to like features and structural elements throughout the various figures. The drawings are not necessarily to scale, emphasis instead being placed upon illustrating the principles of the invention.

FIGS. 10A-C are an FTIR spectra comparison of the coating cured at 150° F. for 3 days and the coating cured at 200° F. for 24 hours;

DETAILED DESCRIPTION

Figure 1:
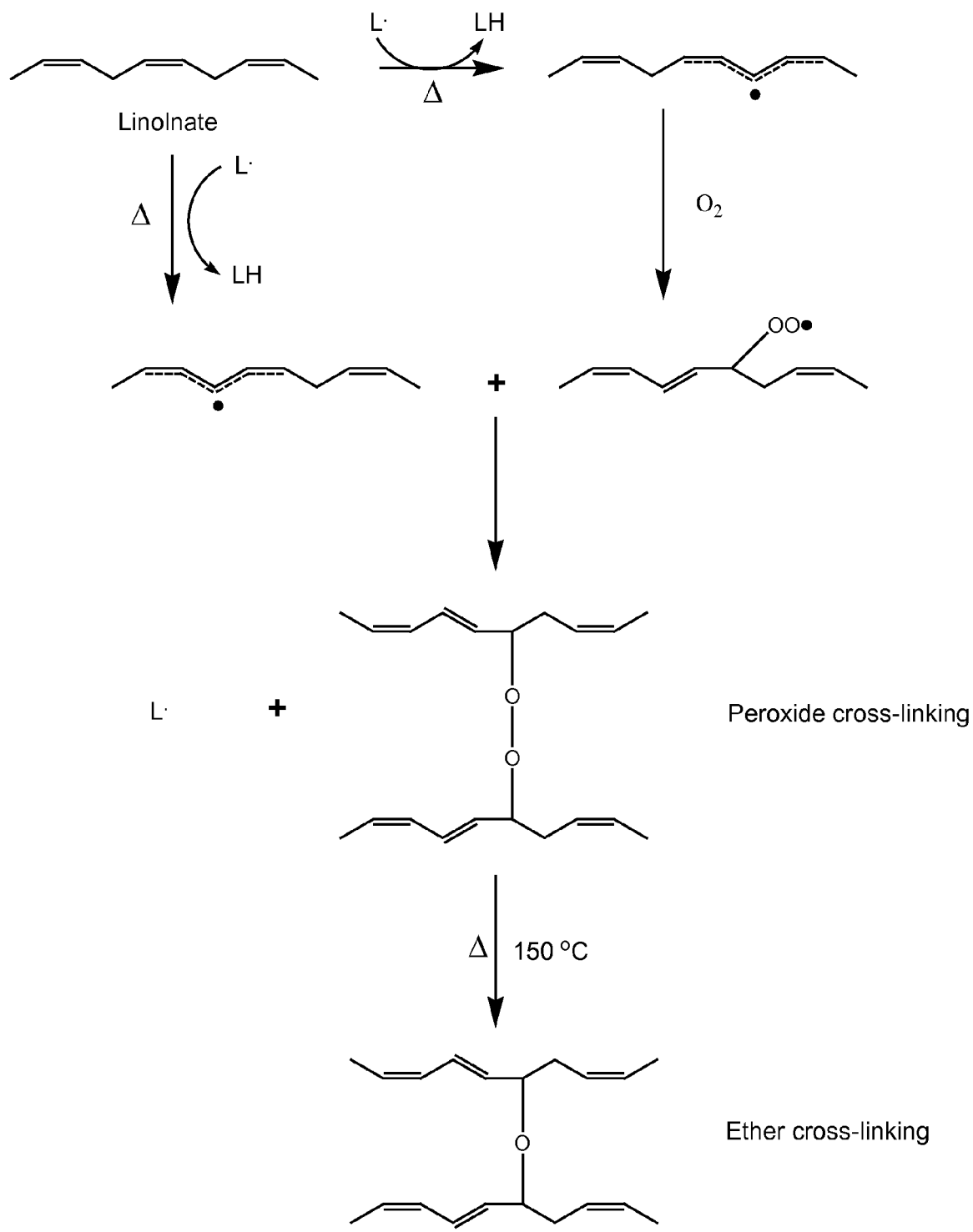
FIG. 1 is a schematic illustration of an example of the creation of peroxide and ether cross-linking in a polyunsaturated oil.

The present inventions are directed towards coatings for medical devices for release and local delivery of one or more therapeutic agents, methods of forming and tailoring the properties of said coatings and methods of using said coatings for treating injury in a mammal.

Prior to further describing the invention, it may be helpful to an understanding thereof to generally and briefly describe injury and the biological response thereto.

Vascular Injury

Vascular injury causing intimal thickening can be broadly categorized as being either biologically or mechanically induced. Biologically mediated vascular injury includes, but is not limited to, injury attributed to infectious disorders including endotoxins and herpes viruses, such as cytomegalovirus; metabolic disorders, such as atherosclerosis; and vascular injury resulting from hypothermia, and irradiation. Mechanically mediated vascular injury includes, but is not limited to, vascular injury caused by catheterization procedures or vascular scraping procedures, such as percutaneous transluminal coronary angioplasty; vascular surgery, transplantation surgery; laser treatment; and other invasive procedures which disrupt the integrity of the vascular intima or endothelium. Generally, neointima formation is a healing response to a vascular injury.

Inflammatory Response

Wound healing upon vascular injury occurs in several stages. The first stage is the inflammatory phase. The inflammatory phase is characterized by hemostasis and inflammation. Collagen exposed during wound formation activates the clotting cascade (both the intrinsic and extrinsic pathways), initiating the inflammatory phase. After injury to tissue occurs, the cell membranes, damaged from the wound formation, release thromboxane A2 and prostaglandin 2-alpha, which are potent vasoconstrictors. This initial response helps to limit hemorrhage. After a short period, capillary vasodilatation occurs secondary to local histamine release, and the cells of inflammation are able to migrate to the wound bed. The timeline for cell migration in a normal wound healing process is predictable. Platelets, the first response cell, release multiple chemokines, including epidermal growth factor (EGF), fibronectin, fibrinogen, histamine, platelet-derived growth factor (PDGF), serotonin, and von Willebrand factor. These factors help stabilize the wound through clot formation. These mediators act to control bleeding and limit the extent of injury. Platelet degranulation also activates the complement cascade, specifically C5a, which is a potent chemoattractant for neutrophils.

As the inflammatory phase continues, more immune response cells migrate to the wound. The second response cell to migrate to the wound, the neutrophil, is responsible for debris scavenging, complement-mediated opsonization of bacteria, and bacteria destruction via oxidative burst mechanisms (i.e., superoxide and hydrogen peroxide formation). The neutrophils kill bacteria and decontaminate the wound from foreign debris.

The next cells present in the wound are the leukocytes and the macrophages (monocytes). The macrophage, referred to as the orchestrator, is essential for wound healing. Numerous enzymes and cytokines are secreted by the macrophage. These include collagenases, which debride the wound; interleukins and tumor necrosis factor (TNF), which stimulate fibroblasts (produce collagen) and promote angiogenesis; and transforming growth factor (TGF), which stimulates keratinocytes. This step marks the transition into the process of tissue reconstruction, i.e., the proliferative phase.

Cell Proliferation

The second stage of wound healing is the proliferative phase. Epithelialization, angiogenesis, granulation tissue formation, and collagen deposition are the principal steps in this anabolic portion of wound healing. Epithelialization occurs early in wound repair. At the edges of wounds, epidermis immediately begins thickening. Marginal basal cells begin to migrate across the wound along fibrin strands stopping when they contact each other (contact inhibition). Within the first 48 hours after injury, the entire wound is epithelialized. Layering of epithelialization is re-established. The depths of the wound at this point contain inflammatory cells and fibrin strands. Aging effects are important in wound healing as many, if not most, problem wounds occur in an older population. For example, cells from older patients are less likely to proliferate and have shorter life spans and cells from older patients are less responsive to cytokines.

Heart disease can be caused by a partial vascular occlusion of the blood vessels that supply the heart, which is preceded by intimal smooth muscle cell hyperplasia. The underlying cause of the intimal smooth muscle cell hyperplasia is vascular smooth muscle injury and disruption of the integrity of the endothelial lining. Intimal thickening following arterial injury can be divided into three sequential steps: 1) initiation of smooth muscle cell proliferation following vascular injury, 2) smooth muscle cell migration to the intima, and 3) further proliferation of smooth muscle cells in the intima with deposition of matrix. Investigations of the pathogenesis of intimal thickening have shown that, following arterial injury, platelets, endothelial cells, macrophages and smooth muscle cells release paracrine and autocrine growth factors (such as platelet derived growth factor, epidermal growth factor, insulin-like growth factor, and transforming growth factor) and cytokines that result in the smooth muscle cell proliferation and migration. T-cells and macrophages also migrate into the neointima. This cascade of events is not limited to arterial injury, but also occurs following injury to veins and arterioles.

Granulomatous Inflammation

Chronic inflammation, or granulomatous inflammation, can cause further complications during the healing of vascular injury. Granulomas are aggregates of particular types of chronic inflammatory cells which form nodules in the millimeter size range. Granulomas may be confluent, forming larger areas. Essential components of a granuloma are collections of modified macrophages, termed epithelioid cells, usually with a surrounding zone of lymphocytes. Epithelioid cells are so named by tradition because of their histological resemblance to epithelial cells, but are not in fact epithelial; they are derived from blood monocytes, like all macrophages. Epithelioid cells are less phagocytic than other macrophages and appear to be modified for secretory functions. The full extent of their functions is still unclear. Macrophages in granulomas are commonly further modified to form multinucleate giant cells. These arise by fusion of epithelioid macrophages without nuclear or cellular division forming huge single cells which may contain dozens of nuclei. In some circumstances the nuclei are arranged round the periphery of the cell, termed a Langhans-type giant cell; in other circumstances the nuclei are randomly scattered throughout the cytoplasm (i.e., the foreign body type of giant cell which is formed in response to the presence of other indigestible foreign material in the tissue). Areas of granulomatous inflammation commonly undergo necrosis.

Formation of granulomatous inflammation seems to require the presence of indigestible foreign material (derived from bacteria or other sources) and/or a cell-mediated immune reaction against the injurious agent (type IV hypersensitivity reaction).

Drug Release and Delivery Coatings

The coatings of the present invention comprise a hydrophobic non-polymeric cross-linked gel, one or more therapeutic agents, and a fatty acid. In a further embodiment, the coating comprises the hydrophobic non-polymeric cross-linked gel and a fatty acid, and further comprises one or more of the group consisting of a glyceride, a glycerol, and a fatty alcohol and also may further comprise a therapeutic agent.

The coating can comprise both soluble and insoluble components. As used in the context of the cross-linked gel coating described herein, the terms "soluble" and "insoluble" refer the solubility of the coating in a polar solvent such as, e.g., tetrahydrofuran (THF), e.g., as determined by gravimetric analysis. For example, the coatings may be about 60%-75% soluble in THF and about 25%-40% insoluble in THF, or alternatively, the coatings may be about 30%-55% soluble in THF and 45%-70% insoluble in THF, as determined by gravimetric analysis. Generally, at least some of the components resistant to extraction in organic solvent (such as THF) may include cross linked components, which may comprise free or esterified fatty acids with chain lengths of about $C_{10}$-$C_{22}$.

It should be noted that the term cross-linked gel, as utilized herein with reference to the present invention, refers to a gel that is non-polymeric and is derived from an oil composition comprising molecules covalently cross-linked into a three-dimensional network by one or more of ester, ether, peroxide, and carbon-carbon bonds in a substantially random configuration. In various preferred embodiments, the oil composition comprises a fatty acid molecule, a glyceride, and combinations thereof.

In addition, the hydrophobic non-polymeric cross-linked gel coatings of the present invention are bioabsorbable as described herein. The therapeutic agent can be an active agent as contained in the coating and/or a prodrug that, e.g., becomes active once released from the coating. The coating may be selected such that it delivers or releases the therapeutic agent at a desired rate and/or therapeutically effective rate in vivo. In another embodiment, the coating may have an average drug loading of about 1-50% by weight.

The hydrophobic non-polymeric cross-linked gel coatings of the present inventions are formed from an oil component. The term "oil component" is also referred to herein as the "oil-containing starting material." The "oil-containing starting material" may be natural or derived from synthetic sources. Preferably, the "oil containing starting material" comprises unsaturated fatty acids. The oil component can be either an oil, or an oil composition. The oil component can be a naturally occurring oil, such as fish oil, cod liver oil, cranberry oil, a synthetic oil, or other oils having desired characteristics. One example embodiment of the present invention makes use of a fish oil in part because of the high content of omega-3 fatty acids, which can provide healing support for damaged tissue, as discussed herein. The fish oil can also serve as an anti-adhesion agent. In addition, the fish oil maintains anti-inflammatory or non-inflammatory properties as well. The present invention is not limited to formation of the hydrophobic non-polymeric cross-linked gel coating with fish oil as the naturally occurring oil. However, the following description makes reference to the use of fish oil as one example embodiment. Other naturally occurring oils or synthetic oils can be utilized in accordance with the present invention as described herein.

It should be noted that as utilized herein, the terms "fish oil" includes but is not limited to omega-3 fatty acid, fish oil fatty acid, free fatty acid, monoglycerides, di-glycerides, or triglycerides, esters of fatty acids, or a combination thereof. The fish oil may include one or more of arachidic acid, gadoleic acid, arachidonic acid, eicosapentaenoic acid, docosahexaenoic acid or derivatives, analogs and pharmaceutically acceptable salts thereof.

Furthermore, as utilized herein, the term free fatty acid includes but is not limited to one or more of butyric acid, caproic acid, caprylic acid, capric acid, lauric acid, myristic acid, palmitic acid, palmitoleic acid, stearic acid, oleic acid, vaccenic acid, linoleic acid, alpha-linolenic acid, gamma-linolenic acid, behenic acid, erucic acid, lignoceric acid, analogs and pharmaceutically acceptable salts thereof. The naturally occurring oils, including fish oil, are cured as described herein to form a hydrophobic cross-linked gel, creating the coating.

With regard to the aforementioned oils, it is generally known that the greater the degree of unsaturation in the fatty acids the lower the melting point of a fat, and the longer the hydrocarbon chain the higher the melting point of the fat. A polyunsaturated fat, thus, has a lower melting point, and a saturated fat has a higher melting point. Those fats having a lower melting point are more often oils at room temperature. Those fats having a higher melting point are more often waxes or solids at room temperature. Therefore, a fat having the physical state of a liquid at room temperature is an oil. In general, polyunsaturated fats are liquid oils at room temperature, and saturated fats are waxes or solids at room temperature.

Polyunsaturated fats are one of four basic types of fat derived by the body from food. The other fats include saturated fat, as well as monounsaturated fat and cholesterol. Polyunsaturated fats can be further composed of omega-3 fatty acids and omega-6 fatty acids. Under the convention of naming, the unsaturated fatty acid according to the position of its first double bond of carbons, those fatty acids having their first double bond at the third carbon atom from the methyl end of the molecule are referred to as omega-3 fatty acids. Likewise, a first double bond at the sixth carbon atom is called an omega-6 fatty acid. There can be both monounsaturated and polyunsaturated omega fatty acids.

Omega-3 and omega-6 fatty acids are also known as essential fatty acids because they are important for maintaining good health, despite the fact that the human body cannot make them on its own. As such, omega-3 and omega-6 fatty acids must be obtained from external sources, such as food. Omega-3 fatty acids can be further characterized as containing eicosapentaenoic acid (EPA), docosahexanoic acid (DHA), and alpha-linolenic acid (ALA). Both EPA and DHA are known to have anti-inflammatory effects and wound healing effects within the human body.

As utilized herein, the term "bio-absorbable" generally refers to having the property or characteristic of being able to penetrate the tissue of a patient's body. In certain embodiments of the present invention bio-absorption occurs through a lipophilic mechanism. The bio-absorbable substance can be soluble in the phospholipid bi-layer of cells of body tissue, and therefore impact how the bio-absorbable substance penetrates into the cells.

It should be noted that a bio-absorbable substance is different from a biodegradable substance. Biodegradable is generally defined as capable of being decomposed by biological agents, or capable of being broken down by microorganisms or biological processes. Biodegradable substances can cause inflammatory response due to either the parent substance or those formed during breakdown, and they may or may not be absorbed by tissues. Some biodegradable substances are limited to bulk erosion mechanism for breakdown.

Examples of medical devices that may be coated with the coatings of the invention include, but are not limited to, stents, catheter balloons, surgical mesh and encapsulated surgical mesh.

Drug Release and Delivery

The coatings of the present invention deliver one or more therapeutic agents locally to a targeted area using a medical device or apparatus bearing the coating at a selected targeted tissue location of the patient that requires treatment. The therapeutic agent is transferred along with the coating to the targeted tissue location. The combined release and local delivery of a therapeutic agent enables a more concentrated and higher quantity of therapeutic agent via lipophilic coating components independent of diffusion to be delivered directly at the targeted tissue location, without having broader systemic side effects. With local delivery, the therapeutic agent that escapes the targeted tissue location dilutes as it travels to the remainder of the patient's body, substantially reducing or eliminating systemic side effects.

Targeted local therapeutic agent delivery using a medical device can be further broken into two categories, namely, short term and long term. The short term delivery of a therapeutic agent occurs generally within a matter of seconds or minutes to a few days or weeks. The long term delivery of a therapeutic agent occurs generally within weeks to months.

The phrase "sustained release" as used herein generally refers to the release of a biologically active agent that results in the long term delivery of the active agent.

The phrase "controlled release" as used herein generally refers to the release of a biologically active agent in a substantially predictable manner over the time period of weeks or months, as desired and predetermined upon formation of the biologically active agent on the medical device from which it is being released. Controlled release includes the provision of an initial burst of release upon implantation, followed by the substantially predictable release over the aforementioned time period.

Examples of therapeutic agents which may advantageously be administered through sustained release include anti-proliferative and anti-inflammatory agents. These agents will be loaded into the coating at drug loading level which may affect the rate of their release. The amount of drug released over a particular time frame can be tailored to particular classes of drugs, particular drugs, particular diseases and particular subjects.

For example, for one anti-proliferative drug, the coating may have an average drug loading of about 500 to about 1500 micrograms per square inch, about 600 to about 1450 micrograms per square inch, about 700 to about 1400 micrograms per square inch, about 800 to about 1350 micrograms per square inch, about 900 to about 1300 micrograms per square inch, about 1000 to about 1300 micrograms per square inch, or about 1100 to about 1300 micrograms per square inch (after curing). Furthermore, the coating may release the drug over a period of at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, or at least about 20 days. In a further embodiment, the coating releases the drug over a period of about 17 to about 20 days.

For another therapeutic agent, such as an anti-proliferative drug, the coating may have an average drug loading of about 200 to about 800 micrograms per square inch, about 300 to about 700 micrograms per square inch, about 400 to about 600 micrograms per square inch, or about 400 to about 500 micrograms per square inch (after curing). Furthermore, the coating may release the drug over a period of at least about 10 days, at least about 15 days, at least about 20 days, at least about 25 days, at least about 30 days, at least about 35 days, at least about 40 days, or at least about 45 days. In a further embodiment, the coating releases the drug over a period of about 35 to about 45 days.

For another therapeutic agent, such as an anti-inflammatory agent, the coating may have an average drug loading of about 50 to about 600 micrograms per square inch, about 75 to about 500 micrograms per square inch, about 100 to about 400 micrograms per square inch, or about 150 to about 350 micrograms per square inch (after curing). Furthermore, the coating may release the drug over a period of at least about 5 days, at least about 6 days, at least about 7 days, at least about 8 days, at least about 9 days, at least about 10 days, at least about 11 days, at least about 12 days, at least about 13 days, at least about 14 days, or at least about 15 days. In a further embodiment, the coating releases the drug over a period of about 10 to about 15 days.

For another therapeutic agent, such as an anti-inflammatory agent, the coating may have an average drug loading of about 200 to about 800 micrograms per square inch, about 300 to about 700 micrograms per square inch, about 400 to about 600 micrograms per square inch, or about 400 to about 500 micrograms per square inch (after curing). Furthermore, the coating may release the drug over a period of at least about 10 days, at least about 15 days, at least about 20 days, at least about 25 days, at least about 30 days, at least about 35 days, at least about 40 days, or at least about 45 days. In a further embodiment, the coating releases the drug over a period of about 25 to about 30 days.

Drug Release Mechanisms

Prior attempts to create coatings, films and drug delivery platforms, such as in the field of stents, primarily make use of high molecular weight synthetic polymer based materials to provide the ability to better control the release of the therapeutic agent. Essentially, the polymer in the platform releases the drug or agent via diffusion based mechanism at a predetermined rate once implanted at a location within the patient. Regardless of how much of the therapeutic agent would be most beneficial to the damaged tissue, the polymer releases the therapeutic agent based on properties of the polymer, e.g., erosion of the polymeric material and drug diffusion out of the solid matrix. Accordingly, the effect of the therapeutic agent is substantially local at the surface of the tissue making contact with the medical device having the coating. In some instances the effect of the therapeutic agent is further localized to the specific locations of, for example, stent struts or mesh pressed against the tissue location being treated. These prior approaches can create the potential for a concentrated localized toxic effect.

In various embodiments of the present inventions, the coatings release and deliver one or more therapeutic agents by a dissolution mechanism, e.g., dissolution of a therapeutic agent contained in a soluble component of the coating into the medium in contact with the coating, e.g., tissue, in addition to a bioabsorption based transfer mechanism. As a result, the drug release mechanism can be based on the solubility of the therapeutic agent in the surrounding medium. For example, a therapeutic agent near the interface between the hydrophobic coating and the surrounding medium can experience a chemical potential gradient which can motivate the therapeutic agent out of the oil based coating and into solution in the surrounding medium. Accordingly, in various embodiments, the release of a therapeutic agent is not rate-limited by the break-down or erosion of the coating, but is due to the enhanced bioabsorption of the therapeutic agent in the presence of lipophilic gel components.

In various embodiments, the in vivo by-products of the hydrophobic, non-polymeric cross-linked gel convert into non-inflammatory byproducts, e.g., free fatty acids and glycerols, that themselves can release and deliver one on or more of the therapeutic agents via a dissolution mechanism.

Not to be limited by theory, in certain embodiments of the present invention, the components of the gel (such as fatty acids) may act as "a carrier" of the therapeutic agent directly into the cell and tissue as the fatty acid groups become metabolized by the cell and cell membrane. In certain embodiments, it has been shown that the coating is drawn off the medical device and absorbed nearly intact, in small fatty acid groups with the therapeutic agent contained therein, without substantial release of the therapeutic agent into bodily fluids.

In one embodiment, the coating of the invention does not substantially release the therapeutic agent (e.g., into body fluids) but is directly transferred to the local tissue that is in contact with the coating, e.g., through a physiochemical lipophilic attraction mechanism and subsequent cell uptake of the fatty acid complex. Lipophilic transference and cell uptake may be controlled chemically by, for example, adding uptake enhancers, varying the amount of curing, varying drug loading to alter viscosity, or other chemically modifying means, so as to modulated drug release into body fluids. Not to be limited by theory, but the transference of the coating onto localized tissue may maximize the drug distribution to the cells of the proximate tissue. In addition, this mechanism of transference and cell medicated uptake is believed not to induce substantial inflammation.

With the present invention, and in the field of soft tissue applications, and in part because of the lipophilic mechanism enabled by the bio-absorbable lipid based cross-linked gel of the present invention, the uptake of the therapeutic agent is facilitated by the delivery of the therapeutic agent to the cell membrane by the bio-absorbable cross-linked gel. Further, the therapeutic agent is not freely released into the body fluids, but rather, is delivered directly to the cells and tissue. In prior configurations using polymer based coatings, the drugs were released at a rate regardless of the reaction or need for the drug on the part of the cells receiving the drug.

Therapeutic Agents

As utilized herein, the phrase "therapeutic agent(s)" refers to a number of different drugs or agents available, as well as future agents that may be beneficial for use with the drug release coatings of the present invention, and may be used interchangeable with the term "drug." The therapeutic agent component can take a number of different forms including anti-oxidants, anti-inflammatory agents, anti-coagulant agents, drugs to alter lipid metabolism, anti-proliferatives, anti-neoplastics, tissue growth stimulants, functional protein/factor delivery agents, anti-infective agents, anti-imaging agents, anesthetic agents, therapeutic agents, tissue absorption enhancers, anti-adhesion agents, germicides, anti-septics, analgesics, prodrugs thereof, and any additional desired therapeutic agents such as those listed in Table 1 below.

TABLE 1

| CLASS | EXAMPLES |
|---|---|
| Antioxidants | Alpha-tocopherol, lazaroid, probucol, phenolic antioxidant, resveretrol, AGI-1067, vitamin E |
| Antihypertensive Agents | Diltiazem, nifedipine, verapamil |
| Antiinflammatory Agents | Glucocorticoids (e.g. dexamethazone, methylprednisolone), leflunomide, NSAIDS, ibuprofen, acetaminophen, hydrocortizone acetate, hydrocortizone sodium phosphate, macrophage-targeted bisphosphonates |
| Growth Factor Antagonists | Angiopeptin, trapidil, suramin |
| Antiplatelet Agents | Aspirin, dipyridamole, ticlopidine, clopidogrel, GP IIb/IIIa inhibitors, abcximab |
| Anticoagulant Agents | Bivalirudin, heparin (low molecular weight and unfractionated), wafarin, hirudin, enoxaparin, citrate |
| Thrombolytic Agents | Alteplase, reteplase, streptase, urokinase, TPA, citrate |
| Drugs to Alter Lipid Metabolism (e.g. statins) | Fluvastatin, colestipol, lovastatin, atorvastatin, amlopidine |
| ACE Inhibitors | Elanapril, fosinopril, cilazapril |
| Antihypertensive Agents | Prazosin, doxazosin |
| Antiproliferatives and Antineoplastics | Cyclosporine, cochicine, mitomycin C, sirolimus micophenonolic acid, rapamycin, everolimus, tacrolimus, paclitaxel, QP-2, actinomycin, estradiols, dexamethasone, methatrexate, cilostazol, prednisone, cyclosporine, doxorubicin, ranpirnas, troglitzon, valsarten, pemirolast, C-MYC antisense, angiopeptin, vincristine, PCNA ribozyme, 2-chloro-deoxyadenosine, mTOR targeting compounds |
| Tissue growth stimulants | Bone morphogeneic protein, fibroblast growth factor |
| Promotion of hollow organ occlusion or thrombosis | Alcohol, surgical sealant polymers, polyvinyl particles, 2-octyl cyanoacrylate, hydrogels, collagen, liposomes |
| Functional Protein/Factor delivery | Insulin, human growth hormone, estradiols, nitric oxide, endothelial progenitor cell antibodies |
| Second messenger targeting | Protein kinase inhibitors |
| Angiogenic | Angiopoetin, VEGF |
| Anti-Angiogenic | Endostatin |
| Inhibition of Protein Synthesis/ECM formation | Halofuginone, prolyl hydroxylase inhibitors, C-proteinase inhibitors |
| Antiinfective Agents | Penicillin, gentamycin, adriamycin, cefazolin, amikacin, ceftazidime, tobramycin, levofloxacin, silver, copper, hydroxyapatite, vancomycin, ciprofloxacin, rifampin, mupirocin, RIP, kanamycin, brominated furonone, algae byproducts, bacitracin, oxacillin, nafcillin, floxacillin, clindamycin, cephradin, neomycin, methicillin, oxytetracycline hydrochloride, Selenium. |
| Gene Delivery | Genes for nitric oxide synthase, human growth hormone, antisense oligonucleotides |
| Local Tissue perfusion | Alcohol, $H_2O$, saline, fish oils, vegetable oils, liposomes |
| Nitric oxide Donor Derivatives | NCX 4016 - nitric oxide donor derivative of aspirin, SNAP |
| Gases | Nitric oxide, compound solutions |
| Imaging Agents | Halogenated xanthenes, diatrizoate meglumine, diatrizoate sodium |

TABLE 1-continued

| CLASS | EXAMPLES |
|---|---|
| Anesthetic Agents | Lidocaine, benzocaine |
| Descaling Agents | Nitric acid, acetic acid, hypochlorite |
| Anti-Fibrotic Agents | Interferon gamma-1b, Interluekin-10 |
| Immunosuppressive/Immuno modulatory Agents | Cyclosporine, rapamycin, mycophenolate motefil, leflunomide, tacrolimus, tranilast, interferon gamma-1b, mizoribine, mTOR targeting compounds |
| Chemotherapeutic Agents | Doxorubicin, paclitaxel, tacrolimus, sirolimus, fludarabine, ranpirnase |
| Tissue Absorption Enhancers | Fish oil, squid oil, omega 3 fatty acids, vegetable oils, lipophilic and hydrophilic solutions suitable for enhancing medication tissue absorption, distribution and permeation |
| Anti-Adhesion Agents | Hyaluronic acid, human plasma derived surgical sealants, and agents comprised of hyaluronate and carboxymethylcellulose that are combined with dimethylaminopropyl, ethylcarbodimide, hydrochloride, PLA, PLGA |
| Ribonucleases | Ranpirnase |
| Germicides | Betadine, iodine, sliver nitrate, furan derivatives, nitrofurazone, benzalkonium chloride, benzoic acid, salicylic acid, hypochlorites, peroxides, thiosulfates, salicylanilide |
| Antiseptics | Selenium |
| Analgesics | Bupivicaine, naproxen, ibuprofen, acetylsalicylic acid |

Some specific examples of therapeutic agents useful in the anti-restenosis realm include cerivastatin, cilostazol, fluvastatin, lovastatin, paclitaxel, pravastatin, rapamycin, a rapamycin carbohydrate derivative (for example, as described in US Patent Application Publication 2004/0235762), a rapamycin derivative (for example, as described in U.S. Pat. No. 6,200, 985), everolimus, seco-rapamycin, seco-everolimus, and simvastatin. With systemic administration, the therapeutic agent is administered orally or intravenously to be systemically processed by the patient. However, there are drawbacks to a systemic delivery of a therapeutic agent, one of which is that the therapeutic agent travels to all portions of the patient's body and can have undesired effects at areas not targeted for treatment by the therapeutic agent. Furthermore, large doses of the therapeutic agent only amplify the undesired effects at non-target areas. As a result, the amount of therapeutic agent that results in application to a specific targeted location in a patient may have to be reduced when administered systemically to reduce complications from toxicity resulting from a higher dosage of the therapeutic agent.

The therapeutic agent component, as described herein, has some form of therapeutic or biological effect. The oil component or oil composition component can also have a therapeutic or biological effect. Specifically, the cross-linked gel (and its oil constituents) enable the cells of body tissue of a patient to absorb the cross-linked gel 10 itself, rather than breaking down the gel and disbursing by-products of the gel for ultimate elimination by the patient's body.

The term "mTOR targeting compound" refers to any compound which modulates mTOR directly or indirectly. An example of an "mTOR targeting compound" is a compound that binds to FKBP 12 to form, e.g., a complex, which in turn inhibits phosphoinostide (PI)-3 kinase, that is, mTOR. In various embodiments, mTOR targeting compounds inhibit mTOR. Suitable mTOR targeting compounds include, for example, rapamycin and its derivatives, analogs, prodrugs, esters and pharmaceutically acceptable salts.

Calcineurin is a serine/threonine phospho-protein phosphatase and is composed of a catalytic (calcineurin A) and regulatory (calcineurin B) subunit (about 60 and about 18 kDa, respectively). In mammals, three distinct genes (A-alpha, A-beta, A-gamma) for the catalytic subunit have been characterized, each of which can undergo alternative splicing to yield additional variants. Although mRNA for all three genes appears to be expressed in most tissues, two isoforms (A-alpha and A-beta) are most predominant in brain.

The calcineurin signaling pathway is involved in immune response as well as apoptosis induction by glutamate excitotoxicity in neuronal cells. Low enzymatic levels of calcineurin have been associated with Alzheimer's disease. In the heart or in the brain calcineurin also plays a key role in the stress response after hypoxia or ischemia.

Substances which are able to block the calcineurin signal pathway can be suitable therapeutic agents for the present invention. Examples of such therapeutic agents include, but are not limited to, FK506, tacrolimus, cyclosporin and include derivatives, analogs, esters, prodrugs, pharmaceutically acceptably salts thereof, and conjugates thereof which have or whose metabolic products have the same mechanism of action. Further examples of cyclosporin include, but are not limited to, naturally occurring and non-natural cyclosporins prepared by total- or semi-synthetic means or by the application of modified culture techniques. The class comprising cyclosporins includes, for example, the naturally occurring Cyclosporins A through Z, as well as various non-natural cyclosporin derivatives, artificial or synthetic cyclosporin derivatives. Artificial or synthetic cyclosporins can include dihydrocyclosporins, derivatized cyclosporins, and cyclosporins in which variant amino acids are incorporated at specific positions within the peptide sequence, for example, dihydro-cyclosporin D.

In various embodiments, the therapeutic agent comprises one or more of a mTOR targeting compound and a calcineurin inhibitor. In various embodiments, the mTOR targeting compound is a rapamycin or a derivative, analog, ester, prodrug, pharmaceutically acceptably salts thereof, or conjugate thereof which has or whose metabolic products have the same mechanism of action. In various embodiments, the calcineurin inhibitor is a compound of Tacrolimus, or a derivative, analog, ester, prodrug, pharmaceutically acceptably salts thereof, or conjugate thereof which has or whose metabolic products have the same mechanism of action or a compound of Cyclosporin or a derivative, analog, ester, prodrug, pharmaceutically acceptably salts thereof, or conjugate thereof which has or whose metabolic products have the same mechanism of action. In certain embodiments, the therapeutic agents may cross link with the oil containing starting material. For example, therapeutic agents with unsaturations may cross link with the unsaturated fatty acids during the curing process. The gels, coatings, medical devices, and methods of the invention may comprise crosslinked fatty acids and therapeutic agents. Examples of therapeutic agents which may cross link include anthracyclines, rapamycins, etc.

Therapeutically Effective Amounts and Dosage Levels

A therapeutically effective amount refers to that amount of a compound sufficient to result in amelioration of symptoms, e.g., treatment, healing, prevention or amelioration of the relevant medical condition, or an increase in rate of treatment, healing, prevention or amelioration of such conditions. When applied to an individual active ingredient, administered alone, a therapeutically effective amount refers to that ingredient alone. When applied to a combination, a therapeutically effective amount can refer to combined amounts of the active ingredients that result in the therapeutic effect, whether administered in combination, serially or simultaneously. In various embodiments, where formulations comprise two or more therapeutic agents, such formulations can be described as a therapeutically effective amount of compound A for indication A and a therapeutically effective amount of compound B for indication B, such descriptions refer to amounts of A that have a therapeutic effect for indication A, but not necessarily indication B, and amounts of B that have a therapeutic effect for indication B, but not necessarily indication A.

Actual dosage levels of the active ingredients in a coating of the present invention may be varied so as to obtain an amount of the active ingredients which is effective to achieve the desired therapeutic response without being unacceptably toxic. The selected dosage level will depend upon a variety of pharmacokinetic factors including the activity of the particular therapeutic agent (drug) employed, or the ester, salt or amide thereof, the mechanism of drug action, the time of administration, the drug release profile of the coating, the rate of excretion of the particular compounds being employed, the duration of the treatment, other drugs, compounds and/or materials used in combination with the particular compounds employed, and like factors known in the medical arts.

Other Agents

The coatings of the present inventions can also comprise one or more other chemicals and entities in addition to the therapeutic agent, including, but not limited to, one or more of: a pharmaceutically acceptable carrier, an excipient, a surfactant, a binding agent, an adjuvant agent, and/or a stabilizing agent (including preservatives, buffers and antioxidants). The other agents can perform one or more functions, such as, e.g., an adjuvant may also serves as a stabilizing agent. In one embodiment, alpha-tocopherol TPGS is added to the coatings of the present invention. The preservative can also be useful in altering the physical properties of the oil component, as well as protecting some of the beneficial properties of the oil component during certain curing processes. Such beneficial properties include the healing and anti-inflammatory characteristics previously mentioned.

In various embodiments, the coatings of the present invention include one or more of a free radical scavenger and uptake enhancer. In various embodiments, the coatings comprise vitamin E.

As previously stated, and in accordance with embodiments of the present invention, the cross-linked gel is formed of a naturally occurring oil, or composition including a naturally occurring oil, such as fish oil, cod liver oil, cranberry oil, and the like. A characteristic of the naturally occurring oil is that the oil includes lipids, which contributes to the lipophilic action described later herein, that is helpful in the delivery of therapeutic agents to the cells of the body tissue. In addition, the naturally occurring oil can include the essential omega-3 fatty acids in accordance with several embodiments of the present invention.

It should be noted that as utilized herein to describe the present invention, the term vitamin E and the term alpha-tocopherol, are intended to refer to the same or substantially similar substance, such that they are interchangeable and the use of one includes an implicit reference to both. Further included in association with the term vitamin E are such variations including, but not limited to, one or more of alpha-tocopherol, beta-tocopherol, delta-tocopherol, gamma-tocopherol, alpha-tocotrienol, beta-tocotrienol, delta-tocotrienol, gamma-tocotrienol, alpha-tocopherol acetate, beta-tocopherol acetate, gamma-tocopherol acetate, delta-tocopherol acetate, alpha-tocotrienol acetate, beta-tocotrienol acetate, delta-tocotrienol acetate, gamma-tocotrienol acetate, alpha-tocopherol succinate, beta-tocopherol succinate, gamma-tocopherol succinate, delta-tocopherol succinate, alpha-tocotrienol succinate, beta-tocotrienol succinate, delta-tocotrienol succinate, gamma-tocotrienol succinate, mixed tocopherols, vitamin E TPGS, derivatives, analogs and pharmaceutically acceptable salts thereof.

Compounds that move too rapidly through a tissue may not be effective in providing a sufficiently concentrated dose in a region of interest. Conversely, compounds that do not migrate into a tissue may never reach the region of interest. Cellular uptake enhancers such as fatty acids and cellular uptake inhibitors such as alpha-tocopherol can be used alone or in combination to provide an effective transport of a given compound to a given region or location. Both fatty acids and alpha-tocopherol can be included in the drug release coatings of the present invention described herein. Accordingly, fatty acids and alpha-tocopherol can be combined in differing amounts and ratios to contribute to a drug release coating in a manner that provides control over the cellular uptake characteristics of the coating and any therapeutic agents mixed therein.

For example, the amount of alpha-tocopherol can be varied in the coating. Alpha-tocopherol is known to slow autoxidation in fish oil by reducing hydroperoxide formation, which results in a decrease in the amount of cross-linking in cured fish oil. In addition alpha-tocopherol can be used to increase solubility of drugs in the fish oil forming the coating. In various embodiments, alpha-tocopherol can actually protect the therapeutic drug during curing, which increases the resulting drug load in the coating after curing. Furthermore, with certain therapeutic drugs, the increase of alpha-tocopherol in the coating can serve to slow and extend drug release due to the increased solubility of the drug in the alpha-tocopherol component of the coating. This, combined with alpha-tocopherol's ability to decrease cell membrane permeability, reflects the cellular uptake inhibitor functionality of alpha-tocopherol, in that the delivery or uptake of the drug at the cellular level is slowed and extended over time.

Methods of Treating a Subject

The coatings, gels and medical devices of the present invention may be used to treat subjects. Examples of subjects include mammals, e.g., humans. The subjects may be suffering from a disorder such as, for example, vascular injury, soft tissue injury, or otherwise benefit from the use of one or more of the coatings, gels and/or medical devices of the invention.

In one embodiment, the invention pertains, at least in part, to a method for treating a subject. The method includes administering to the subject a medical device with a coating such that the subject is treated, wherein the coating comprises a hydrophobic, non-polymeric cross-linked gel, a fatty acid and a therapeutic agent.

In certain embodiments, the therapeutic agent is locally administered to the subject. The term "local administration" refers to the administration of the therapeutic agent generally to the tissue proximate to where the medical device is placed.

In another embodiment, the invention pertains to a method of administering a therapeutic agent to a target tissue in a subject. The method includes administering to the subject a hydrophobic, non-polymeric cross-linked gel and a therapeutic agent in proximity to the target tissue; and allowing the therapeutic agent to be bioabsorbed into the target tissue.

In another embodiment, the invention pertains, at least in part, to a method of administering a therapeutic agent to a target tissue in a subject. The method includes administering to the subject a medical device with a coating in proximity to the target tissue, wherein the coating comprises a hydrophobic, non-polymeric cross-linked gel and a therapeutic agent; and allowing the therapeutic agent to be bioabsorbed into the target tissue.

In a further embodiment, the therapeutic agent may be bioabsorbed by cellular uptake of the gel or coating. In another embodiment, the gel may be bioabsorbed by cellular uptake of the coating. In another embodiment, the therapeutic agent may be bioabsorbed in the presence of the gel.

Curing and Gel Formation

Several methods are available to cure the natural oil starting material containing one or more therapeutic agents to produce a non-polymeric cross-linked gel coating for a drug release and delivery coating in accordance with the present invention. Preferred methods for curing the starting material to produce a hydrophobic non-polymeric cross-linked gel coating of the present invention include, but are not limited to, heating (e.g., employing an oven, a broadband infrared (IR) light source, a coherent IR light source (e.g., laser), and combinations thereof) and ultraviolet (UV) irradiation. The starting material may be cross-linked through auto-oxidation.

Although some curing methods can have a have detrimental effects on a therapeutic agent combined with an omega-3 fatty acid oil starting material, one characteristic that can remain after certain curing by, e.g., heating and UV irradiation methods is the non-inflammatory response of the tissue when exposed to the cured omega-3 fatty acid material. As such, an oil containing omega-3 fatty acids can be heated, UV irradiated, or both, for curing purposes, and still maintain some or even a majority of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other coating materials.

In addition, some curing methods have been indicated to have detrimental effects on the therapeutic agent combined with the omega-3 fatty acid, making them partially or completely ineffective. As such, oils, and more specifically oils containing omega-3 fatty acids, have been utilized as a delivery agent for the short term uncontrolled release of a therapeutic agent, so that minimal or no curing is required. However, there are no known uses of oils containing omega-3 fatty acids for combination with a therapeutic agent in a controlled release application that makes use of the therapeutic benefits of the omega-3 fatty acids. Further, some heating of the omega-3 fatty acids to cure the oil can lessen the total therapeutic effectiveness of the omega-3 fatty acids, but not eliminate the therapeutic effectiveness. One characteristic that can remain after certain curing by heating methods is the non-inflammatory response of the tissue when exposed to the cured omega-3 fatty acid material. As such, an oil containing omega-3 fatty acids can be heated for curing purposes, and still maintain some or even a majority of the therapeutic effectiveness of the omega-3 fatty acids. In addition, although the therapeutic agent combined with the omega-3 fatty acid and cured with the omega-3 fatty acid can be rendered partially ineffective, the portion remaining of the therapeutic agent can, in accordance with the present invention, maintain pharmacological activity and in some cases be more effective than an equivalent quantity of agent delivered with other barrier or coating materials.

It should further be emphasized that the bio-absorbable nature of the cross-linked gel results in the cross-linked gel being completely absorbed over time by the cells of the body tissue. There are no substances in the cross-linked gel, or in vivo conversion by-products of the cross-linked gel, that induce an inflammatory response. The cross-linked gel is generally composed of, or derived from, omega-3 fatty acids bound to triglycerides, potentially also including a mixture of free fatty acids and vitamin E compounds (alpha-tocopherol). The triglycerides are broken down by lipases (enzymes) which result in free fatty acids that can than be transported across cell membranes. Subsequently, fatty acid metabolism by the cell occurs to metabolize any substances originating with the cross-linked gel. The bio-absorbable nature of the cross-linked gel of the present invention results in the cross-linked gel being absorbed over time, leaving only an underlying delivery or other medical device structure that is biocompatible. There is no foreign body inflammatory response to the bio-absorbable cross-linked gel.

Although the present invention is bio-absorbable to the extent that the cross-linked gel experiences the uptake into or through body tissues, in the specific embodiment described herein formed using naturally occurring oils, the exemplar oils are also lipid based oils. The lipid content of the oils provides a highly bio-absorbable cross-linked gel. More specifically, there is a phospholipids layer in each cell of the body tissue. The fish oil, and equivalent oils, contain lipids as well. There is a lipophilic action that results where the lipids are attracted by each other in an effort o escape the aqueous environment surrounding the lipids.

In accordance with various embodiments described herein, the coating component of the drug release coatings of the present invention is formed of a non-polymeric cross-linked gel, which can be derived from fatty acid compounds. The fatty acids include omega-3 fatty acids when the oil utilized to form the coating is fish oil or an analog or derivative thereof. As liquid fish oil is heated, autoxidation occurs with the absorption of oxygen into the fish oil to create hydroperoxides in an amount dependent upon the amount of unsaturated (C=C) sites in the fish oil. However, the (C=C) bonds are not consumed in the initial reaction. Concurrent with the formation of hydroperoxides is the isomerization of (C=C) double bonds from cis to trans in addition to double bond conjugation. It has been demonstrated that hydroperoxide formation increases with temperature. Heating of the fish oil allows for cross-linking between the fish oil unsaturated chains using a combination of peroxide (C—O—O—C), ether (C—O—C), and hydrocarbon (C—C) bridges. The formation of the cross-links results in gelation of the coating. The heating also can also result in the isomerization of cis (C=C) bonds into the trans configuration. The (C=C) bonds can also form C—C cross-linking bridges in the glyceride hydrocarbon chains using a Diels-Alder reaction. In addition to solidifying the coating through cross-linking, both the hydroperoxide and (C=C) bonds can undergo secondary reactions converting them into lower molecular weight secondary oxidation byproducts including aldehydes, ketones, alcohols, fatty acids, esters, lactones, ethers, and hydrocarbons.

UV initiated curing (photo-oxygenation) in accordance with the present invention involves the interaction between a double bond and singlet oxygen produced from ordinary triplet oxygen by light and typically in the presence of a sensitizer such as chlorophyll or methylene blue and results in the formation of hydroperoxides. The chemical reaction is described in the following graphic.

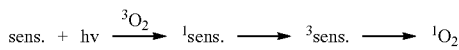

Since the above described reaction is not a radical chain process, it possesses no induction period and is typically unaffected by antioxidants commonly used to inhibit autoxidation. However, this reaction can be inhibited by single oxygen quenchers, such as carotene. This reaction is limited to C=C carbon atoms and results in a conversion from cis to trans C=C isomers during curing (as occurs with heat initiated curing). However, photo-oxygenation using UV is a relatively quicker reaction than autoxidation from heat curing, in the realm of about 1000-1500 times faster. The quicker reaction especially holds true for methylene interrupted polyunsaturated fatty acids, such as EPA and DHA, which are found in the fish oil based embodiments of the present invention.

An important aspect of UV curing when compared to heat curing is that although the byproducts obtained by both curing methods are similar, they are not necessarily identical in amount or chemical structure. One reason for this is due to the ability of photo-oxygenation to create hydroperoxides at more possible C=C sites as shown for linolenate in the below graphic.

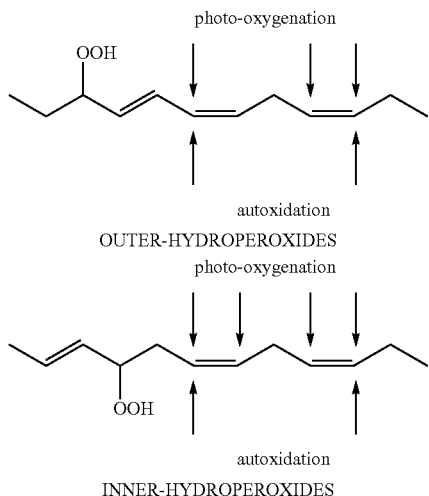

Photo-oxygenation, such as that which results from UV curing, due to its enhanced ability to create inner hydroperoxides, also results in the ability to form relatively greater amounts of cyclic byproducts, which also relates to peroxide cross-linking between fish oil hydrocarbon chains. For example, photo-oxygenation of linolenate results in 6 different types of hydroperoxides to be formed, whereas autoxidation results in only 4. The greater amount of hydroperoxides created using photo-oxygenation results in a similar, but slightly different, structure and amount of secondary byproducts to be formed relative to autoxidation from heat curing. Specifically, these byproducts are aldehydes, ketones, alcohols, fatty acids, esters, lactones, ethers, and hydrocarbons.

Figure 2:
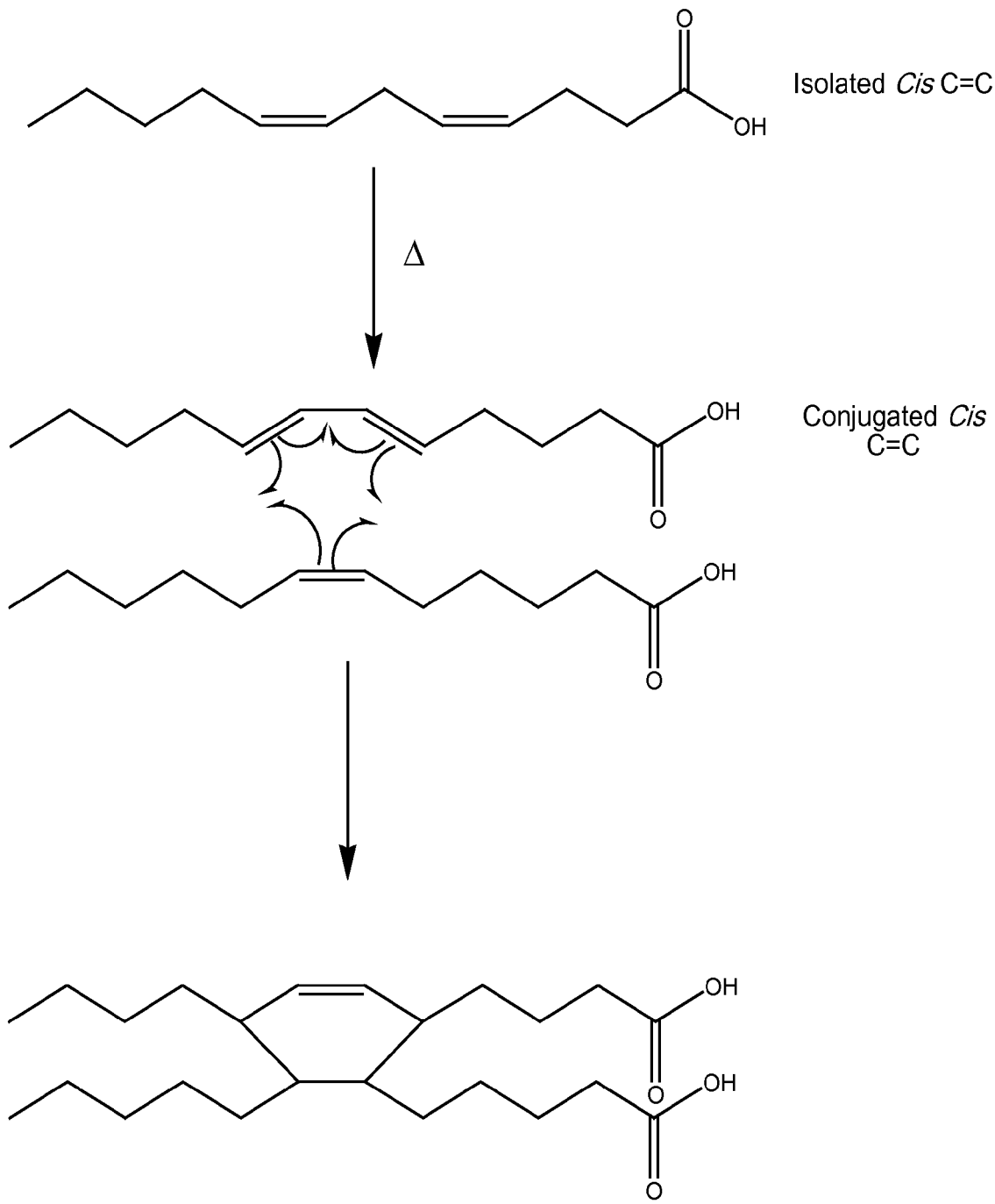
FIG. 2 is a schematic illustration of an example of the creation carbon-carbon cross-linking in a polyunsaturated oil (Diels-Alder type reaction)

Schematic illustrations of various cross-linking mechanisms and schemes are shown in FIGS. 1-2.

Accordingly, in various embodiments, the drug release coating of the present inventions comprise a non-polymeric cross-linked gel derived from fatty acid compounds, such as those of fish oil, that includes a cross-linked structure of triglyceride and fatty acid molecules in addition to free and bound glycerol, monoglyceride, diglyceride, and triglyceride, fatty acid, anhydride, lactone, aliphatic peroxide, aldehyde, and ketone molecules. It is believed that there are a substantial amount of ester bonds remaining after curing in addition to peroxide linkages forming the majority of the cross-links in the gel. The coating degrades (e.g., by hydrolysis) into fatty acid, short and long chain alcohol, and glyceride molecules, which are all non-inflammatory and likewise can be consumable by cells, such as, e.g., smooth muscle cells. Thus, the coating is bio-absorbable and degrades into substantially non-inflammatory compounds. The amount of cross linking may be modulated by adjusting the curing temperature, curing duration, amount of antioxidant, exposure to UV radiation or the presence of a drying oil.

Coating Bioabsorption

Figure 3:
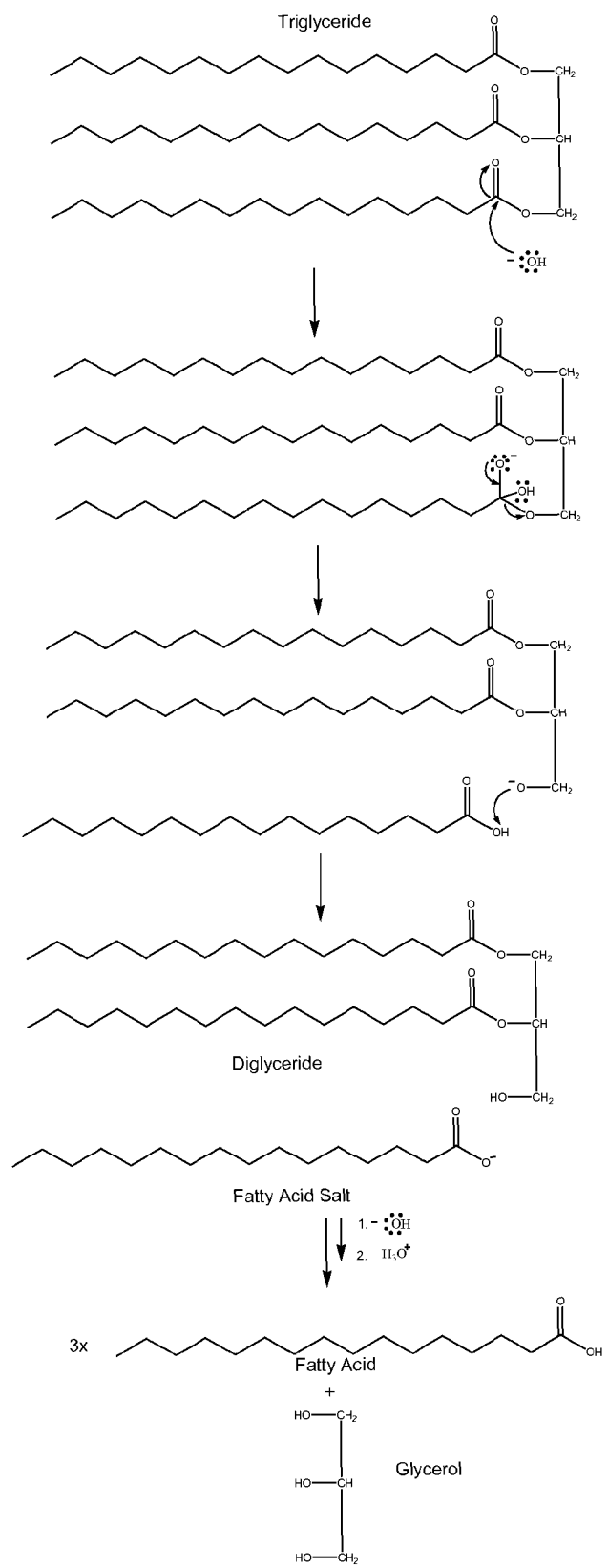
FIG. 3 schematically depicts the hydrolysis of the ester links in a triglyceride.

The bio-absorbable nature of the coating component of the drug release coatings of preferred embodiments of the present inventions results in the coating being completely absorbed over time by the cells of the body tissue. In various embodiments, there are substantially no substances in the coating, or in vivo conversion by-products of the coating, which induce an inflammatory response, e.g., the coating converts in vivo into non-inflammatory components. For example, in various embodiments, the coatings of the present invention upon conversion do not produce lactic acid and glycolic acid breakdown products in measurable amounts. The preferred coatings are generally composed of, or derived from, omega-3 fatty acids bound to triglycerides, potentially also including a mixture of free fatty acids and vitamin E (alpha-tocopherol). The triglycerides are broken down by lipases (enzymes) which result in free fatty acids that can than be transported across cell membranes. For example, FIG. 3 schematically depicts the base catalyzed hydrolysis of ester links in a triglyceride. Subsequently, fatty acid metabolism by the cell occurs to metabolize any substances originating with the coating. The bio-absorbable nature of the coating of the present invention results in the coating being absorbed over time, leaving only an underlying delivery or other medical device structure that is biocompatible. There is substantially no foreign body inflammatory response to the bio-absorbable coating or its break-downs products in the preferred embodiments of the present invention.

Tailoring of Drug and Delivery Profiles

In various aspects, the present invention provides methods of curing a fish oil coating to provide a non-polymeric cross-linked gel coating containing one or more therapeutic agents that can tailor the release and delivery profile of a therapeutic agent from the coating. The release profile can be tailored, e.g., through changes in oil coating chemistry by varying coating composition, temperature, and cure times. The position of the drug-containing layer on the coated device provides an additional mechanism to alter the release profile of the non-polymeric cross-linked gel coating. This can be achieved, e.g., by loading a drug into a cured base coating layer and coating a topcoat overlayer cured coating onto the previously cured encapsulating base layer.

An advantage of the cured fish oil coating in various embodiments of the present inventions is that the curing conditions utilized (i.e., cure time and temperature) can directly influence the amount of coating cross-linking density and byproduct formation, which in turn effects the coating bioabsorption. Thus, by altering the curing conditions employed, the release and delivery rate of a therapeutic compound of interest contained in the coating can also be altered. Examples of curing conditions include exposure of the material to a temperature of about 150-200° C. and/or ultra-violet light at a wavelength of about 254 nm.

In a various embodiments, an agent, such as, e.g., a free radical scavenger, can be added to the starting material to tailor the drug release profile of the non-polymeric cross-linked gel that is formed. In various embodiments, vitamin E is added to the starting material to, for example, to slow down autoxidation in fish oil by reducing hydroperoxide formation, which can result in a decrease in the amount of cross-linking observed in a cured fish oil coating. In addition, other agents can be used to increase the solubility of a therapeutic agent in the oil component of the starting material, protect the drug from degradation during the curing process, or both. For example vitamin E can also be used to increase the solubility of certain drugs in a fish oil starting material, and thereby facilitate tailoring the drug load of the eventual cured coating. Thus, varying the amount of vitamin E present in the coating provides an additional mechanism to alter the cross-linking and chemical composition of the non-polymeric cross-linked gel drug release and delivery coatings of the present invention.

In various embodiments, the present inventions provide coatings where the drug release profile of the coating is tailored through the provision of two or more coatings and selection of the location of the therapeutic agent. The drug location can be altered, e.g., by coating a bare portion of a medical device with a first starting material and creating a first cured coating, then coating at least a portion of the first cured coating with the drug-oil formulation to create a second overlayer coating. The first starting material can contain one or more therapeutic agents. In various embodiments, the second overlayer coating is also cured. The drug load, drug release profiles, and/or drug delivery of the first coating, the overlay coating, or both, can be tailored through the use of different curing conditions and/or addition of free radical scavengers (e.g., vitamin E), as described herein. The process of providing two layers, can be extended to provide three or more layers, wherein at least one of the layers comprises a hydrophobic, non-polymeric cross-linked gel. In addition, one or more of the layers can be release and deliver a drug, and the drug release profile of such layers can be tailored using the methods described herein.

In various embodiments, the present inventions provide release and delivery coatings where the drug release profile of the overall coating is tailored through the provision of two or more coating regions with different drug release profiles and selection of the location of the therapeutic agent. In various embodiments, the formation of different coating regions with different drug release properties is obtained by location specific curing conditions, e.g., location specific UV irradiation, and/or location specific deposition of a starting material on the coated device, e.g., by ink jet printing methods.

In an embodiment, the invention pertains, at least in part, to a method for tailoring a therapeutic agent release profile of a coating for a medical device. The method includes: combining the therapeutic agent with an oil-containing starting material to form a second material; selecting a curing condition such that an effective amount of said therapeutic agent will be released and delivered in an appropriate time period in vivo; and curing said second material according to said curing condition, such that therapeutic release and delivery profile is tailored. The method may further comprises the step of applying the second material to the medical device prior to curing.

The invention also pertains, at least in part, to a method for tailoring a therapeutic agent release profile of a coating for a medical device, by combining the therapeutic agent with an oil-containing starting material to form a second material; selecting a release rate controlling amount of vitamin E, such that an effective amount of the therapeutic agent is released in an appropriate time period; combining the second material with the vitamin E to form a third material; and at least partially curing the third material, such the therapeutic release and delivery profile is tailored. The method may further comprises the step of applying the third material to the medical device prior to curing.

The term "release rate controlling amount" includes the amount of Vitamin E which is sufficient to modulate the release of the therapeutic agent. In a further embodiment, the therapeutic agent is added to a mixture of about 1-20% vitamin E and 99-80% of a natural oil-containing starting material.

In another embodiment, the invention also comprises a method for tailoring a therapeutic agent release and delivery profile of a coating for a medical device. The method includes selecting a first curing condition; curing an oil-containing starting material according to the first curing condition to form a second material; combining the therapeutic agent with an oil-containing starting material to form a third material; combining the third material with the second material to form a fourth material; selecting a second curing condition; and at least partially curing the fourth material according to the second curing condition, such that therapeutic release and delivery profile is tailored. The method may further comprises the step of applying the fourth material to the medical device prior to curing.

In yet another embodiment, the invention also pertains, at least in part, to a method for tailoring a therapeutic agent release and delivery profile of a coating for a medical device. The method includes selecting a first curing condition; curing an oil-containing starting material according to the first curing condition to form a second material; combining the therapeutic agent with about 1-20% vitamin E and about 80-99% of a oil-containing starting material to form a third material; combining the third material with the second material to form a fourth material; selecting a second curing condition; and at least partially curing the fourth material according to the second curing condition. The method may further comprises the step of applying the fourth material to the medical device prior to curing.

In another embodiment, the invention pertains to a method for tailoring a therapeutic agent release and delivery profile of a coating for a medical device. The method includes curing an oil-containing starting material to form a second material; combining said therapeutic agent with an oil-containing starting material to form a third material; combining the third material with the second material to form a fourth material; selecting a curing condition such that an effective amount of the therapeutic agent is released in an appropriate time period; and curing the second material according to the curing condition.

In another embodiment, the invention pertains, at least in part, to a method for tailoring a therapeutic agent release and delivery profile of a coating for a medical device. The method includes curing a natural oil-containing starting material to form a second material; combining said therapeutic agent with 1-20% vitamin E and 99-80% of a natural oil-containing starting material to form a third material; combining the third material with the second material to form a fourth material; selecting a curing condition such that an effective amount of the therapeutic agent is released and delivered in an appropriate time period; and curing the second material according to the curing condition.

Coating Approaches and Methods for Coating Medical Devices

The invention, also pertains, at least in part, to methods for coating medical devices. The medical devices may release therapeutic agents at a desired rate.

In an embodiment, the invention pertains, at least in part, to a method for producing a coating for a medical device with a desired delivery and release rate of a therapeutic agent. The method includes combining the therapeutic agent with an oil-containing starting material to form a second material; selecting a curing condition based on the desired release rate; and curing the second material according to the selected curing condition, such that a desired drug delivery and release coating is produced.

In another embodiment, the invention pertains, at least in part, to a method for producing a coating for a medical device. The method includes: combining the therapeutic agent with an oil-containing starting material to form a second material; selecting a release rate controlling amount of vitamin E based on the desired release rate; combining the second material with the release rate controlling amount of vitamin E to form a third material; and at least partially curing the third material to form the coating.

In yet another embodiment, the invention also pertains to a method for producing a coating for a medical device. The method includes selecting a first curing condition; curing an oil-containing starting material according to the first curing condition to form a second material; combining the therapeutic agent with an oil-containing starting material to form a third material; combining the third material with the second material to form a fourth material; selecting a second curing condition; and at least partially curing the fourth material according to the second curing condition.

In yet another embodiment, the invention also pertains to another method for producing a coating for a medical device. The method includes: selecting a first curing condition; curing a natural oil-containing starting material according to the first curing condition to form a second material; combining the therapeutic agent with about 1-20% vitamin E and about 80-99% of an oil-containing starting material to form a third material; combining the third material with the second material to form a fourth material; selecting a second curing condition; and at least partially curing the fourth material according to the second curing condition.

In another embodiment, the invention also pertains to a method for producing a hydrophobic, non-polymeric cross-linked gel. The method includes combining a therapeutic agent with an oil-containing starting material to form a second material; and at least partially curing the second material.

Figure 4:
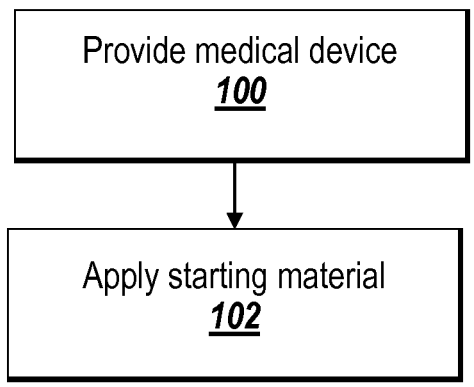
FIG. 4 is a flow chart illustrating a method of making the coated medical device of the present invention, in accordance with one embodiment of the present invention.

The methods of coating devices of the invention are further illustrated in the Figures. For example, FIG. 4 illustrates one method of making a medical device of the present invention, such as, e.g., a coated stent, in accordance with one embodiment of the present invention. The process involves providing a medical device, such as the stent (step 100). A coating of a starting material, which is to form a hydrophobic, non-polymeric cross-linked gel coating, is then applied to the medical device (step 102). One of ordinary skill in the art will appreciate that this basic method of application of a coating to a medical device, such as a stent, can have a number of different variations falling within the process described. The step of applying a coating substance to form a coating on the medical device can include a number of different application methods. For example, the medical device can be dipped into a liquid solution of the coating substance. The coating substance can be sprayed onto the device. Another application method is painting the coating substance on to the medical device. One of ordinary skill in the art will appreciate that other methods, such as electrostatic adhesion and other application methods, can be utilized to apply the coating substance to the medical device. Some application methods may be particular to the coating substance and/or to the structure of the medical device receiving the coating. Accordingly, the present invention is not limited to the specific embodiments of starting material application described herein, but is intended to apply generally to the application of the starting material which is to become a hydrophobic, non-polymeric cross-linked gel coating of a medical device, taking whatever precautions are necessary to make the resulting coating maintain desired characteristics.

Figure 5:
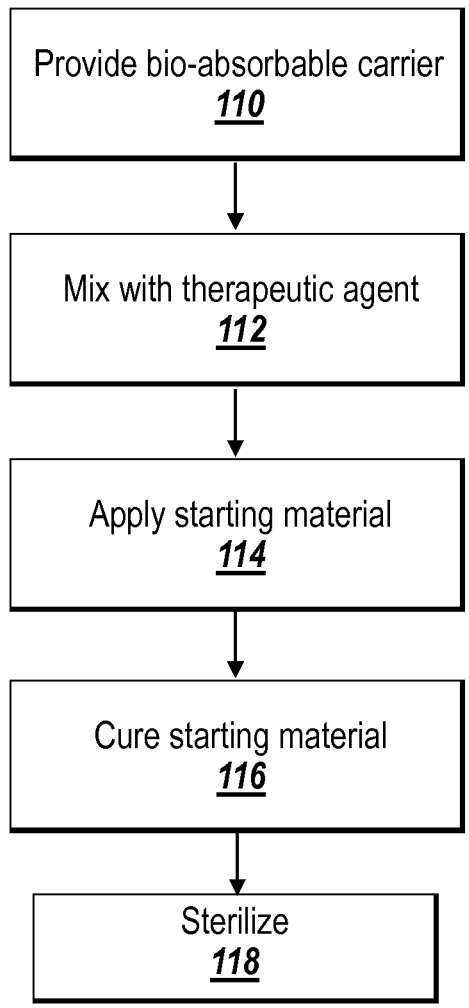
FIG. 5 is a flow chart illustrating a variation of the method of FIG. 4, in accordance with one embodiment of the present invention.

FIG. 5 is a flowchart illustrating one example implementation of the method of FIG. 4. In accordance with the steps illustrated in FIG. 5, a bio-absorbable carrier component (e.g., a naturally occurring oil) is provided along with a therapeutic agent component (step 110). The provision of the bio-absorbable carrier component and the provision of the therapeutic agent component can occur individually, or in combination, and can occur in any order or simultaneously. The bio-absorbable carrier component is mixed with the therapeutic agent component (or vice versa) to form a starting material which is to become a hydrophobic, non-polymeric cross-linked gel coating (step 112). The starting material is applied to the medical device, such as the stent 10, to form the coating (step 114). The coating is then cured (step 116) by any of the curing methods described herein to form a hydrophobic, non-polymeric cross-linked gel coating.

The coated medical device is then sterilized using any number of different sterilization processes (step 118). For example, sterilization can be implemented utilizing ethylene oxide, gamma radiation, E beam, steam, gas plasma, or vaporized hydrogen peroxide. One of ordinary skill in the art will appreciate that other sterilization processes can also be applied, and that those listed herein are merely examples of sterilization processes that result in a sterilization of the coated stent, preferably without having a detrimental effect on the coating 20.

It should be noted that the oil component or oil composition can be added multiple times to create multiple tiers in forming the coating. For example, if a thicker coating is desired, additional tiers of the oil component or oil composition can be added after steps 100, 104, 106, 108, 110, and/or 112. Different variations relating to when the oil is cured and when other substances are added to the oil are possible in a number of different process configurations. Accordingly, the present invention is not limited to the specific sequence illustrated. Rather, different combinations of the basic steps illustrated are anticipated by the present invention.

Figure 6A:
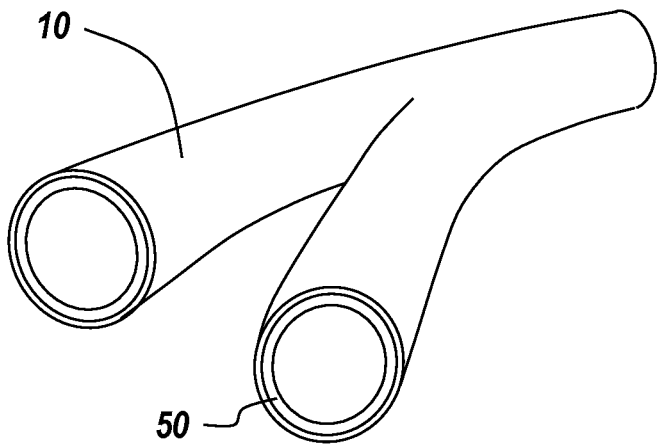
FIGS. 6A-6C are various images of coated medical devices.
Figure 6B:
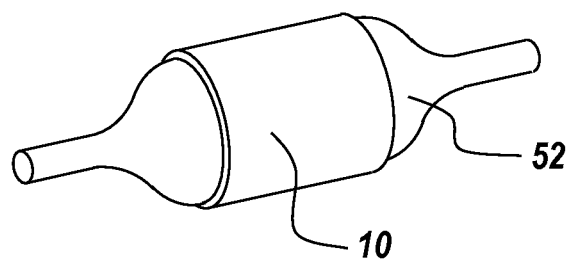
Figure 6C:
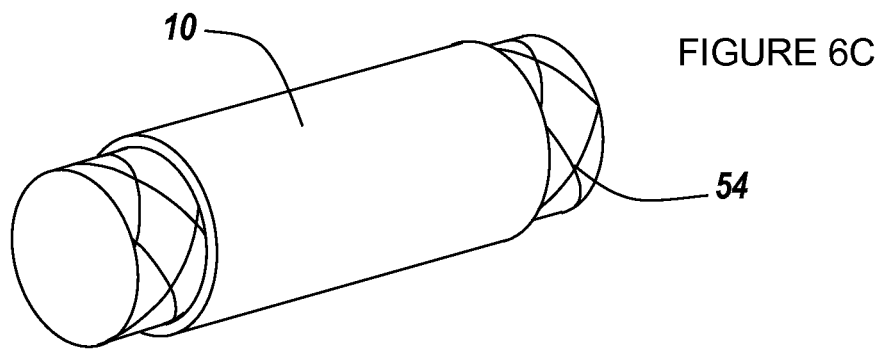

FIGS. 6A-6C illustrate some of the other forms of medical devices mentioned above in combination with the coating 10 of the present invention. FIG. 6A shows a graft 50 with the coating 10 coupled or adhered thereto. FIG. 6B shows a catheter balloon 52 with the coating 10 coupled or adhered thereto. FIG. 6C shows a stent 54 with the coating 10 coupled or adhered thereto. Each of the medical devices illustrated, in addition to others not specifically illustrated or discussed, can be combined with the coating 10 using the methods described herein, or variations thereof. Accordingly, the present invention is not limited to the example embodiments illustrated. Rather the embodiments illustrated are merely example implementations of the present invention.

Various aspects and embodiments of the present invention are further described by way of the following Examples. The Examples are offered by way of illustration and not by way of limitation.

EXAMPLES

Figure 7:
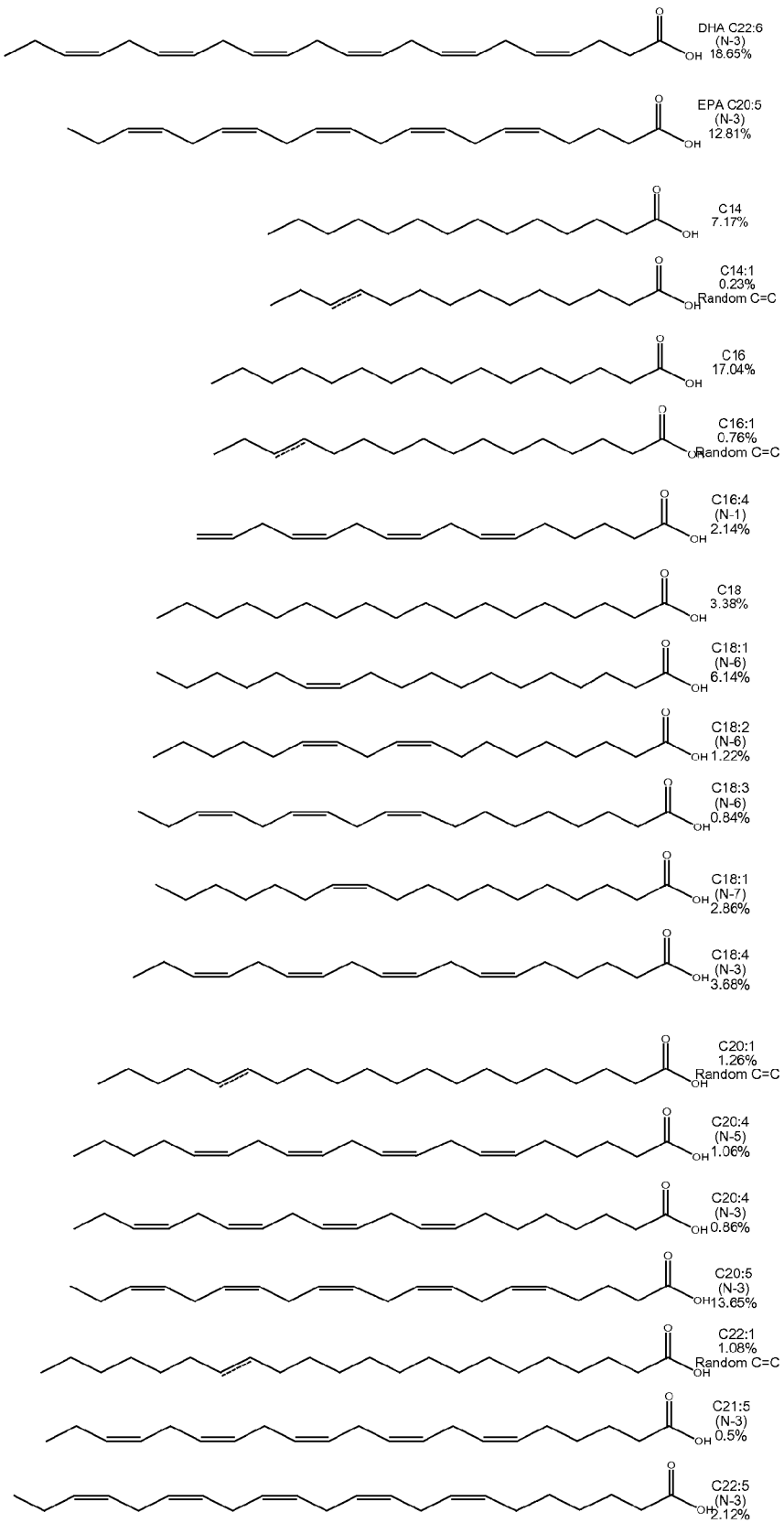
FIG. 7 schematically depicts various chemical structures of the fatty acid chains that were detected after saponification of the cured fish oil coating of Example 1.

The following examples all employ a fish oil starting material. This starting material contained a mixture of varying chain length saturated and unsaturated fatty acids, glycerides, and triglycerides with an iodine value above 150 (a measure of the amount of chain unsaturation. The higher the iodine number, the more unsaturated the hydrocarbon chains. Specifically, the fish oil contained at least 18% of the all cis forms of 5, 8, 11, 14, 17-eicosapentaenoic acid (EPA) and 12% of the all cis forms of 4, 7, 10, 13, 16, 19-docosahexaenoic acid (DHA) fatty acids. The chemical structures of the fatty acid chains that were detected after saponification of the fish oil by GC/MS analysis provided in the manufacturer's certificate of analysis (Pronova, EPAX 3000 TG) are presented in FIG. 7. The certificate of analysis also showed that the fish oil possessed 27.59% saturated fatty acids, 23.30% monounsaturated fatty acids, and 45.05% polyunsaturated fatty acids, of which 40.63% were specifically omega-3 fatty acids.

In the various examples, the drug release coatings and tested coated medical devices were prepared generally as follows except as described otherwise in the specific example. A coated medical device was prepared by encapsulating an either Atrium Prolite or Prolite Ultra polypropylene mesh in liquid fish oil (EPAX 3000 TG) using a manual dipping and/or roller application. The samples were subsequently placed on a Teflon lined metal pan and cured.

Example 1

Characterization of a Coating

In Example 1, the coated medical devices were cured in a high airflow oven at a range of times and temperatures (standard conditions were 150° F. for 3 days and 200° F. for 24 hours), after which the fish oil was converted into a cross-linked gel coating encapsulating the polypropylene mesh by a lipid autoxidation mechanism using heat as a catalyst.

FTIR, DSC, liquid and solid state $C^{13}$ NMR, X-ray diffraction, GC/MS, and LC/MS analysis were performed on the EPAX 3000 TG fish oil coatings cured at 200° F. for 24 hours.

Figure 8:
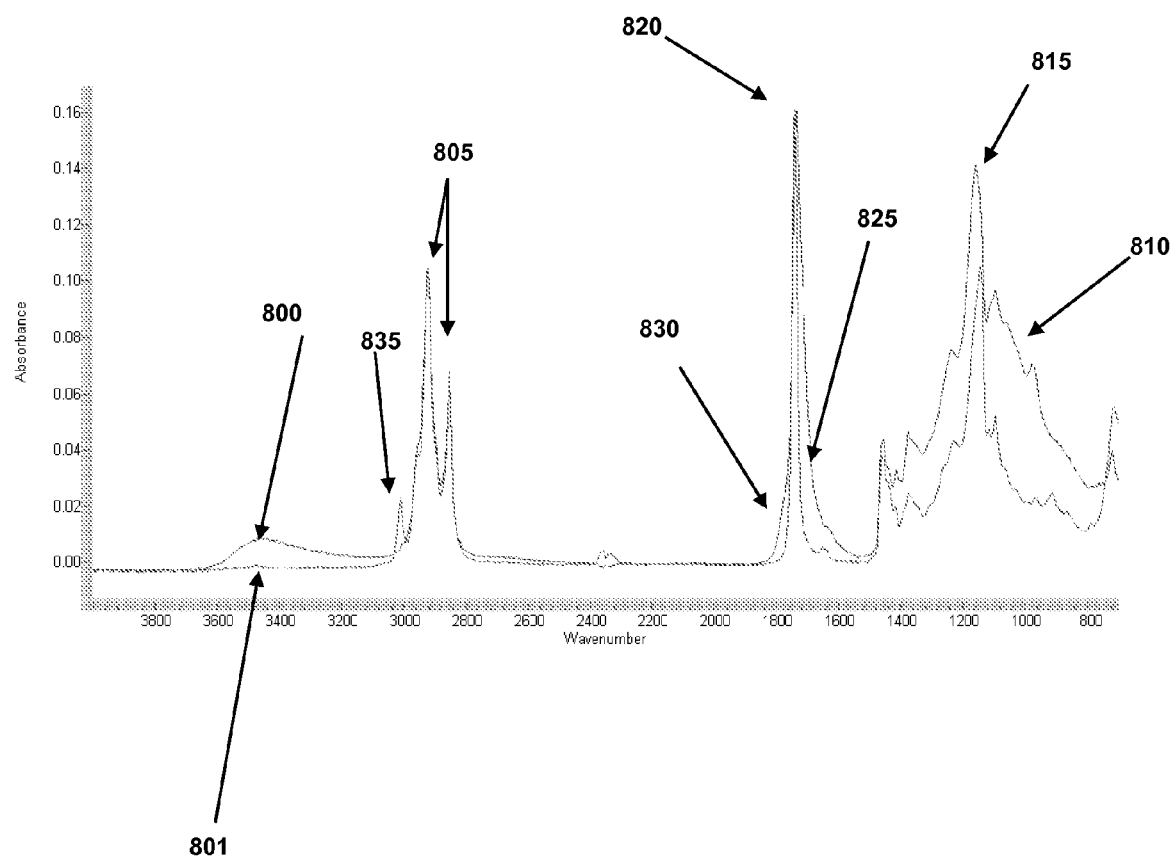
FIG. 8 depicts a FTIR analysis of the final cured coating after heating at 200° F. for 24 hr of Example 1.

FTIR Analysis: FIG. 8 is an FTIR analysis, which illustrates a comparison of the uncured fish oil (801) with the final cured coating. The FTIR shows that the coating contained hydroxyl (800), methylene (805), methyl (805), trans C=C (810), and anhydride/aliphatic peroxide/lactone bonds (815 and 830). A complex carbonyl band shape was obtained and determined to contain ester (820), ketone (825), aldehyde (825), and fatty acid (800) byproduct absorptions in addition to detecting the presence of cross-linking as observed in the anhydride/lactone/aliphatic diacylperoxide band absorption. The position of the methylene bands showed that the hydrocarbon chains present in the coating were in a disordered state, which is consistent with a non-crystalline structure.

Further, the cis C=C bonds in the fish oil starting material (835) were observed to be almost entirely consumed during the curing process. There was a corresponding increase in the trans C=C bonds (810) during the curing process.

Figure 9A:
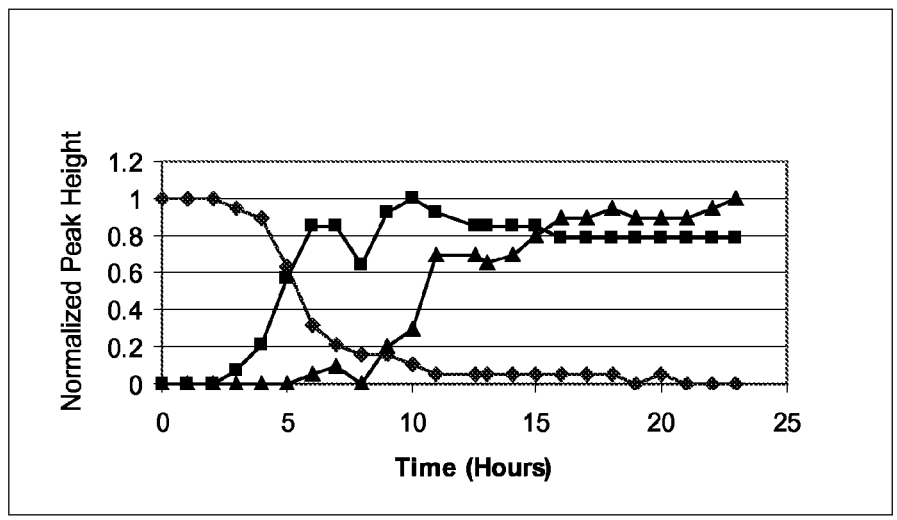
FIGS. 9A-9C depict analysis of FTIR data discussed in Example 1.
Figure 9B:
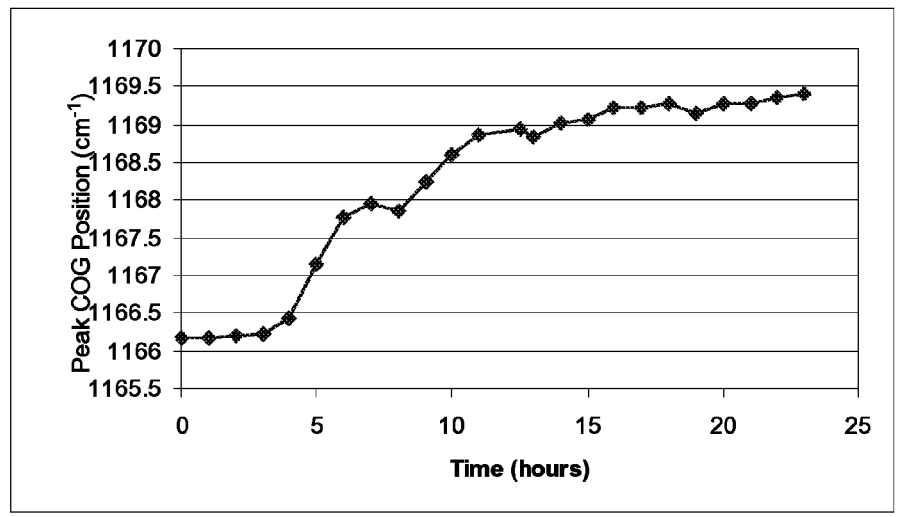
Figure 9C:
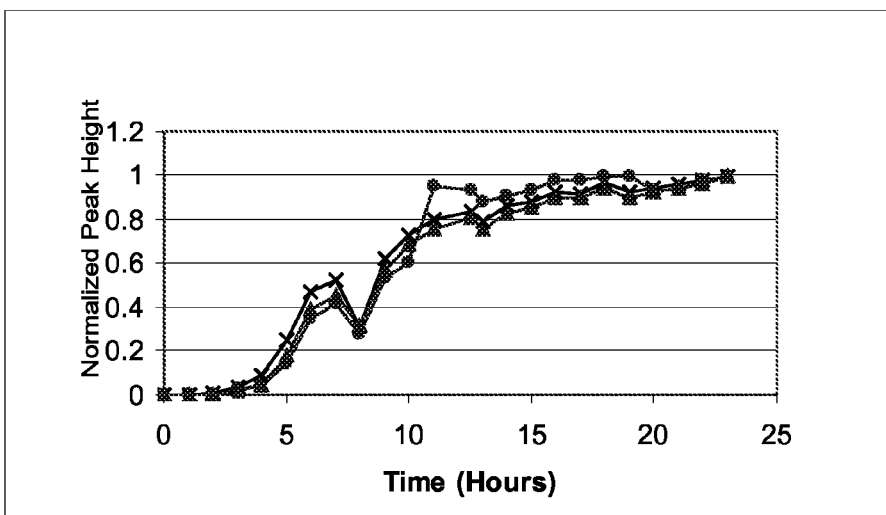

FTIR spectra were also acquired kinetically during the curing process using a procedure described in the literature (see, e.g., Van de Voort, F. R.; Ismail, A. A.; Sedman, J.; and Emo, G. (1994) *JAOCS,* vol 70, no. 3, pgs 243-253, the entire contents of which is hereby incorporated by reference) to monitor changes in the chemistry of the coating. FIG. 9A compares the decrease of the normalized peak height of the cis bands and the increase in the normalized peak heights of the trans C=C and anhydride/aliphatic peroxide/lactone C=O peak height during curing at 200° C. FIG. 9C compares the normalized peak height changes in the oxidized byproduct (e.g., ketones, fatty acids and unsaturated aldehydes) at 200° C. It was observed that initially during heating that the cis C=C bonds (♦ in FIG. 9A) (3011 $cm^{-1}$) were converted to isolated and conjugated trans C=C bonds (■ in FIG. 9A) (979 $cm^{-1}$) during the first 11 hours of curing. Concurrent with the conversion of the C=C double bonds into the trans configuration was the appearance of anhydride/aliphatic peroxide/lactone bonds and an almost maximal shifting of the C—O—C/C—O—O—C band (▲ in FIG. 9A), indicating the formation of cross-linking bonds, after which the coating solidified into a sticky gel-like coating. After the initial gel solidification process, continued curing of the coating resulted in partial consumption of the trans C=C bonds in addition to the continued creation of anhydride, lactone, aliphatic peroxide, ether, and peroxide cross-links, see. e.g., FIG. 1, (see, also, data of FIGS. 9A and 9C). The production of shorter chain length fatty acid (▲), unsaturated aldehyde (•) and ketone (X) byproducts were also monitored, shown in FIG. 9C. The coating produced at the end of the curing was a flexible gel-like coating that maintained a large number of ester bonds from the oil triglyceride starting material.

Comparison of Coatings Cured at 150° F. and 200° F.

An additional comparison of the FTIR spectra of the fish oil cured at 150° F. for 3 days with the 200° F. for 24 hours was performed. The comparison showed that curing at 150° F. for 3 days resulted in a 36% difference in the anhydride/aliphatic peroxide/lactone cross-linking, a 25% difference in the trans C=C bonds and a 10% difference in the amount of fatty acid/ketone byproducts formed compared to the samples that were cured at 200° F. for 24 hours. These results indicated that the coatings cured at 200° F. were more cross-linked than the coatings cured at 150° F.

Further FTIR studies were performed in order to analyze the differences between the coatings cured at 150° F. and 200° F. An amount of 125 µL of Ocean Nutrition fish oil was applied to 1×1" polypropylene mesh and cured either at 200° F. for 24 hours or 150° F. for 3 days. The differences between the coatings were determined using FTIR and the saponification rate. The FTIR spectra of these different cured mesh coatings are presented in FIGS. 10A-10C. From a general inspection of the overall FTIR spectra of the 150 (1005) and 200° F. (1010) coatings cured on polypropylene mesh in FIG. 10A, there appears to be little significant differences between the two coatings. However, upon zooming in from 3600-2700 $cm^{-1}$ as illustrated in FIG. 10B, it can be seen that there are small differences in the OH band (1015), likely due to a greater amount of glycerides and fatty alcohols formed in the coating cured at 150° F. (1005), when compared to the coating cured at 200° F. (1010). Additionally, inspection of the carbonyl band, as illustrated in FIG. 10C, showed approximately a 13% increase in absorption for the sample cured at 200° F. (1010) at approximately 1775 $cm^{-1}$, which is assigned to the formation of a combination of aliphatic peroxide, lactone, and anhydride cross-links (1020), when compared to the coating cured at 150° F. (1005). Based on FTIR analysis, the coatings cured at 150 and 200° F. are generally similar except for a few differences in byproduct formation and cross-linking.

DSC: An extraction was performed in THF at 37° C. for 3 hours to isolate the soluble and insoluble components of the fish oil coating cured at either 150° F. for 3 days or 200° F. for 24 hours, followed by evaporation of the solvent in a hood and final drying in the bell jar vacuum. Weight measurements showed that this extraction of the coating cured at 150° F. for 3 days resulted in a 62:38 ratio of soluble and insoluble materials. The weight measurements showed that this extraction of the coating cured at 200 for 24 hours resulted in a 50:50 ratio of insoluble and soluble materials. DSC analysis of the insoluble material of the coating cured at 150° F. for 3 days showed that the insoluble material was 73% cured. A comparison analysis of DCS profiles of the soluble materials of the cured coatings indicates that the coating cured at 200° F. possessed less long chain oxidized by products that the coating cured at 150° F.

Figure 11A:
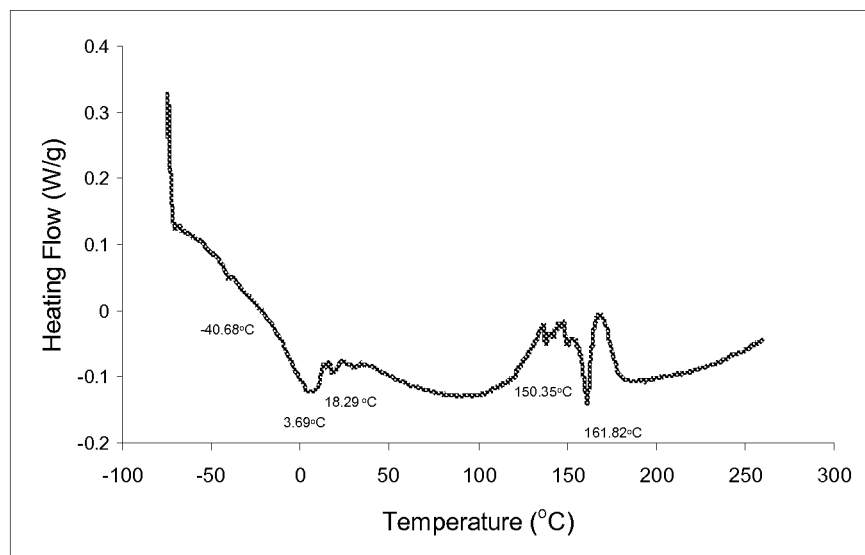
FIG. 11A depicts a DSC curve of the soluble materials in the cured fish oil coating of Example 1.
Figure 11B:
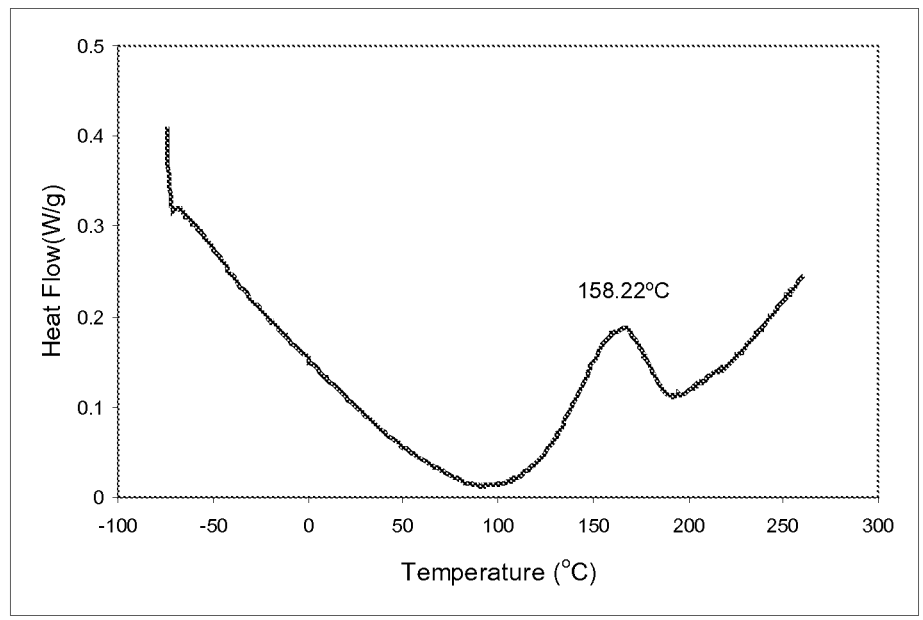
FIG. 11B depicts a DSC curve of the insoluble materials in the cured fish oil coating of Example 1.

A DSC profile of the soluble materials extracted from the coating cured at 200° F. for 24 hours is shown in FIG. 11A. The DSC profile indicates that that the soluble materials are a polymorphous crystalline material with different molecular weight and chemical structures. FIG. 11B is a DSC profile of the insoluble materials obtained from the coating cured at 200° F. for 24 hours and indicates that the insoluble component is an amorphous material and that the apparent % cure of the insoluble material is about 92%.

X-Ray Diffraction: X-ray diffraction results were inconclusive and suggest the presence of a disordered, amorphous material as this technique is only sensitive to crystalline compounds. The result is consistent with the FTIR and DSC analytical results.

$C^{13}$ NMR Analysis: NMR confirmed the presence of C=C bonds, methyl, methylene, and C—O bonds of the C-QUR™ coating that resembled the starting material, though with less absorption in the C=C area.

Figure 12:
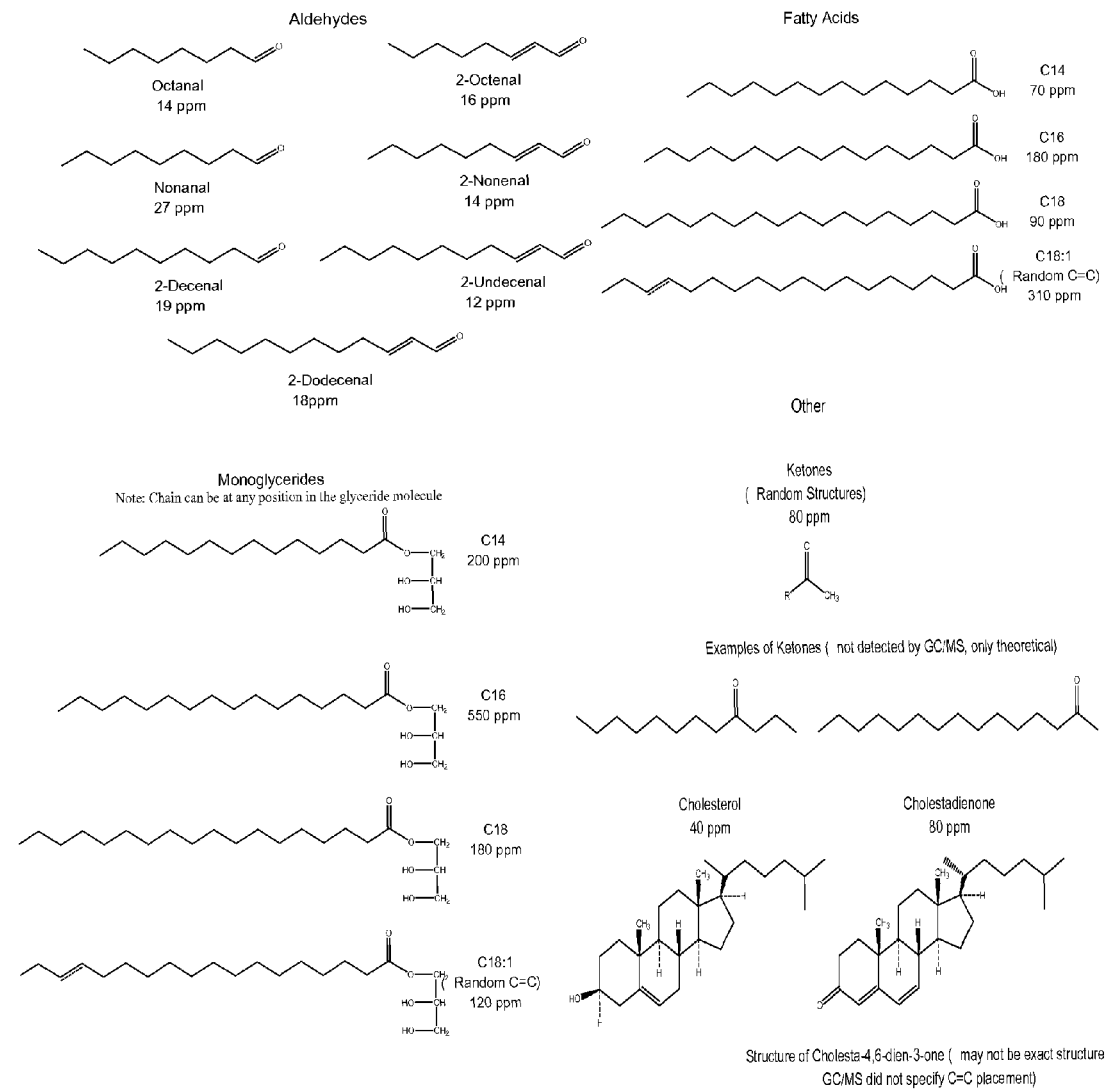
FIG. 12 schematically depicts the molecular structures of the components detected in the soluble fraction of the coating of Example 1.

GC/MS and LC/MS: In preparation for GC/MS and LC/MS analysis, the coating was dissolved in THF at about 65° C. and the soluble component was filtered away from the insoluble component. Using this process it was determined that 68% of the coating was insoluble in THF and suggested to be composed of a cross-linked fatty acid and glyceride fish oil cross-linked gel coating. The other 32% soluble portion of the coating consisted of lower molecular weight compounds with a mass below 3000. The soluble portion of the coating was determined to contain fatty acids and glycerides making up the majority of the soluble fraction with a small amount of ketones and aldehydes. A schematic of the molecular structures of the components detected in the soluble fraction of the coating is presented in FIG. 12. It should be noted that any alcohol byproducts contained in the soluble component of the cured fish oil coating would not be detected using these analytical methods.

Hydrolysis Testing

The experiments indicate that cured coatings of this example comprise mostly ester bonds in addition to lesser amounts of anhydride, lactone, and aliphatic peroxide bonds that will undergo hydrolysis in vivo to convert into smaller components over time. The following observations support the conversion of the cured coating using a hydrolysis mechanism, as shown in FIG. 3. These experiments, to assess the conversion of the cured coating, were conducted as follows.

A saponification reaction was performed in 0.1 M NaOH, pH>11 that is known to readily convert triglyceride esters into lower molecular weight fatty acids and alcohols (i.e., glycerol). The cured fish oil coating was confirmed to degrade by a hydrolysis mechanism after being placed in the NaOH solution and completely dissolved within 30 min, leaving bare polypropylene mesh behind.

To assess the differences in the degradation behavior of the coatings cured at 150° F. and 200° F., samples of the cured fish oil encapsulated mesh samples were placed in a 0.1 M sodium phosphate buffer containing 0.1 M NaCl solution at pH=7.4 at both 37° C. and 55° C. The coating cured at 200° F. dissolved during an 18-day period at 55° C. whereas it took 12 weeks to dissolve at 37° C. The coating cured at 150° F. dissolved during an 18-21 day period at 55° C.

To further assess the differences in the conversion behavior of the coatings cured at 150° F. and 200° F., a 1×1" coating was placed into a 20 ml glass scintillation vial with 20 ml of 0.1 M NaOH, pH>11. The amount of time for the coating to be hydrolyzed and be dissolved into solution was determined to be approximately 14 minutes for the coating cured at 150° F. and 19 minutes for the coatings cured at 200° F., which coincides with the FTIR spectral data where the coating cured at 200° F. was more cross-linked and thus took longer to saponify in basic conditions.

Figure 13:
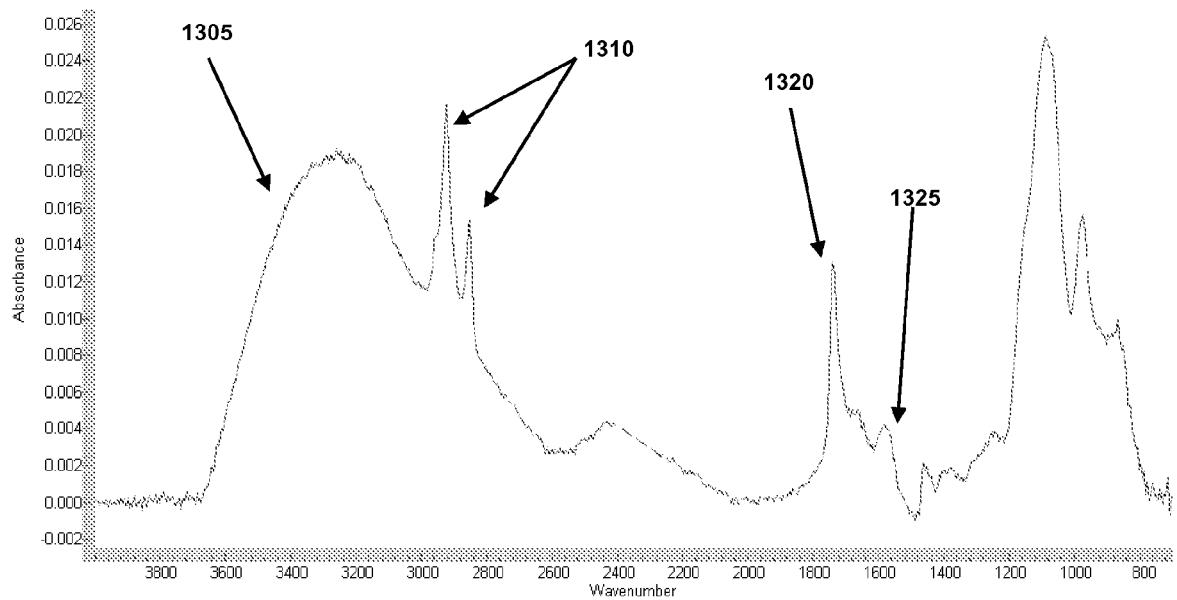
FIG. 13 depicts a representative FTIR spectrum of the cured coating hydrolyzed in buffer solution consistent with the production of fatty acid, fatty acid salts, and alcohols at day 16 as discussed in Example 1.

FTIR spectra acquired of the converted cured coating in buffer solution were consistent with the production of fatty acid, fatty acid salts, and alcohols. A representative spectrum acquired of the hydrolyzed material at day 16 is shown in FIG. 13. This spectra illustrates significant differences in the OH (water and alcohols) band (1305), the $CH_2$ band (fatty acids and alcohols, 1310), the ester C=O band (1320) and the fatty acid C=O—O band (1325), when compared to the spectrum in FIG. 8.

Several tests were performed to determine the composition of the converted material in 0.1 M phosphate buffer with 0.1 M sodium chloride at 37 and 55° C. (1×1" in 20 ml of buffer). The results of these tests were as follows.

HPLC Glyceride Test

No di- or triglyceride peaks were detected in the sample even after concentrating it by a factor of 5. However, peaks due to the presence of free fatty acids were assigned and a larger than normal solvent front peak was believed to be due to the presence of long chained alcohols/glycerol. Results were similar the samples degraded in the buffer at both 37 and 55° C.

GC Fatty Acid Profile

The sample for this test also had to be concentrated in order to obtain adequate detection by the GC. The fatty acids detected were C14, C16, C16-1, C18, and C18-1. The coating degraded at 55° C. had a greater amount of fatty acids detected than the coating degraded at 37° C., but in similar proportions.

HPLC Molecular Weight Test

The sample for this test also had to be concentrated by a factor of 5 in order to obtain adequate detection. The weights detected for the sample degraded at 55° C. (with normalized peak area %) indicated that 90% of the fraction of the sample soluble in THF had a molecular weight of less than or about equal to 1000. Likewise for the sample degraded at 37° C., the weights and normalized peak areas indicated that 90% of the fraction of the sample soluble in THF had a molecular weight of less than or about equal to 1000. The peak at 1000 would be due to structures resembling triglycerides (although apparently too dilute to pick up on the glyceride screen) and the components below 500 would be due to fatty acid or other lower molecular weight byproducts.

HPLC Glycerol Test

Several peaks attributed to fatty acids and alcohols were observed. Model cured fish oil films showed that the coating swelled at higher pH and temperature, which resulted in the coating to degrade more quickly.

Example 1

Summary

Figure 14:
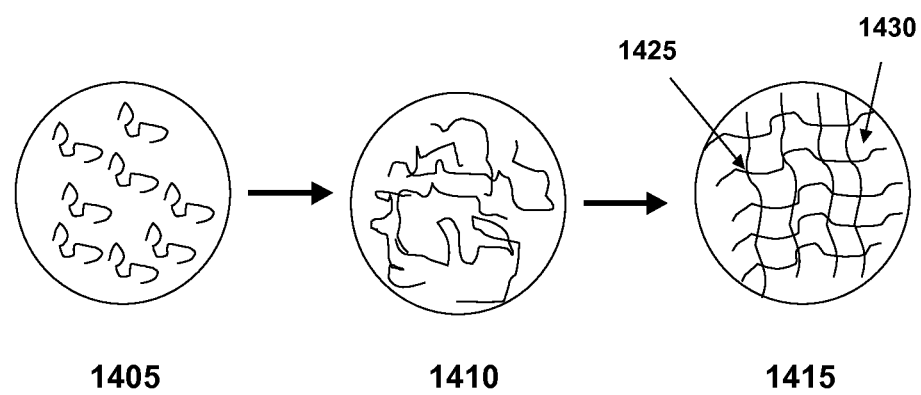
FIG. 14 schematically depicts the production of a hydrophobic, non-polymeric cross-linked gel of Example 1.

Based on the information provided from laboratory experiments, analytical data, and literature research a theoretical structure of the cured fish oil coating was derived, as schematically presented in FIG. 14. Without being bound by a particular theory, the composition of the uncured coating (1305) is thought to be a mixture of saturated and polysaturated (i.e., cis) fatty acid triglycerides. The partially cured coating (1410) is thought to be composed of a flexible gel containing short chain byproducts (i.e., fatty acids, ketones, aldehydes), less polyunsaturated fatty acids, (mostly trans C═C bonds), and cross-linking of fatty acid chains (mostly peroxide, ether and C—C). The cured coating (1420) is believed to comprise short chain byproducts (i.e., fatty acids, ketones, aldehydes, and partially reacted fish oil, 1430), mostly saturated fatty acids, with some monounsaturated fatty acids (all trans C═C), and a network of cross-linked fatty acids and glycerides (1425) comprising mostly ester bonds with smaller amounts of peroxide, ether and C—C bonds. The cured coating comprises, then, a cross-linked structure of triglyceride and fatty acid molecules in addition to free and bound glycerol, mono-, di-, and triglyceride, fatty acid, anhydride, lactone, aliphatic peroxide, aldehyde, and ketone molecules. There is a large amount of ester bonds remaining after curing from the triglyceride oil headgroup in addition to cross-linking bands comprised of a mixture of peroxide, ether and carbon-carbon linkages, but under the current conditions of Example 1, the peroxide linkages appear to be dominant due to the hydrolysable nature of the cured coating. Based on bench testing, the cured coating degrades into fatty acid, short and long chain alcohol, and glyceride molecules, which is consistent with hydrolytic degradation of triglycerides (see, e.g., FIG. 3).

Example 2

Tailoring Drug Release Profile of Coating: Curing Conditions

An advantage of the cured fish oil coating in various embodiments of the present inventions is that the curing conditions utilized (i.e., cure time and temperature) can directly influence the amount of coating cross-linking density and byproduct formation, which in turn effects the rate of coating conversion to free fatty acids, fatty alcohols, and glycerol. The effects of various curing conditions on fish oil curing chemistry and drug release properties are demonstrated in this Example.

The Effects of Time and Temperature on the Release of Therapeutics

Drug delivery experiments were performed using coatings cured at 200° F. for 24 hours or at 150° F. for 3 days. All samples were 1×1" and dissolution was performed in 0.01 M PBS solution. All drug samples were loaded as an uncured mesh coating created by mixing the liquid fish oil and drug together, with or without solvent, followed by coating a piece of bare mesh and curing using either the 150 or 200° F. curing conditions.

Anti-Inflammatory Drug Delivery

Figure 15:
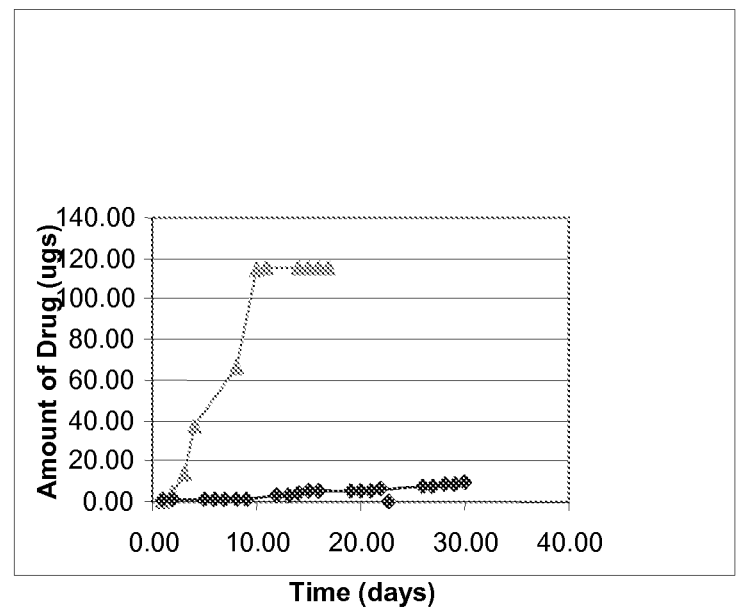
FIGS. 15 and 16 depict drug release data in an aqueous media discussed in Example 2.

FIG. 15 depicts the drug release profile measured for an anti-inflammatory drug. The figure compares two curing conditions, heating for 24 hours at 200° F. (♦) or 3 days at 150° F. (▲). The starting material comprised 2.4% model anti-inflammatory drug (after nMP solvent was removed) in fish oil (EPAX 3000 TG). The initial drug loading after curing, based on HPLC measurements, was about 442 µg (14.84% recovery) for the 200° F. conditions, and about 238 µg (10.97% recovery) for the 150° F. conditions. It is to be noted that the percentage amount recovered is dependent on the coating weight and amount of drug detected using HPLC methods after drug extraction from the cured fish oil coating.

These results show that the coating cured at 150° F., which has less cross-linking and greater amount of soluble components, results in a faster drug release than the coating cured at 200° F., which possess more cross-linking and fewer soluble components. This example demonstrates the ability to load an anti-inflammatory into cured fish oil coatings, and by using temperature to control the cross-linking properties of that coating, the drug release and delivery profile is significantly altered.

Anti-Proliferative Drug Delivery

Figure 16:
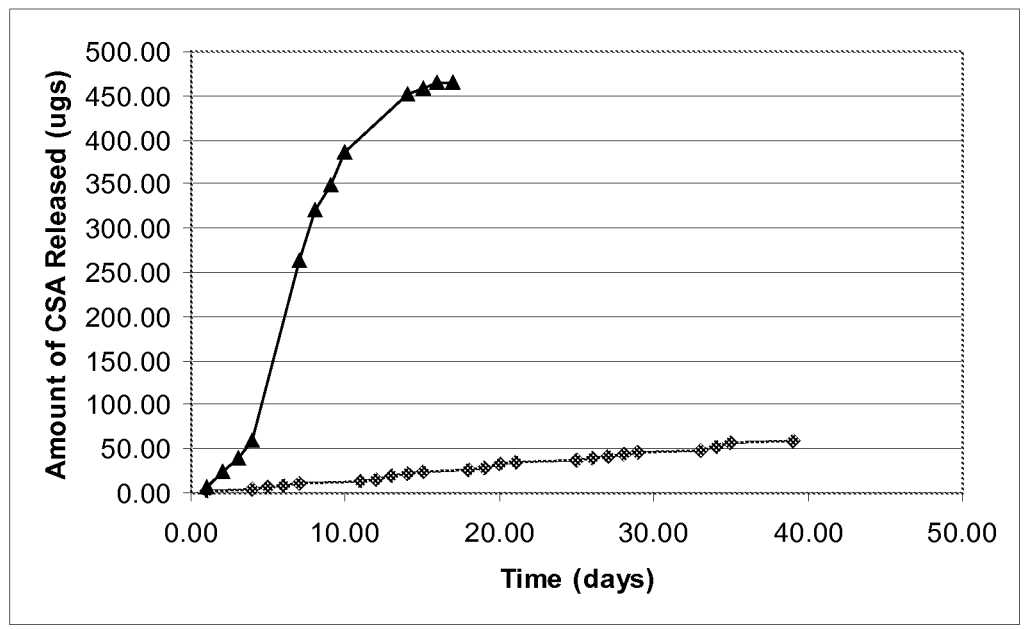

FIG. 16 depicts the drug release profile measured for an anti-proliferate drug. The figure compares two curing conditions, heating for 24 hours at 200° F. (♦) or heating for 3 days at 150° F. (▲). The starting material comprised 2.84% Cyclosporine A (CalBiochem) in fish oil (EPAX 3000 TG). No solvent was used as Cyclosporine A was soluble in the fish oil with slight heating at 37° C. The initial drug loading after curing, based on HPLC measurements, was about 478 µg (14.22% recovery) for the 200° F. conditions, and about 1158 µg (26.00% recovery) for the 150° F. conditions. It is to be noted that the percentage amount recovered is dependent on the coating weight and amount of drug detected using HPLC methods after drug extraction from the cured fish oil coating.

These results confirm that the coating cured at 150° F., which has less cross-linking and greater amount of soluble components, results in a faster drug release than the coating cured at 200° F. cured coating, which possess more cross-linking and fewer soluble components. This example demonstrates the ability to load an anti-proliferative, Cyclosporine A, into cured fish oil coatings and by using temperature to control the cross-linking properties of the coating, the drug release and delivery profile is significantly altered.

Example 3

Tailoring Drug Release Profile of Coating: Other Agents

In various embodiments, the drug release and delivery profile of a non-polymeric cross-linked gel coating of the present invention can be tailored by the inclusion of vitamin E in the starting material. Vitamin E is an antioxidant known to slow down autoxidation in fish oil by reducing hydroperoxide formation, which results in a decrease in the amount of cross-linking observed in a cured fish oil coating. In addition, not all therapeutic compounds of interest present adequate solubility in 100% fish oil and the vitamin E can be used to increase the solubility of certain drugs in fish oil. Additionally, depending on the chemical structure and properties of the drug to be loaded into the coating, vitamin E may act to protect the drug during the curing process. These statements are supported in the following examples.

The Effects of Vitamin E Composition on Cured Fish Oil Coating Chemistry.

Figure 17:
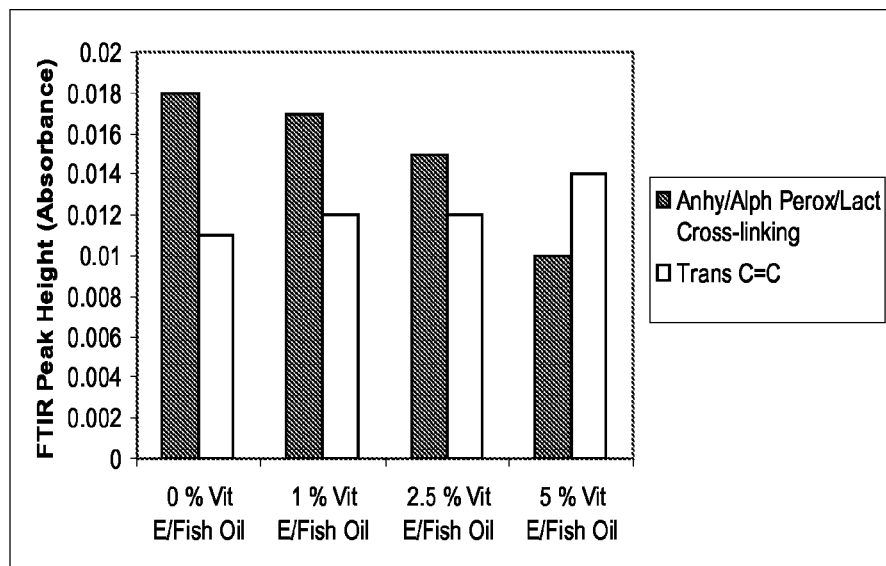
FIG. 17 depicts FTIR data discussed in Example 3.

In this set of experiments, the curing conditions remained constant at 150° F. for 3 days while the amount of vitamin E composition was varied from 0-5%. FTIR results showed that the amount of anhydride/aliphatic peroxide/lactone cross-linking decreased with increasing vitamin E composition. In addition, the trans C=C bonds increased with increasing amounts of vitamin E. Comparison of the FTIR results are shown in FIG. 17. The FTIR results show that by increasing the amount of vitamin E in the coating that the fish oil component of the coating is less cross-linked and cured than its 100% fish oil counter part.

The Ability of Vitamin E Composition to Protect a Therapeutic During Curing

Rapamycin loaded drug release mesh coatings (1×1") were produced using 150° F. curing for 3 days with varying amount of vitamin E present in the cured fish oil coating. The amount of rapamycin loaded into all the coating formulations before curing remained constant at 4.88%. The presence of the vitamin E acted to protect the rapamycin, as shown in the extracted rapamycin (Rap) drug amounts recovered using HPLC analysis after curing with varying amounts of vitamin E, as shown in Table 2.

TABLE 2

| Coating | CURED COATING | |
| --- | --- | --- |
|  | Rap Drug Loading (HPLC) | % Rap Recovered (based on HPLC) |
| 100% Fish Oil | 378 | 6.5 |
| 1% Vitamin E/Fish Oil | 2126 | 34 |
| 2.5% Vitamin E/Fish Oil | 2649 | 45 |
| 5% Vitamin E/Fish Oil | 3013 | 52 |

These results show that increasing the amount of vitamin E increases the amount of rapamycin detected from the cured fish oil coating and indicates that vitamin E serves to protect the drug from oxidation during curing. This also suggests that rapamycin (which has 3 conjugated trans C=C bands) might react with the polyunsaturated fatty acid chains in the fish oil and likely cross-links with them during curing. Vitamin E, which is a free-radical scavenger and can inhibit the cross-linking/oxidation of the fish oil, slows the kinetics of the curing reaction and is believed to protect the rapamycin during the curing process. The HPLC detection of rapamycin is directly dependent on the preservation of the C=C bonds in the drug during curing; thus, the increased detection of the rapamycin observed with increasing amounts of vitamin E supports the theory that the vitamin E protects the drug by preventing the oxidation of the drug C=C bonds.

The Ability of Vitamin E to Alter Release Profile

All coated mesh samples were 1×1" and dissolution was performed in 0.01 M PBS solution. All drug samples were loaded as an cured mesh coating created by mixing the liquid fish oil and drug together, with or without solvent, followed by coating a piece of bare mesh and curing at 150° F. for 3 days.

Figure 18:
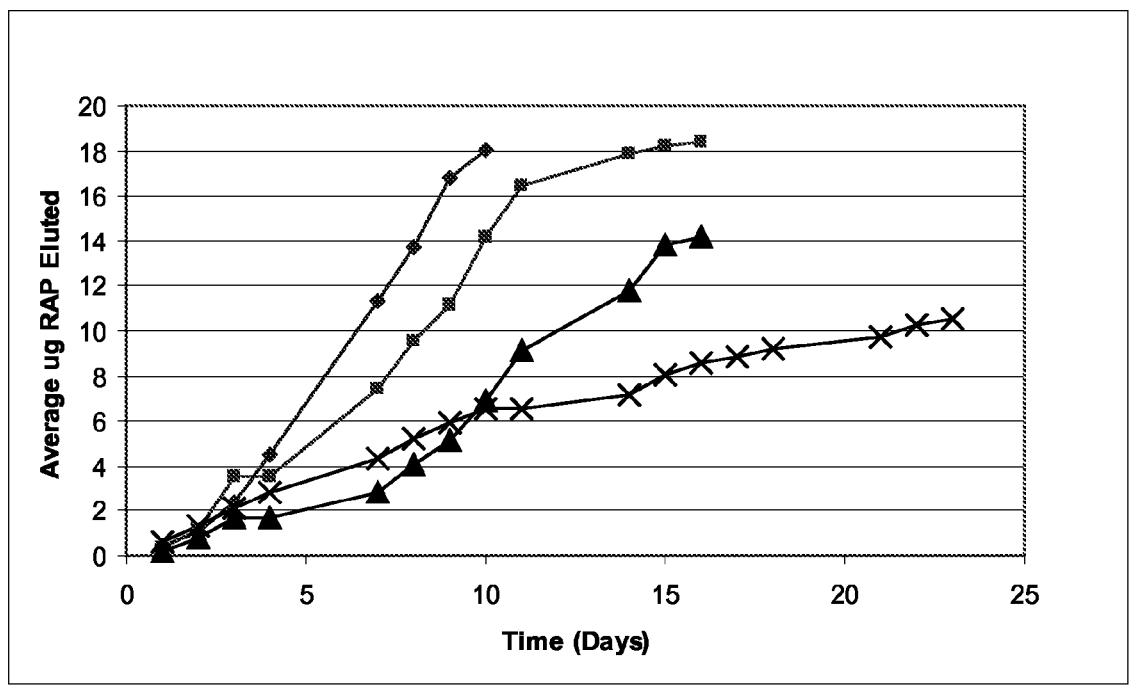
FIG. 18 depicts drug release data in an aqueous media discussed in Example 3.

FIG. 18 depicts the drug release profile measured for rapamycin. The figure compares varying amounts of vitamin E added to the starting material prior to curing for 3 days at 150° F. The starting materials comprised 4.88% rapamycin (after solvent removal) in varying amounts of vitamin E in fish oil coatings, with 100% fish oil and 378 μg loading of rapamycin (♦), 1% vitamin E in fish oil and 2126 μg loading of rapamycin (■), 2.5% vitamin E in fish oil and 2649 μg loading of rapamycin (X). The initial drug loading is shown in Table 2.

It is to be noted that the percentage amount recovered listed in Table 2 is dependent on the coating weight and amount of drug detected using HPLC methods after drug extraction from the cured fish oil coating.

These results show that altering the vitamin E composition modifies the release profile of a therapeutic agent from the cured fish oil coating. Increasing the amount of vitamin E results in lengthening and slowing the release of the rapamycin into the dissolution buffer. Although the amount of rapamycin loaded in the initial coating formulation remained constant, increasing the amount of vitamin E in the coating results in, it is believed, protection of the drug and increasing the amount of free rapamycin extracted from the coating. Thus, despite the decrease in coating cross-linking and relative higher concentration of soluble components with increasing vitamin E content indicated by the FTIR results, drug release and delivery is slow due to the increased solubility and affinity of the rapamycin for the vitamin E compared to the aqueous release medium. Without being bound to any particular theory, it is thought that rapamycin (which has 3 conjugated trans C=C bands) reacts with the polyunsaturated fatty acid chains in the fish oil and likely cross-links with them during curing. The C=C bonds consumed during the curing process would result in a loss of C=C band intensity that is needed for the UV detection of rapamycin using the HPLC. Vitamin E, which is a free-radical scavenger and can inhibit the cross-linking of the fish oil, is believed to slow the kinetics of the curing reaction and as a result act to protect the rapamycin during the curing process.

Example 4

Tailoring Drug Release Profile of Coating: Multiple Coatings and Drug Location

In various embodiments, the present inventions provide drug release and delivery coatings where the drug release profile of the coating is tailored through the provision of two or more coatings and selection of the location of the therapeutic agent. The chemistry of the various coating layers can be adjusted by employing different curing conditions and/or vitamin E composition. The following examples demonstrate the ability to alter the chemistry and position of the drug-containing layer in cured fish oil mesh coatings.

The Effects of Time, Temperature, and Position

All coated mesh samples were 1×1" and dissolution was performed in 0.01 M PBS solution. Drug release coated mesh samples were created by mixing the fish oil and drug followed by coating a piece of bare mesh and curing using either 150 or 200° F. curing conditions. Overlayer mesh coatings were created by applying a drug-fish oil coating onto a previously coated and cured 100% fish oil coated mesh using 200° F. curing conditions, followed by curing the two coatings together at either 150° F. for 3 days or 200° F. for 24 hours.

Figure 19:
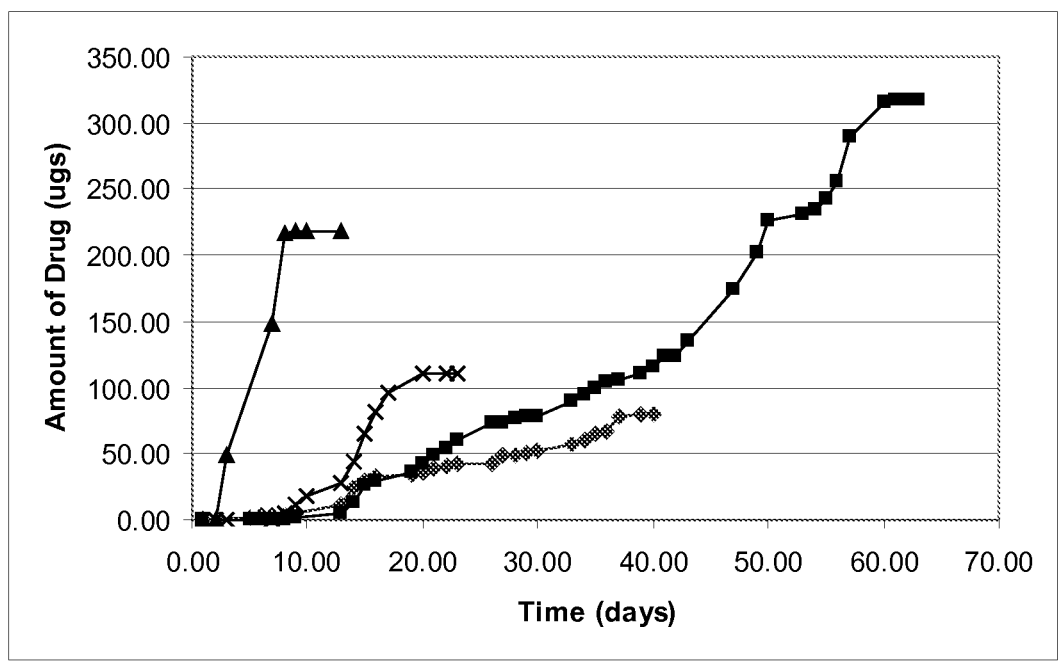
FIGS. 19-23 depict drug release data in an aqueous media discussed in Example 4.

FIG. 19 depicts the drug release profile measured for an anti-inflammatory drug. The figure compares two curing conditions, heating for 24 hours at 200° F. or heating for 3 days at 150° F. and for different positions of the drug (in the first layer versus in the overlayer). The starting material comprised 3.29% model anti-inflammatory drug (after nMP solvent was removed) in fish oil (EPAX 3000 TG).

These results show that adjusting curing temperature and drug layer coating position can alter the release of an anti-inflammatory. Both the first coating layer (▲) and overlayer (X) samples cured at 150° F., due to the lower amount of cross-linking, release more rapidly than the more crosslinked 200° F. samples. For the coatings cured at 150° F., the position of the drug in the encapsulated coating results in a faster release than for the overlayer coating. However, for the first coating layer (♦) and the overlayer coating (■) samples at 200° F., the opposite resulted. This illustrates the flexibility of the coating system where the release rate of the therapeutic from the overlayer and chemistry of the coating can be tailored based on the cure time, cure methods, thickness of coating, and/or temperature conditions employed.

Figure 20:
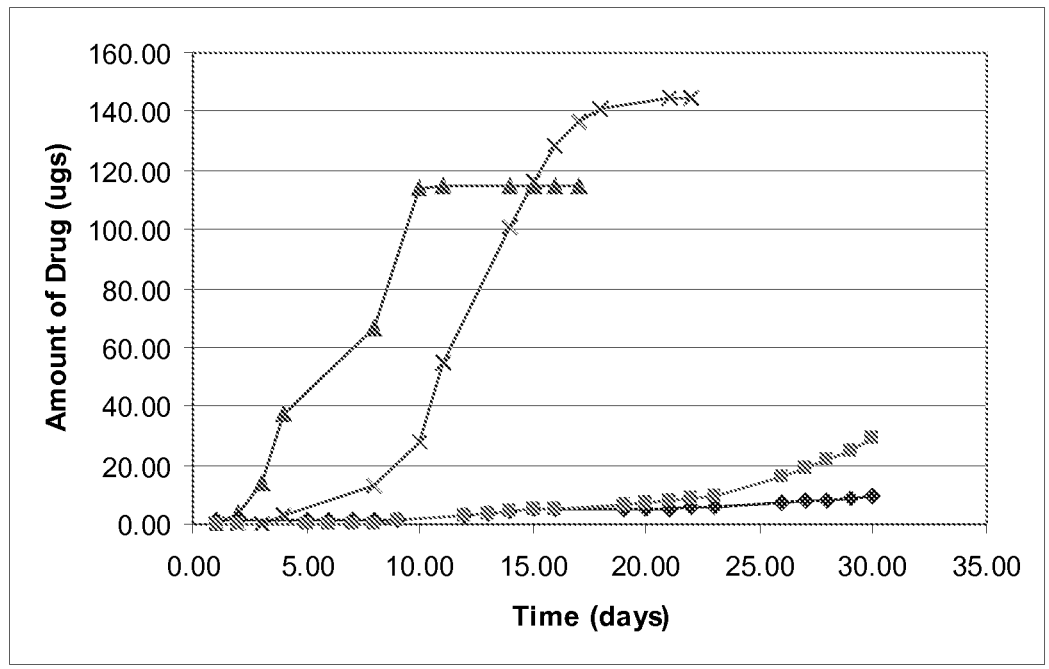

FIG. 20 depicts a further drug release profile measured for an anti-inflammatory drug. The figure compares two curing conditions, heating for 24 hours at 200° F. or heating for 3 days at 150° F. and for different positions of the drug (in the first layer versus in the overlayer). The starting material comprised 2.4% model anti-inflammatory drug (after nMP solvent was removed) in fish oil (EPAX 3000 TG). The initial drug loading after curing, based on HPLC measurements, was about 793 µg (28.7% recovery, ■) in the overlayer, and about 442 µg (14.84% recovery, ♦) in the first coating (underlayer) for the 200° F. conditions. The initial drug loading after curing, based on HPLC measurements, was about 477 µg (42.16% recovery, X) in the overlayer, and about 238 µg (10.97% recovery, ▲) in the first coating (underlayer) for the 150° F. conditions. It is to be noted that the percentage amount recovered is dependent on the coating weight and amount of drug detected using HPLC methods after drug extraction from the cured fish oil coating.

These results show that adjusting curing temperature and drug layer coating position altered the release of an anti-inflammatory, even at a lower initial drug loading. Both the first layer and overlayer samples cured at 150° F., due to the lower amount of cross-linking, release more rapidly than the more cross-linked 200° F. samples. For the coatings cured at 150° F., the position of the drug in the first layer coating results in a faster dissolution than for the overlayer coating.

Figure 21:
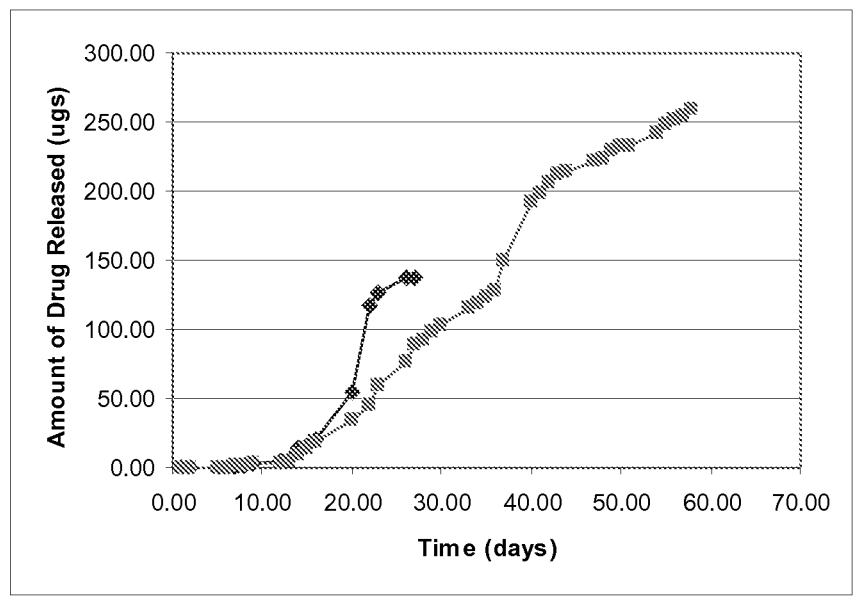

FIG. 21 depicts a further drug release profile measured for an anti-inflammatory drug. The figure shows data for curing by heating for 24 hours at 200° F. and for different positions of the drug (in the first layer versus in the overlayer). The starting material comprised 3.2% model anti-inflammatory drug (no nMP solvent used, the anti-inflammatory was suspended in the fish oil by vortexing) in fish oil (EPAX 3000 TG). The initial drug-oil dispersion looked cloudy and was vortexed prior to coating samples in a metal weigh pan or the drug would settle out. The initial drug loading after curing, based on HPLC measurements, was about 1348 µg (35.86% recovery, ■) in the overlayer, and about 348 µg (9.19% recovery, ♦) in the first coating (underlayer). The coating had dissolved by day 27. It is to be noted that the percentage amount recovered is dependent on the coating weight and amount of drug detected using HPLC methods after drug extraction from the cured fish oil coating.

These results show that adjusting drug layer coating position alters the release of an anti-inflammatory, even without using a solvent to solublize the drug in the coating.

Figure 22:
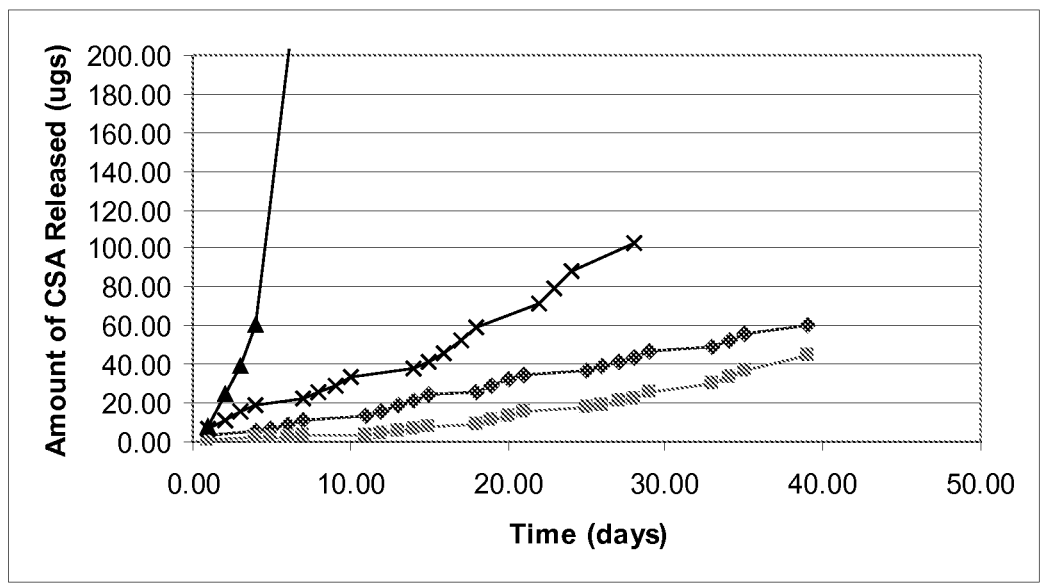

FIG. 22 depicts a further drug release profile measured for an anti-proliferative. The figure compares two curing conditions, heating for 24 hours at 200° F. or heating for 3 days at 150° F. and for different positions of the drug (in the first layer versus in the overlayer). The starting material comprised 2.84% Cyclosporine A (CalBiochem) in fish oil (EPAX 3000 TG). No solvent was used as Cyclosporine A was soluble in the fish oil with slight heating at 37° C. The initial drug loading after curing, based on HPLC measurements, was about 400 µg (12.9% recovery, ■) in the overlayer, and about 478 µg (14.22% recovery, ♦) in the first coating (underlayer) for the 200° F. conditions. The initial drug loading after curing, based on HPLC measurements, was about 1536 µg (48.14% recovery, X) in the overlayer, and about 1158 µg (26.00% recovery, ▲) in the first coating (underlayer) for the 150° F. conditions. It is to be noted that the percentage amount recovered is dependent on the coating weight and amount of drug detected using HPLC methods after drug extraction from the cured fish oil coating.

These results show that adjusting curing temperature and drug layer coating position can also alter the release of Cyclosporine A, an anti-proliferative. Both the first layer (encapsulated) and overlayer samples cured at 150° F., due to the lower amount of cross-linking, release more rapidly than the more cross-linked samples cured at 200° F. For both the coatings cured at 150° F. or 200° F., the position of the drug in the first coating results in a faster dissolution than for the overlayer coating. Finally, the drug extraction results show that the Cyclosporine A, which is a peptide, is more stable using the 150° F. curing conditions.

In Combination with Vitamin E

All coated mesh samples were 1×1" and dissolution was performed in 0.01 M PBS solution. All drug samples were loaded as an cured first layer on the mesh and were created by mixing the liquid fish oil and drug together, with or without solvent, followed by coating a piece of bare mesh and curing at 150° F. for 3 days.

Figure 23:
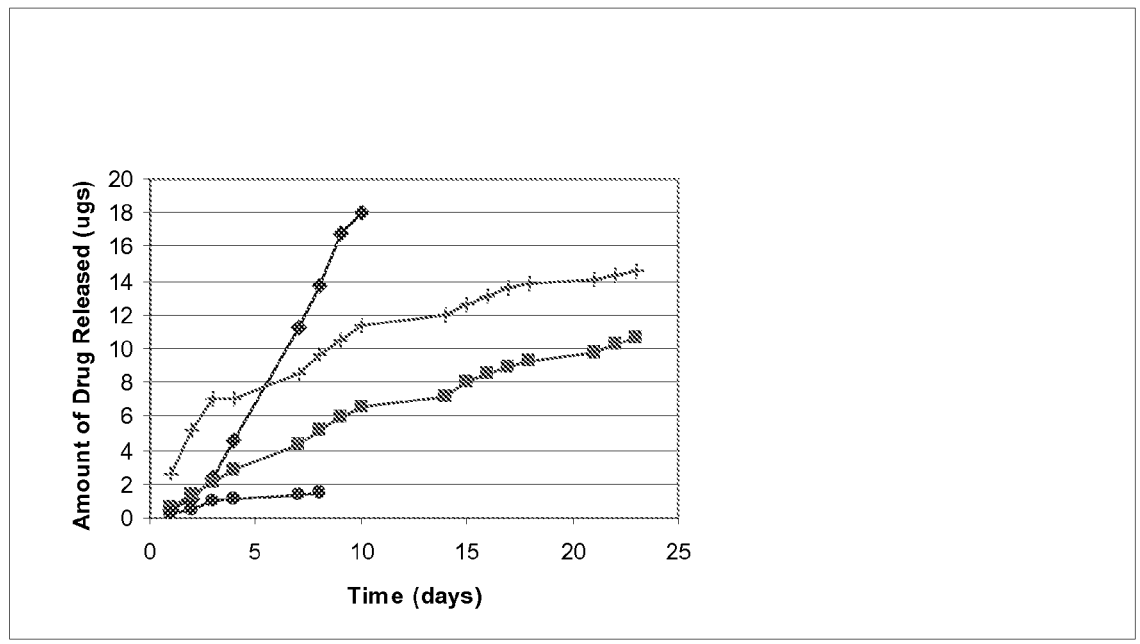

FIG. 23 depicts the drug release profile measured for rapamycin. The figure compares varying amounts of vitamin E added to the starting material prior to curing for 3 days at 150° F. The starting materials comprised 4.88% rapamycin (after solvent removal) in varying amounts of vitamin E in fish oil coatings (0-5%). The initial drug loading for the 100% fish oil sample (no vitamin E) was after curing, based on HPLC measurements, was about 270 µg (5.5% recovery, •) in the overlayer, and about 378 µg (16.5% recovery, ♦) in the first coating (underlayer). The initial drug loading for the 5% vitamin E in fish oil sample was after curing, based on HPLC measurements, was about 3584 µg (66.7% recovery, +) in the overlayer, and about 3013 µg (52.2% recovery, ■) in the first coating (underlayer). It is to be noted that the percentage amount recovered listed in Table 2 is dependent on the coating weight and amount of drug detected using HPLC methods after drug extraction from the cured fish oil coating.

These results show that altering the vitamin E composition can alter the release of a therapeutic from the cured fish oil coating. Increasing the amount of vitamin E results in lengthening and slowing the release of the rapamycin into the dissolution buffer, due to its enhanced solubility and affinity for the vitamin E component in the cured fish oil coating. Additionally, the cured 5% vitamin E/fish oil overlayer coating results in an increase in the amount of drug released when compared to the encapsulated mesh.

Example 5

Figure 24A:
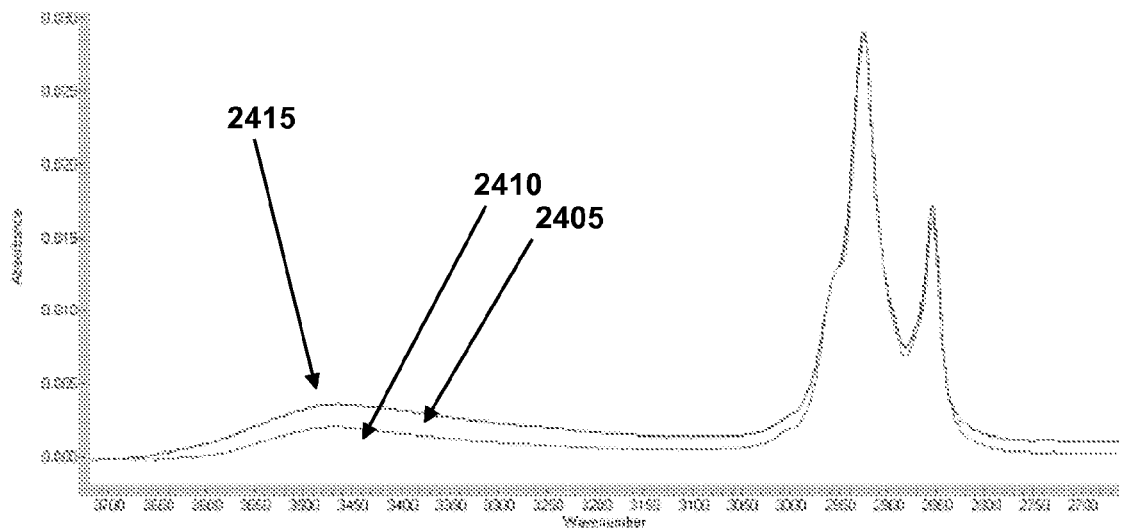
FIGS. 24A-B and depict 25A-B an FTIR comparison analysis of a heat cured encapsulated mesh coating and a UV and heat cured film coating.

Heat Cured Encapsulated Mesh Coating Compared with a UV and Heat Cured Film Coating A comparison of the FTIR spectra of a heat cured encapsulated mesh coating and a UV and heat cured film coating in FIGS. 24A and B. An encapsulated mesh coating (2410) cured solely at 200° F. for 24 hours was compared to a film (2405) that was first UV-cured for 15 minutes at 254 nm followed by heat curing for 24 hours at 200° F. FIG. 24A presents the FTIR spectral band region from 3600-2700 cm$^{-1}$ and demonstrates that the OH band (2415) is greater for the cured film than the encapsulated mesh due to the greater amount of glyceride, fatty alcohol and fatty acid byproducts formed in the film using the additional UV curing step.

Figure 24B:
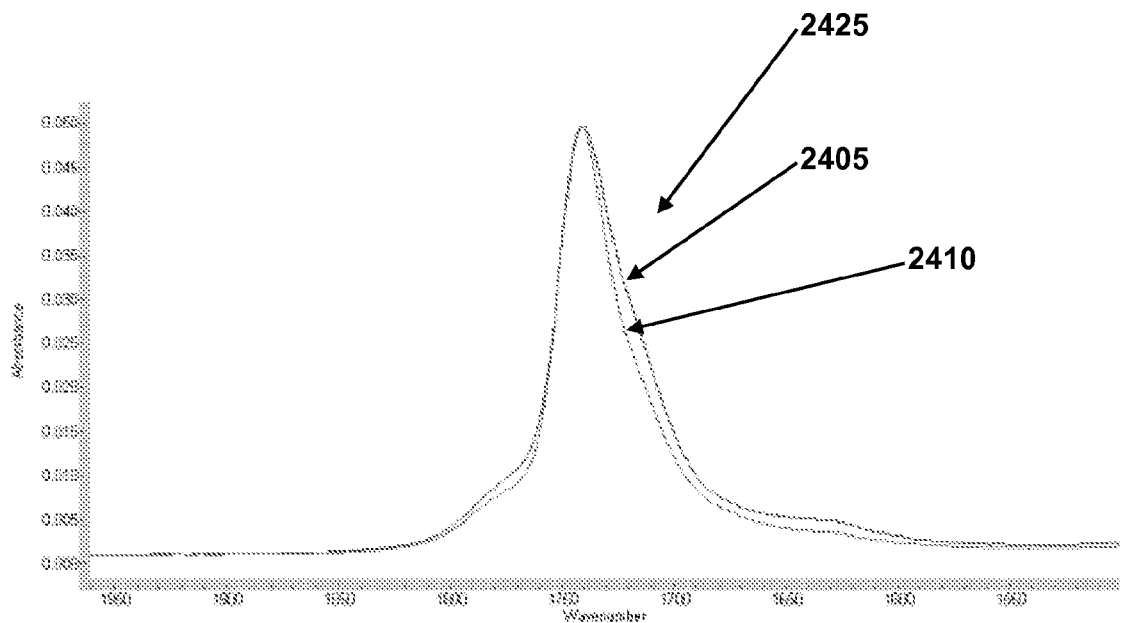

Inspection of the carbonyl band (FIG. 24B) illustrates an approximate 24% increase in the cross-linking absorption at 1775 cm$^{-1}$ for the cured film coating when compared to the encapsulated mesh coating. Additionally, increased fatty acid absorption (2425) in the cured film coating is also observed. Thus, by FTIR analysis, the cured film coating is more oxidized and cross-linked than the encapsulated mesh coating using the processing conditions described.

The effect of the amount of cross-linking on the ability for the film and encapsulated mesh coatings to be hydrolyzed was tested using a saponification (i.e., hydrolysis of coating) test. The test was performed by placing a measured amount of the coating into a 20 ml glass scintillation vial with 20 ml of 0.1 M NaOH. The amount of time for the coating to be hydrolyzed and be dissolved into solution was determined to be approximately 18 minutes for the encapsulated mesh coating and 45 minutes for the film, which coincides with the FTIR spectral data where film was more cross-linked and thus took longer to saponify in basic conditions.

Figure 25A:
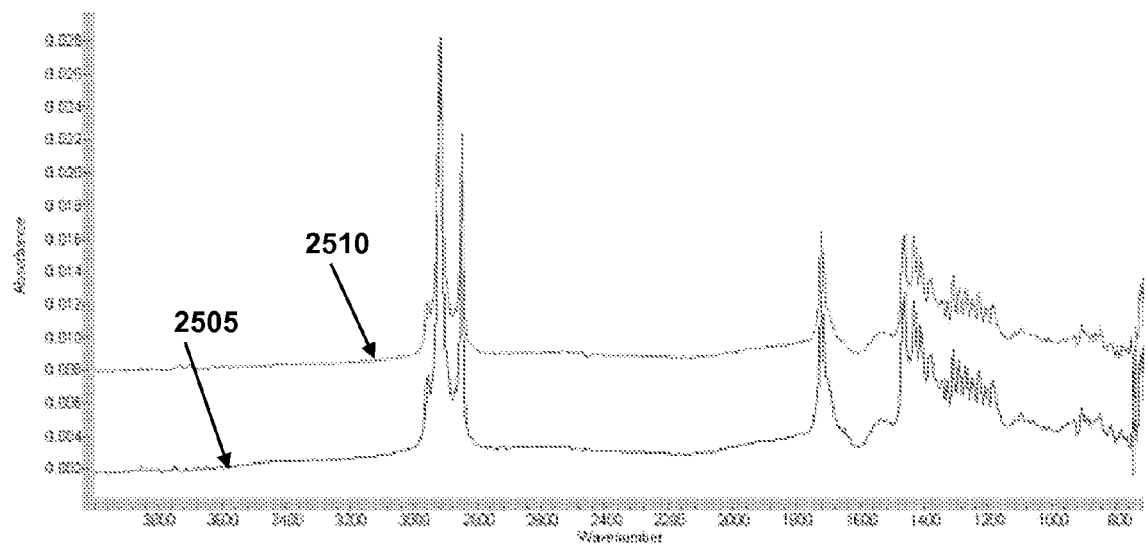
Figure 25B:
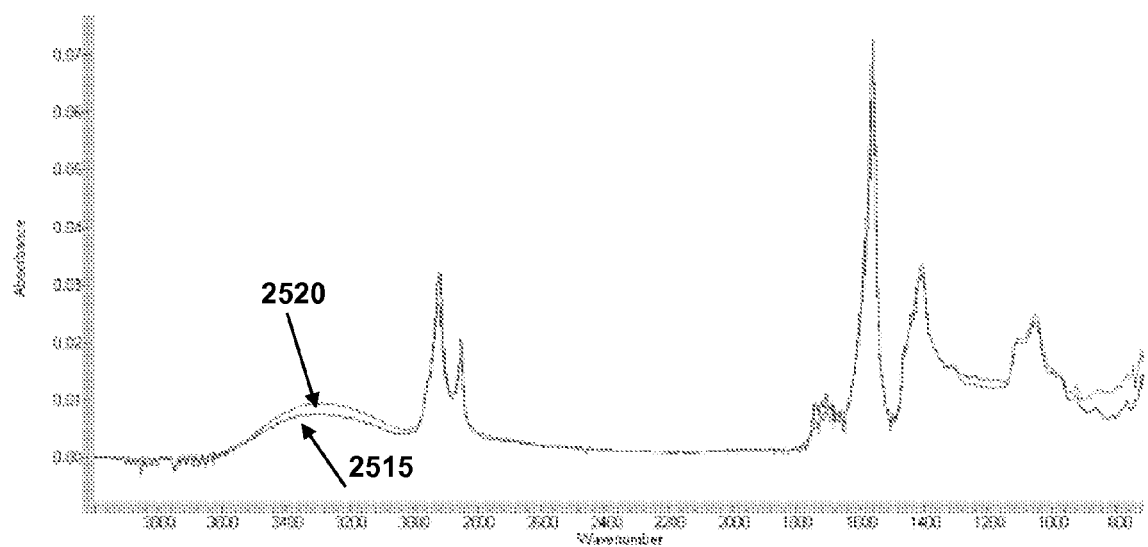

FTIR analysis (FIGS. 25A and B) was also performed of the saponified coating in solution after pH neutralization using HATR. The saponified solution is clear at high pH (11) conditions, but becomes cloudy at a pH approaching 7 due to the partial conversion of fatty acid salts to protonated fatty acids. The solution was centrifuged and the supernatant for each sample was removed for FTIR analysis. The pellet was washed and re-suspended in water twice prior to analysis. As can be seen from FIG. 25A, the FTIR of the pellet for the film (2505) and the encapsulated mesh coating (2510) are almost identical. FIG. 25B illustrates that there is only a slight difference in peak intensities between the supernatant samples of the film (2515) and the encapsulated mesh (2520), which is believed to be a result of slight differences in the pH adjustment. Therefore, the FTIR data demonstrates that although differences in initial byproduct formation and cross-linking are observed, the final chemistry is approximately the same and only the kinetics of the hydrolysis of the coating are affected.

Example 6

HPLC Dissolution for Cured Fish Oil Gels

An HPLC method was used to quantify drug dissolution in vitro. A Symmetry C8 (5 µm 4.6×250 mm) column with a mobile phase, 50% acetonitrile/50% (0.2% Acetic Acid) mobile phase and a 278 nm UV detector was employed in this study. HPLC samples were prepared for dissolution with an acetonitrile diluent.

Figure 26A:
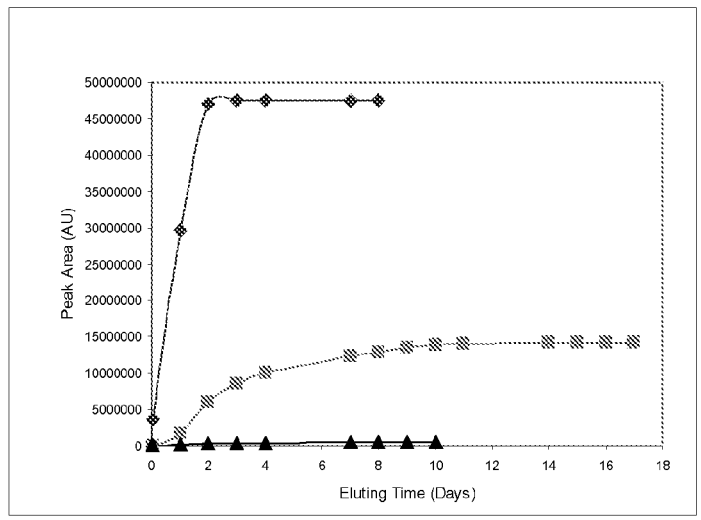
FIGS. 26A-C depict curves illustrating the release of a rapamycin compound in an aqueous media from the coating over time.
Figure 26B:
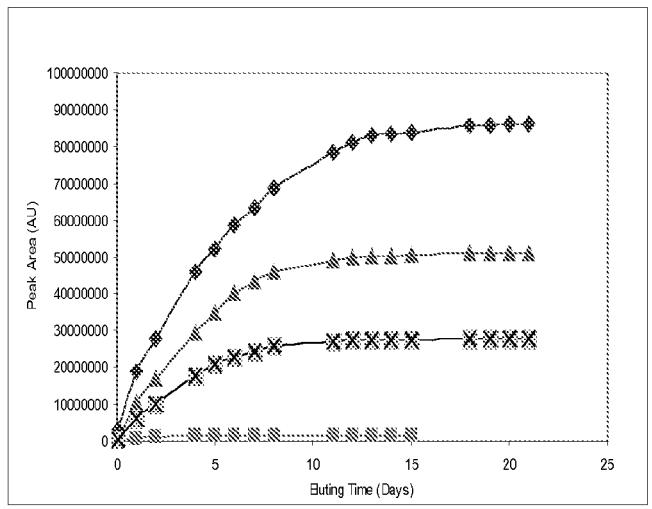
Figure 26C:
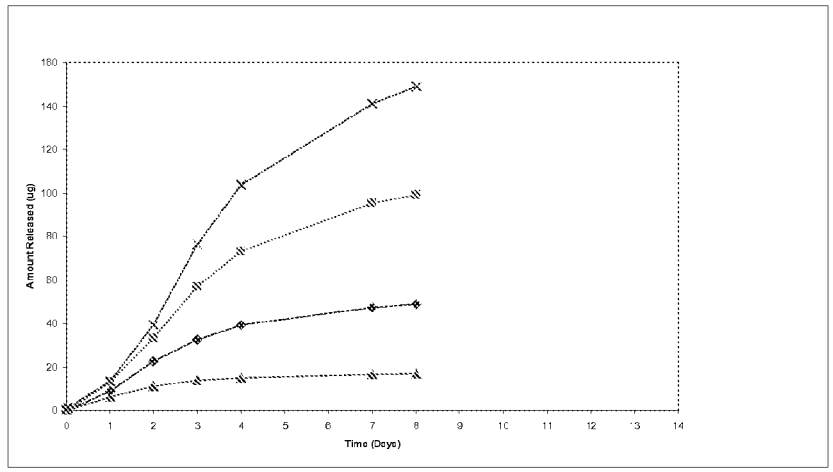

The drug release profiles for the cured fish oil coated stent were quantified with HPLC the above-described dissolution method. The HPLC results are shown in FIGS. 26A-C. Overall, these experiments indicated that release drug profile could be controlled through adding an additive (e.g., TPGS), by the coating process, as well as the coating structures.

Additives

An additive, alpha-tocopherol polyethylene glycol—1000 Succinate (TPGS), was evaluated for the application for quick release of the rapamycin compound (FIG. 26A). A coating formulation was prepared with 11.8% TPGS and 41.2% of rapamycin compound along with a fish oil coating. The formulation was applied to a stent and was uncured (♦), cured for 24 hours at 93° C. (■) or cured at 93° C. for 72 hours (▲). The coated stents were then exposed to the dissolution conditions, and the resulting supernatant was analyzed by HPLC. The data shown in FIG. 26A illustrates that the uncured coating released the rapamycin compound more quickly than the cured coatings and that the length of the curing was an important factor in the drug release, as the coating cured for 72 hours released the rapamycin compound slower than the coating cured for 24 hours. In addition, this assay indicated that while TPGS was not a primary antioxidant, but was a good surfactant.

Curing Time

FIG. 26B illustrates that cure time of the coating is an important factor in the drug release profile of the rapamycin compound. A series of stents were coated with a coating formulation containing 11.8% vitamin E and 41.2% of the rapamycin compound in the coating. The stents were then cured at 93° C. for 0 hours (♦), 24 hours (▲), 48 hours (X) or 72 hours (■). The sterns were then exposed to the dissolution conditions, and the supernatant was analyzed by HPLC. The results indicate that there is an inverse correlation between the rate of drug release and the length of time of curing or cure time.

Thickness of Coating

FIG. 26C illustrates that the thickness and amount of the coating is an important factor in the drug release profile of the rapamycin compound. A series of stents were coated with a fish oil formulations comprising the rapamycin compound in the amount of 106.1 µg (▲), 221.1 µg (♦), 376.2 µg (■) or 519.6 µg (X). The stents were then exposed to the dissolution conditions, and the supernatant was analyzed by HPLC. The results indicate that there is a direct correlation between the amount of coating applied to the medical device and the amount of the drug released.

Example 7

Sterilization of Cured Fish Gels

An MTT cell proliferation assay was performed on the pre-cured and post-cured fish oil coating. The MTT test measures in vitro living rat smooth muscle cells and the results were directly related to the number of viable cultured cell lines. In this cell assay, the yellow tetrazolium salt (MTT) was reduced in metabolically active cells to form insoluble purple formazan crystals, which were solubilized by the addition of a detergent. The assay was used to quantify the activity of the rapamycin compound cured in various coating formulations on smooth muscle cells using a fluorescent plate reader A linear relationship between cell number and absorbance was established, which enabled quantification of changes in proliferation.

Figure 27:
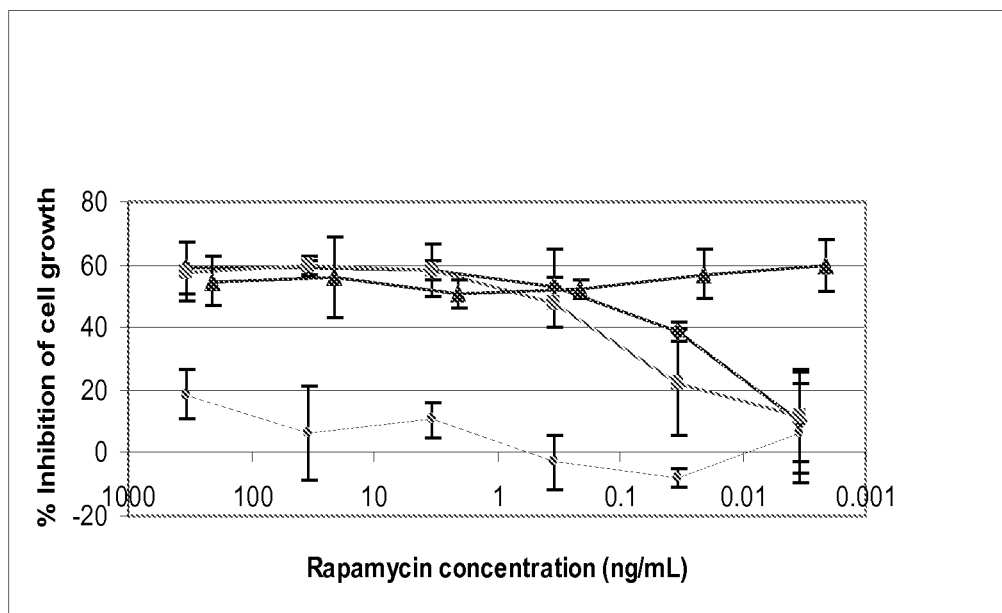
FIG. 27 depicts the percent inhibition of cell growth based on the concentration of rapamycin released from the coating.

The MTT cell assay, the results of which are shown in FIG. 27, was used to determine whether the cured fish oil coatings were stable to sterilization conditions. A series of stents were coated with a fish oil formulation comprising the rapamycin compound and were screened with the MTT cell assay for the % inhibitor of growth of the cells as a function of the rapamycin concentration. The samples included a coating without the rapamycin compound and sterilized by cold ETO gas (•), a coating with the rapamycin compound without sterilization (♦), a coating with the rapamycin compound and sterilized before curing (■) and a coating with the rapamycin compound and sterilized after curing (▲). These results indicate that cured fish oil gel can be sterilized.

Example 8

FTIR Analysis of Implanted Coated Mesh Samples

This study was performed to assess the coating described herein after implantation in a rat abdominal wall defect for various lengths of time. Mesh samples were implanted in a rat abdominal wall defect for 4, 7, 14, 21, and 28 days. At each timepoint, the entire piece of mesh and some surrounding tissue was explanted, wrapped in saline soaked gauze and placed in specimen containers. Sections of the explanted mesh (approx. 1 cm×1 cm) were dissected, soaked in NERL water overnight in a refrigerator and air dried in a hood overnight. The dried mesh explants were analyzed using the Micro-ATR accessory on both the rough (against the subcutaneous tissue) and smooth (against visceral tissue) sides in addition to using HATR to analyze bulk sections of the coating.

FTIR analysis was performed on a bulk section of the coating using the HATR accessory to obtain a detailed chemical analysis of the coating. The HATR technique was better suited to determine a detailed chemical analysis on the implanted coating due to its ability to analyze a greater amount of the sample at one time, resulting from its increased sampling area and IR beam penetration depth, when compared to the Micro-ATR technique. Since Micro-ATR analyzes a smaller area of the sample than the HATR with a 30% less IR beam penetration depth, coating analysis became problematic due to protein absorption on the surface of the device over time.

Physically, the explants were observed to have increased tissue in-growth on the rough side over time. This in-growth was very difficult to remove at the later time points (21 and 28 days). A very thin layer of tissue was noted over the smooth side of the explants at the later time points (21 and 28 days). This layer of tissue was not attached to the coating, but was lying on top of it and was easily removed. In addition, the coating appeared to dissolve over the course of the study as indicated by a visible thinning of the coating where bare polypropylene fibers were exposed where they are normally buried on the continuous smooth side of the coating prior to implantation.

Figure 28A:
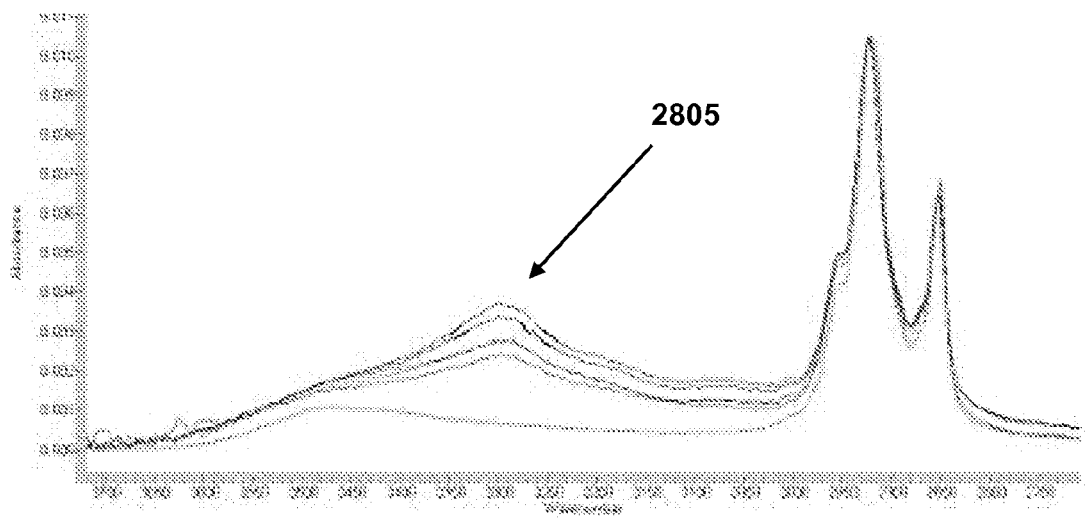
FIGS. 28A-D depict FTIR data discussed in Example 7.
Figure 28B:
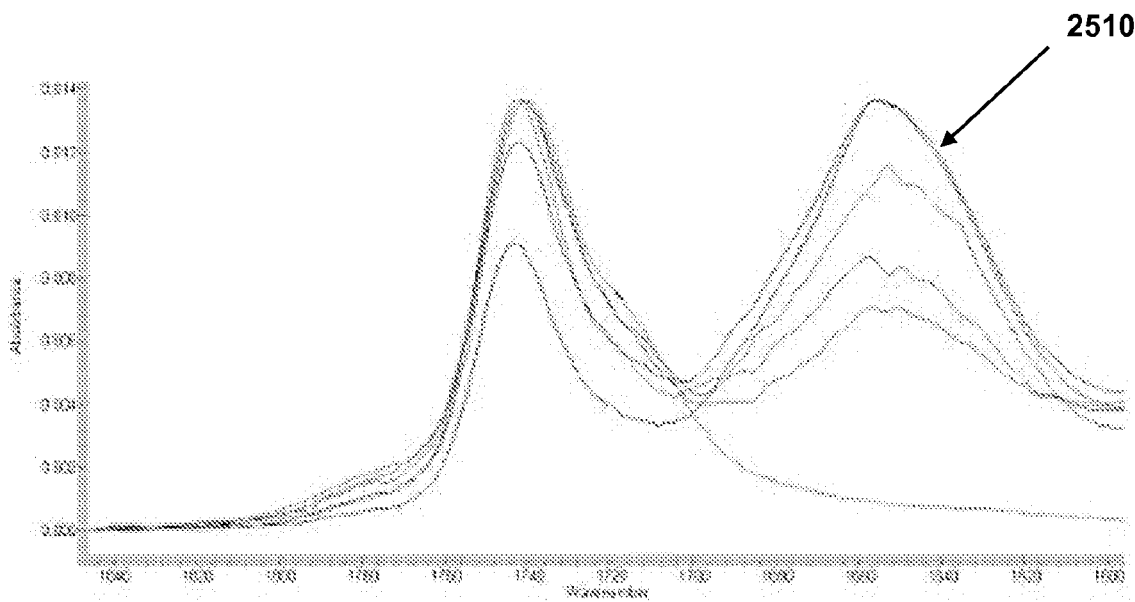

FIGS. 28A and B show the FTIR results for explanted coatings analyzed using HATR at varying time points for the OH, NH, and $CH_2$ absorption regions. The FTIR data shows a greater increase in protein integration into the coating with increasing implantation time as determined by increases in the N—H (~3285 $cm^{-1}$) (2805) and amide I vibrations (~1645 $cm^{-1}$) (2810) in FIG. 28A and FIG. 28B, respectively. These results correlate with the physical observation of increased tissue in-growth on the rough side of the mesh with increased implantation time, especially after 21 days. Micro-ATR results confirmed this observation with greater amounts of protein absorption on the rough side (subcutaneous) when compared to the smooth side (visceral).

Figure 28C:
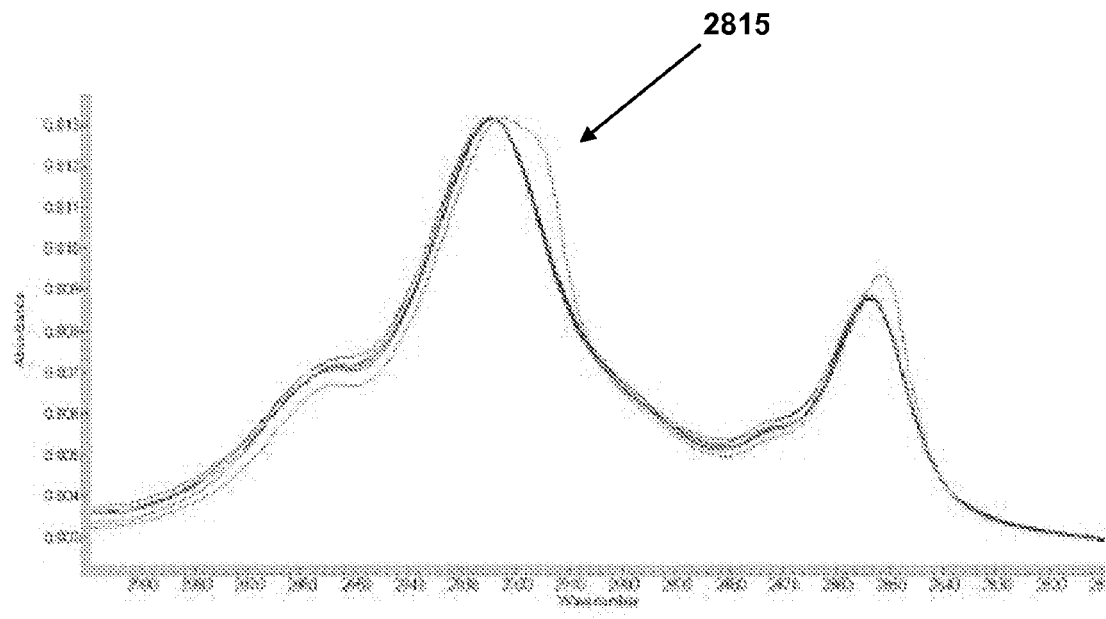
Figure 28D:
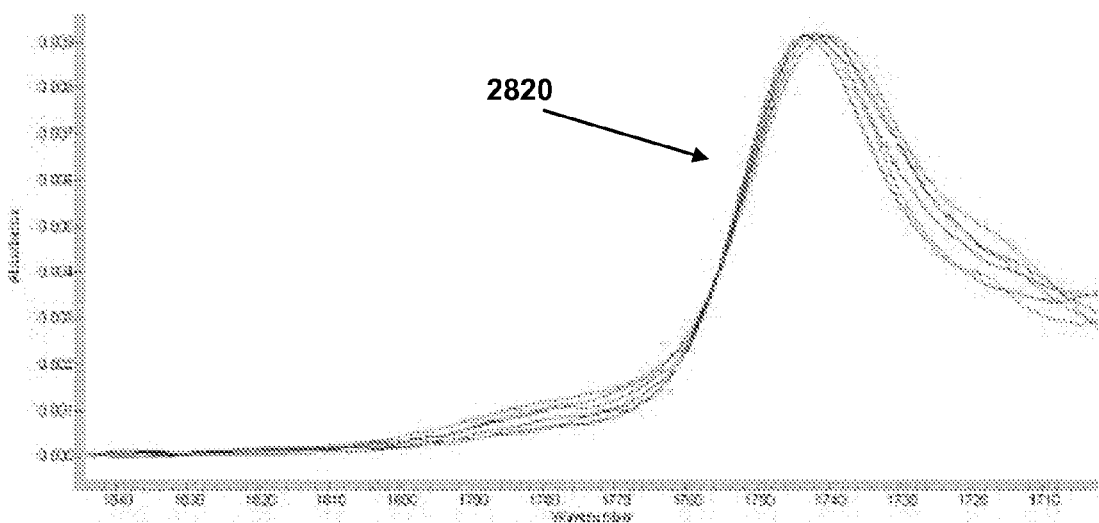

The FTIR data also shows a time dependent conversion and absorption of the coating. Possible absorption and/or hydration of fatty acid byproducts from the coating were initially observed in the shifting of the $CH_2$ band when comparing the T=0 spectrum, where fatty acid crystallization (i.e., bloom) is detected at ~2917 $cm^{-1}$ (2815), but notably absent in the spectra at all other time points (FIG. 28C). This result is more dramatically presented in the sharpening and shifting of the carbonyl band towards ~1745 $cm^{-1}$ (FIG. 28D, 2820) as a function of increasing implantation time. The carbonyl band of the coating is broad due to the combination of several functional group vibrations. One component of this band is due to the ester carbonyl vibrations of the predominantly cross-linked glycerides (mono-, di-, and tri-) centered at ~1740 $cm^{-1}$, where the another component is due to the presence of mostly fatty acid with some ketone and aldehyde byproducts from ~1730-1700 $cm^{-1}$. Thus, the shifting of the carbonyl band towards 1745 $cm^{-1}$ is a result of absorption of the shorter chain length fatty acid/aldehyde/ketone byproducts in the coating by tissue in addition to breaking down of the cross-linked glyceride component of the coating. The break down of the cross-linked glyceride component of the coating is confirmed by the time-dependent decrease in the aliphatic peroxide/anhydride/lactone cross-linking band at ~1780 $cm^{-1}$.

Figure 29:
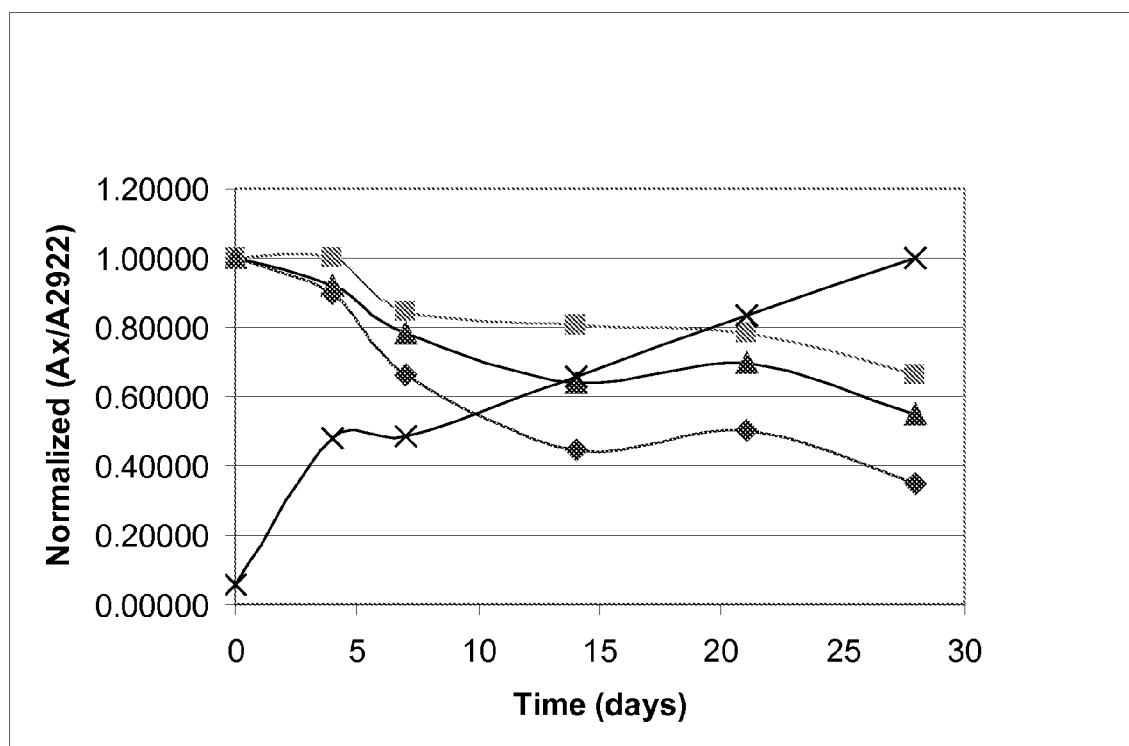
FIG. 29 depicts an analysis of the FTIR data discussed in Example 7.

FIG. 29 shows the plot of the normalized changes in anhydride/aliphatic peroxide/lactone cross-linking (♦), glyceride ester (■), fatty acid (▲), and protein (X) band peak height normalized to the $CH_2$ antisymmetric stretch as a function of time. This data numerically summarizes the changes in peak height observed in the FTIR data discussed above. These results show that the mesh coating is being broken down and absorbed in vivo. Chemically, it appears that it is occurring by the absorption of the short chain fatty acid, ketone, and aldehyde byproducts in addition to the breaking down the aliphatic peroxide, anhydride, and lactone cross-linking bands. From literature studies on the metabolism of triglycerides and fatty acids in the GI tract in vivo, we would expect the shorter chain length byproducts to be absorbed more quickly than the cross-linked glyceride components. The FTIR data appears to be consistent with this result. Without being bound by any particular theory, based on the breakdown of the cross-linking bands and prior literature, the FTIR data supports a hydrolysis and/or enzymatic (i.e., lipase) degradation of the coating.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail may be made without departing from the scope of the appended claims. Therefore, all embodiments that come within the scope and spirit of the following claims and equivalents thereto are claimed.

What is claimed is:

1. A medical device coating material comprising:
    two or more fatty acids, wherein the two or more fatty acids are cross-linked to each other by ester bonds, wherein the coating material comprises one or more therapeutic agents, and wherein the coating hydrolyzes in vivo into substantially non-inflammatory compounds.

2. The coating material of claim 1, wherein the two or more fatty acids are omega-3 fatty acids.

3. The coating material of claim 2, wherein the omega-3 fatty acids are selected from the group consisting of eicosapentaenoic acid (EPA), docosahexanoic acid (DHA), alpha-linolenic acid (ALA), and combinations thereof.

4. The coating material of claim 1, further comprising a medical device, wherein the coating material is disposed on the medical device.

5. The coating material of claim 4, wherein the medical device is selected from the group consisting of stents, catheter balloons, surgical meshes and encapsulated surgical meshes.

6. The coating material of claim 1, wherein the substantially non-inflammatory compounds comprise one or more of free fatty acids and glycerols.

7. The coating material of claim 1, wherein upon hydrolysis of the coating in vivo the one or more therapeutic agents are released from the coating.

8. The coating material of claim 7, wherein the one or more therapeutic agents are released from the coating over a period of at least about seven days.

9. The coating material of claim 7, wherein the one or more therapeutic agents are released from the coating over a period of at least about fourteen days.

10. The coating material of claim 7, wherein the one or more therapeutic agents are released from the coating over a period of at least about twenty-one days.

11. The coating material of claim 1, further comprising vitamin E.

12. The coating material of claim 1, further comprising one or more of monoglycerides, diglycerides and triglycerides.

13. The coating material of claim 12, wherein the source of the one or more of monoglycerides, diglycerides and triglycerides is a fish oil.

14. The coating material of claim 1, wherein the source of the fatty acids is a fish oil.

15. The coating material of claim 1, further comprising two or more fatty acids cross-linked to each other by lactone bonds.

16. A method of treating a vascular injury of a subject, wherein the method comprises:
   positioning a medical device proximal the vascular injury, the medical device coated with a material comprising two or more fatty acids cross-linked to each other by ester bonds, wherein the coating material comprises one or more therapeutic agents, and wherein the coating hydrolyzes in vivo into substantially non-inflammatory compounds; and
   deploying the medical device at the location of the vascular injury of the subject to thereby treat the vascular injury.

17. The method of claim 16, wherein the vascular injury is selected from the group consisting of atherosclerosis, vascular occlusions, restenosis, and combinations thereof.

18. The method of claim 16, wherein the therapeutic agent is selected from the group consisting of an anti-inflammatory agent, an anti-coagulant agent, an anti-proliferative agent, an anti-neoplastic agent and combinations thereof.

19. A medical device coating material comprising two or more fatty acids, wherein the two or more fatty acids are cross-linked to each other by one or more of ester bonds and lactone bonds, and wherein the coating is bio-absorbable.

20. The coating material of claim 19, further comprising one or more therapeutic agents.

21. The coating material of claim 19, wherein the coating hydrolyzes in vivo into substantially non-inflammatory compounds selected from the group consisting of free fatty acids, glycerols, and combinations thereof.

22. The coating material of claim 19, further comprising esters of fatty acids.

23. The coating material of claim 19, wherein the coating is hydrophobic.

24. The coating material of claim 19, further comprising one or more of monoglycerides, diglycerides and triglycerides, wherein the fatty acids and the one or more of monoglycerides, diglycerides and triglycerides are covalently cross-linked in a substantially random configuration.

25. The coating material of claim 24, wherein the source of the fatty acids and the one or more of monoglycerides, diglycerides and triglycerides is an oil containing starting material, and wherein the oil containing starting material is a fish oil.

* * * * *